US012708676B2

(12) United States Patent
Sarraf et al.

(10) Patent No.: US 12,708,676 B2
(45) Date of Patent: Aug. 18, 2026

(54) PHOSPHATE COMPOUNDS FOR DETECTING NEUROLOGICAL DISORDERS

(71) Applicant: Amydis, Inc., Los Angeles, CA (US)

(72) Inventors: Stella Sarraf, Beverly Hills, CA (US); Lyndsay M. Randolph, San Diego, CA (US); Suhail Rasool, San Diego, CA (US)

(73) Assignee: Amydis, Inc., Los Angeles, CA (US)

( * ) Notice: Subject to any disclaimer, the term of this patent is extended or adjusted under 35 U.S.C. 154(b) by 0 days.

(21) Appl. No.: 18/193,570

(22) Filed: Mar. 30, 2023

(65) Prior Publication Data

US 2024/0033380 A1 Feb. 1, 2024

Related U.S. Application Data

(63) Continuation of application No. 17/290,727, filed as application No. PCT/US2019/059538 on Nov. 1, 2019, now abandoned.

(60) Provisional application No. 62/855,442, filed on May 31, 2019, provisional application No. 62/755,331, filed on Nov. 2, 2018.

(51) Int. Cl.

*C07F 9/59* (2006.01)
*A61K 9/00* (2006.01)
*A61K 49/00* (2006.01)
*A61P 25/16* (2006.01)
*A61P 25/28* (2006.01)

(52) U.S. Cl.

CPC ........ *A61K 49/0021* (2013.01); *A61K 9/0048* (2013.01); *A61P 25/16* (2018.01); *A61P 25/28* (2018.01); *C07F 9/59* (2013.01)

(58) Field of Classification Search

CPC ...... A61P 25/28; A61P 25/16; A61K 49/0021; C07F 9/59

See application file for complete search history.

(56) References Cited

U.S. PATENT DOCUMENTS 5,043,013 A 8/1991 Kluger et al.
5,413,996 A 5/1995 Bodor
6,048,662 A 4/2000 Bruhnke et al.
6,541,454 B1 4/2003 Breuer et al.
9,452,985 B2 9/2016 Kudo et al.
10,005,745 B2 * 6/2018 Yang .................... C07D 211/06
10,370,345 B2 * 8/2019 Yang .................... C07C 311/35
10,934,264 B2 * 3/2021 Yang .................... C07D 401/04
11,718,596 B2 * 8/2023 Yang .................... C07D 401/14 514/23
2002/0036750 A1 3/2002 Eberl et al.
2006/0115516 A1 6/2006 Pearson et al.
2009/0163545 A1 6/2009 Goldfarb
2012/0101371 A1 4/2012 Verdooner
2012/0282169 A1 11/2012 Duan et al.
2012/0302603 A1 11/2012 Yang et al.
2013/0135580 A1 5/2013 Hartung et al.
2014/0335019 A1 11/2014 Lim et al.
2015/0177262 A1 6/2015 Yang et al.
2015/0344954 A1 12/2015 Patel et al.
2016/0272619 A1 9/2016 Mcknight et al.
2016/0326126 A1 * 11/2016 Yang .................... C07D 409/10
2017/0248616 A1 8/2017 Sarraf
2018/0127828 A1 5/2018 Belli et al.
2018/0327373 A1 11/2018 Yang et al.
2019/0033328 A1 1/2019 Tokuda et al.
2020/0123118 A1 4/2020 Yang et al.
2020/0138351 A1 5/2020 Kerbage et al.
2021/0369873 A1 12/2021 Sarraf et al.
2021/0371390 A1 12/2021 Yang et al.
2022/0001033 A1 1/2022 Sarraf et al.
2022/0370642 A1 11/2022 Sarraf et al.
2024/0165274 A1 5/2024 Sarraf et al.
2024/0208916 A1 6/2024 Yang et al.

FOREIGN PATENT DOCUMENTS

CN 102046638 5/2011
EP 1431280 6/2004
JP 2008013446 1/2008
JP 2013534171 9/2013
WO WO-03020690 3/2003
WO WO-2005040337 5/2005
WO WO-2006057824 6/2006
WO WO-2006059245 6/2006
WO WO-2007139149 12/2007

(Continued)

OTHER PUBLICATIONS

Jornada et al. (Molecules. Jan. 2016; 21(1): 42. Published online Dec. 29, 2015. doi: 10.3390/molecules21010042). (Year: 2016).*

Oslob et al. ("Water-soluble prodrugs of an Aurora kinase inhibitor." Bioorg. Med. Chem. Lett. 2009; 19: 1409-1412. doi: 10.1016/j.bmcl.2009.01.043. (Year: 2009).*

Shultz, Carsten, "Prodrugs of biologically active phosphate esters." Bioorg Med Chem. Mar. 20, 2003;11(6):885-98. doi: 10.1016/s0968-0896(02)00552-7. (Year: 2003).*

So et al. Protein Sci. Jun. 2, 2021;30(8):1701-1713. doi: 10.1002/pro.4130. (Year: 2021).*

Extended European Search Report for European Application No. 19878749.1 dated Jun. 24, 2022. 7 pages.

(Continued)

*Primary Examiner* — James H Alstrum-Acevedo
*Assistant Examiner* — Chris E Simmons
(74) *Attorney, Agent, or Firm* — Sheppard Mullin Richter & Hampton LLP

(57) ABSTRACT

Provided herein are compounds, methods and compositions for determining whether a patient has a neurological disease or disorder is provided, comprising detecting the presence of a detectable target protein, or an accumulated mass thereof, for example, amyloid beta protein or phosphorylated tau protein, or an accumulated mass thereof, in a tissue or a sample of the patient. The detecting may comprise contacting the target protein with a compound described herein.

3 Claims, 21 Drawing Sheets

(56) References Cited

FOREIGN PATENT DOCUMENTS

| | | |
|---|---|---|
| WO | WO-2008016682 | 2/2008 |
| WO | WO-2009117728 | 9/2009 |
| WO | WO-2010033861 | 3/2010 |
| WO | WO-2011072257 | 6/2011 |
| WO | WO-2011082617 | 7/2011 |
| WO | WO-2012008767 | 1/2012 |
| WO | WO-2012024188 | 2/2012 |
| WO | WO-2012061078 | 5/2012 |
| WO | WO-2014138919 | 9/2014 |
| WO | WO-2015143185 | 9/2015 |
| WO | WO-2015188142 | 12/2015 |
| WO | WO-2016040891 | 3/2016 |
| WO | WO-2016055148 | 4/2016 |
| WO | WO-2016153549 | 9/2016 |
| WO | WO-2017004560 | 1/2017 |
| WO | WO-2019232422 | 12/2019 |
| WO | WO-2021055639 | 3/2021 |
| WO | WO-2022192714 | 9/2022 |
| WO | WO-2023288109 | 1/2023 |
| WO | WO-2024155678 | 7/2024 |

OTHER PUBLICATIONS

International Search Report and Written Opinion for International Application No. PCT/US2019/059538 dated Mar. 2, 2020. 11 pages.
Yellapu et al., Design, synthesis, in silico, and in vitro evaluation of novel pyrimidine phosphonates with cytotoxicity against breast cancer cells. Medicinal Chemistry Research 2014, vol. 23, pp. 317-328.
Antonsen et al., "Water Structure of PEG Solutions by Differential Scanning Calorimetry Measurements." J. M. Harris (ed.), Poly(Ethylene Glycol) Chemistry. Springer Science+Business Media New York 1992, pp. 15-28.
Ash, M., "Handbook of Pharmaceutical Additives. Third Edition, Endicott, NY: Synapse Information Resources." (2007) p. 673.
Baertschi, S. W., Pharmaceutical stress testing, Second Edition, Chapter 3, Informa Healthcare, 2011, p. 49-141.
Berge et al. Pharmaceutical Salts. Journal of Pharmaceutical Sciences 66(1):1-19 (Jan. 1977).
Buhimschi, IA et al. Protein misfolding, congophilia, oligomerization, and defective amyloid processing in preeclampsia. Sci. Transl. Med. 6(245):245ra92; pp. 1-14 (Jul. 16, 2014).
Cai, L. Radioligand Development for PET Imaging of β-Amyloid (Aβ)-Current Status. Current Medicinal Chemistry, 14(1):19-52 (Jan. 1, 2007).
Cao, K. et al. Amino Naphthalenyl-2-Cyano-Acrylate (ANCA) Probes Fluorescently Discriminate between Amyloid-β and Prion Plaques in Brain. Journal of the American Chemical Society, 134 (42):17338-17341 (Jan. 1, 2012).
Carey, FA. Organic Chemistry, 6th Edition, McGraw Hill Chapter 1, pp. 1-9. 2006.
Carre et al., Fluorescent Molecular Rotors with Specific Hydrophilic Functions: Glucosamine and Inositol Derivatives. Journal of Fluorescence 8(1): 53-57 (Feb. 16, 1998).
CAS Registry No. 478016-48-7, located at stneasy.cas.org/tmp/20171006/1240090-1942032854-200/479739346.html last visited Oct. 6, 2017, 1 page.
CAS Registry No. 811462-20-1, located at stneasy.cas.org/tmp/20171006/1240090-1942032854-200/33392095.html last visited Oct. 6, 2017, 1 page.
CAS Registry No. 862649-67-0, located at stneasy.cas.org/tmp/20171006/1240090-1942032854-200/740546802. html last visited Oct. 6, 2017, 1 page.
CAS Registry No. 888490-95-7, located at stneasy.cas.org/tmp/20171006/1240090-1942032854-200/490202741.html Oct. 6, 2017, 1 page.
Chang et al., ANCA: A Family of Fluorescent Probes that Bind and Stain Amyloid Plaques in Human Tissue. ACS Chemical Neuroscience 2(5): 249-255 (2011).
Funke "Detection of Soluble Amyloid-β Oligomers and Insoluble High-Molecular-Weight Particles in CSF: Development of Methods with Potential for Diagnosis and Therapy Monitoring of Alzheimer's Disease" IJAD, article 151645 (Year: 2011).
Furumoto, S. et al. Recent advances in the development of amyloid imaging agents. Current Topics in Medicinal Chemistry, 7(18):1773-1789 (Jan. 1, 2007).
Geoffroy-Chapotot et al., Three-Dimensional Fluorescence Microscopy of Endothelial Cells Labeled with Coumarins. Journal of Fluorescence 10(2): 203-207 (Jan. 12, 2000).
Guan et al., Real-Time Monitoring of Alzheimer's-Related Amyloid Aggregation via Probe Enhancement-Fluorescence Correlation Spectroscopy, ACS Chemical Neuroscience 2015, vol. 6, No. 9, pp. 1503-1508.
He et al: "Identification of Binding Modes for Amino Naphthalene 2-Cyanoacrylate (ANCA) Probes to Amyloid Fibrils from Molecular Dynamics Simulations", Journal of Physical Chemistry Part B, vol. 121, 2017, pp. 1211-1221.
International Application No. PCT/US2015/021512 International Search Report and Written Opinion Mailed Aug. 18, 2015.
International Application No. PCT/US2015/049825 International Preliminary Report on Patentability Mailed Mar. 14, 2017.
International Application No. PCT/US2015/049825 International Search Report and Written Opinion Mailed Mar. 23, 2016.
International Preliminary Report on Patentability for International Application No. PCT/US2015/021512 dated Sep. 20, 2016, 9 pages.
International Search Report and Written Opinion for International Application No. PCT/US2019/034977 dated Oct. 16, 2019. 10 pages.
International Search Report and Written Opinion for International Application No. PCT/US2020/051325 dated Dec. 16, 2020. 7 pages.
International Search Report and Written Opinion for International Application No. PCT/US2022/020013 dated Aug. 11, 2022. 15 pages.
International Search Report and Written Opinion for International Application No. PCT/US2022/037387 dated Dec. 19, 2022. 18 pages.
Johnson et al., Traumatic brain injury and amyloid-β pathology: a link to Alzheimer's disease? Nature Reviews Neuroscience, vol. 11, pp. 361-370 (2010), XP055907506.
Knowles, TP et al. The amyloid state and its association with protein misfolding diseases. Nature Reviews Molecular Cell Biology, 15(6):384-396 (Jun. 2014).
Koronyo et al., Retinal amyloid pathology and proof-of-concept imaging trial in Alzheimer's disease, JCI Insight. 2017;2(16):e93621, doi.org/10.1172/jci.insight.93621.
Maruyama, M. et al. Imaging of Tau pathology in a tauopathy mouse model and in Alzheimer patients compared to normal controls. Neuron, 79:1094-1108 (Sep. 18, 2013).
Maruyama, M. et al. Imaging of Tau pathology in a tauopathy mouse model and in Alzheimer patients compared to normal controls. Neuron, Supplemental Information, 79:1-37 (Sep. 18, 2013).
Mathis, C.A. et al. Synthesis and evaluation of $^{11}C$-labeled 6-substituted 2-arylbenzothiazoles as amyloid imaging agents. Journal of Medicinal Chemistry, 46(13):2740-2754 (Jun. 19, 2003).
Mircheva et al., "Properties of β-carotene and retinoic acid in mixed monolayers with dipalmitoylphosphatidylcholine (DPPC) and Solutol." Colloids and Surfaces A: Physicochemical and Engineering Aspects, (2014), 460, pp. 209-218. dx.doi.org/10.1016/j.colsurfa.2013.12.046.
Moda, F. et al. Prions in the Urine of Patients with Variant Creutzfeldt-Jakob Disease, New England Journal of Medicine, 371 (6):530-539 (Aug. 7, 2014).
National Institutes of Health, National Center for Advancing Translational Sciences (NCATS), F751QVSOSX Methoxy PEG-12 Retinamide, drugs.ncats.io/substance/F751QVSOSX#details, accessed Aug. 29, 2022, printed Sep. 20, 2022. 2 pages.
Nelson et al., "Correlation of Alzheimer Disease Neuropathologic Changes With Cognitive Status: A Review of the Literature" J Neuropathol Exp Neurol, 71(5):362-381 (Year: 2012).
Nizynski et al., Amyloidogenesis of Tau protein. The Protein Society, Protein Science 2017, vol. 26, pp. 2126-2150.

(56) References Cited

OTHER PUBLICATIONS

Optos and Amydis Establish Clinical Alliance to Develop Early Diagnostic Test for Alzheimer's Disease. Globe Newswire 2018, Retrieved from the internet globenewswire.com/news-release/2018/10/24/1626139/0/en/Optos-and-Amydis-Establish-Clinical-Alliance-to-Develop-Early-Diagnostic-Test-for-Alzheimer-s-Disease.html. 3 pages.
Pubchem, SID 322288298, Available Date: Jan. 24, 2017 [retrieved on Jul. 11, 2022], Retrieved from the Internet pubchem.ncbi.nlm.nih.gov/substance/322288298.
Pubchem, SID 381923871, Available Date: Apr. 9, 2019 [retrieved on Apr. 18, 2022], Retrieved from the Internet pubchem.ncbi.nlm.nih.gov/substance/381923871.
Purkey et al., "Evaluating the binding selectivity of transthyretin amyloid fibril inhibitors in blood plasma" pnas 98(10):5566-5571 (Year: 2001).
Sanchorawala "Light-Chain (AL) Amyloidosis: Diagnosis and Treatment" ASN, Clin J Am Soc Nephrol, 1: 1331-1341 (Year: 2006).
Silva, et al. Prion-like aggregation of mutant p53 in cancer, Trends in Biochemical Sciences, 39(6):260-267 (2014).
STN-478016-52-3, 2-Propenamide, 2-cyano-3-[4-[ethyl(phenylmethyl)amino]phenyl]-N-(2-methoxyethyl)-, entered Jan. 3, 2003. 1 page.
STN-RN1013518-60-9, 2-Propenamide, 2-cyano-N-(2-rnethoxyethyl)-3-[2-(4-morpholinyl)-3-quinolinyl) entered Apr. 10, 2008. (1 page).
STN-RN1164496-51-8, 2-Propenamide, 2-cyano-N-(2-methoxyethyl)-3-[5-(4-morpholinyl)-2-furanyl], entered Jul. 19, 2009. (1 page).
STN-RN347334-29-6, 2-Propenamide, 2-cyano-3-[4-(dimethylamino)phenyl]-N-(2-methoxyethyl), entered Jul. 22, 2001. (1 page).
STN-RN364768-44-5, 2-Propenamide, 2-cyano-N-(2-methoxyethyl)-3-[5-(4-morpholinyl)-2-furanyl], entered Oct. 26, 2001. (1 page).
STN-RN365234-08-8, 2-Propenarnide, 3-[3-bromo-4-(dimethylamino)phenyl]-2-cyano-N-(2-methoxyethyl), entered Oct. 29, 2001. (1 page).
STN-RN365550-20-5, 2-Propenamide, 2-cyano-N-(2-methoxyethyl)-3-[5-(1-piperidinyl)-2-furanyl], entered Oct. 31, 2001. (1 page).
STN-RN444317-74-2, 2-Propenamide, 2-cyano-3-[4-(diethylamino)-2-methoxyphenyl]-N-(2-methoxyethyl), entered Aug. 20, 2002. (1 page).
STN-RN473875-91-1, 2-Propenamide, 2-cyano-3-[4-(diethylamino)-2-hydroxyphenyl]-N-(2-methoxyethyl), entered Nov. 19, 2002. (1 page).
STN-RN474401-13-3, 2-Propenamide, 2-cyano-3-[4-(diethylamino)phenyl]-N-(2-methoxyethyl], entered Nov. 25, 2002. (1 page).
STN-RN478016-48-7, 2-Propenamide, 2-cyano-N-(2-methoxyethyl)-3-[4-(4-morpholinyl)phenyl], entered Jan. 3, 2003. (1 page).
STN-RN478016-72-7, 2-Propenamide, 2-cyano-3-[4-(diphenylamino)phenyl]-N-(2-methoxyethyl), entered Jan. 3, 2003. (1 page).
STN-RN502908-83-0, 2-Propenamide, 2-cyano-N-(2-methoxyethyl)-3-[2-(4-morpholinyl)-4-phenyl-5-thiazolyl], entered Apr. 14, 2003. (1 page).
STN-RN568557-51-7, 2-Propenamide, 2-cyano-N-(2-methoxyethyl)-3-(5-(4-morpholi nyl)-2-thienyl]-, entered Aug. 18, 2003. (1 page).
STN-RN775314-93-7, 2-Propenamide, 3-[5-chloro-2-(dimethylamino)-1-(4-fluorophenyl)-1H-imidazol-4-yl)-2-cyano-N-(2-methoxyethyl), entered Nov. 5, 2004. (1 page).
STN-RN811462-20-1, 2-Propenamide, 2-cyano-N-(2-methoxyethyl)-3-[2-methoxy-4-(4-morpholinyl)phenyl], entered Jan. 11, 2005. (1 page).
STN-RN862649-67-0, 2-Propenamide, 2-cyano-N-(2-methoxyethyl)-3-[4-(1-piperidinyl)phenyl], entered Sep. 8, 2005. (1 page).
Sutharsan et al., Rational Design of Amyloid Binding Agents Based on the Molecular Rotor Motif. ChemMedChem 5(1): 56-60 (Jan. 2010).
Takata et al., "Detection of amyloid β protein in the urine of Alzheimer's disease patients and healthy individuals" Neurosci Letters 435: 126-130 (Year: 2008).
Teiten et al., Specific Fluorescent Tracers. Imaging and Applications for Photodynamic Therapy. Comptes Rendus Biologies 325: 487-493 (2002).
U.S. Pharmacopeia Convention USP 30, Chemical Tests (467) Residual Solvents. Table 2. Class 2 Residual Solvents. pp. 1-10. Published Mar. 23, 2007. Accessed Apr. 20, 2017.
Kittaka, Astushi, Drug discovery science, Medicinal chemistry, 2007, pp. 142-150.
Nozaki, Medicinal chemistry, pp. 98-99, ISBN4759802819, 1995, published by Kagaku-Dojin Publishing Company.
Petric et al., Dicyanovinylnaphthalenes for neuroimaging of amyloids and relationships of electronic structures and geometries to binding affinities, Proceedings of the National Academy of Sciences of the United States of America, 2012, 109(41), pp. 16492-16497.
Shuto, Satoshi, Molecular theory of organic medicine, 2012, pp. 201-218.
Wermuth, C.G., Chapter 13: Conversion of molecules based on equivalent replacement, The practice of medicinal chemistry 1998, pp. 235-271, published by Technomics, Inc . . . .
Gallardo et al., Amyloid structures: much more than just a cross-β fold, Current Opinion in Structural Biology 2020, 60:7-16.
International Search Report and Written Opinion for International Application No. PCT/US2024/011789 dated Apr. 26, 2024. 9 pages.

* cited by examiner

Clinical signs: Kyphosis and ataxia.

DAY 1 dosed at 15 mg/kg 15 deposits

Day 8 dosed at 15 mg/kg 17 deposits

PHOSPHATE COMPOUNDS FOR DETECTING NEUROLOGICAL DISORDERS

CROSS REFERENCE TO RELATED APPLICATIONS

This application is a continuation application under 35 U.S.C. 111(a) of U.S. application Ser. No. 17/290,727, filed Apr. 30, 2021, which is a U.S. National Stage Application under 35 U.S.C. § 371 of International Application No. PCT/US2019/059538, filed Nov. 1, 2019, which application claims the benefit under 35 U.S.C. § 119(e) to U.S. Provisional Application No. 62/755,331, filed Nov. 2, 2018, and U.S. Provisional Application No. 62/855,442, filed May 31, 2019, all of which are hereby incorporated by reference in their entireties.

BACKGROUND

Neurological disorders are diseases of the brain, spinal cord and peripheral nervous system. The greatest societal costs, in terms of epidemiology and individual morbidity, are imposed by neurological conditions. Among the most prominent of these are Alzheimer's disease and Parkinson's disease. Other neurological conditions include age-related conditions (e.g. Parkinson's dementia, vascular dementia, amyotrophic lateral sclerosis), genetic syndromes (e.g. Down syndrome), injury-related conditions (e.g. traumatic brain injury, chronic traumatic encephalopathy), and conditions typically considered as being purely psychiatric in nature, such as schizophrenia and depression.

Compounds for the detection of these and other neurological disorders are useful in the detection, diagnosis, monitoring and treatment of these diseases.

SUMMARY

The disclosure provides compounds for detecting and treating a neurological disease or disorder. It is found that certain diagnostic compounds useful in the detection of neurological disorder suffer from less than ideal physiochemical properties, for example, low water solubility and high crystallinity. Disclosed herein are compounds with improved physiochemical properties useful for diagnosing and treating neurological disorders.

In some embodiments a method for determining whether a patient has a neurological disease or disorder is provided, comprising administering to the patient a compound described herein. In some embodiments, provided is a method for detecting a neurological disease or disorder in a patient, comprising administering to the patient a compound described herein which is capable of binding a detectable target protein or generating a compound capable of binding a detectable target protein after being administered to the patient, determining the presence or absence of the binding, wherein the presence of the binding indicates that the patient has or is at risk of developing the neurological disease or disorder. The compound may be a compound of Formula I. In some embodiments, the compound is Compound 7, Compound 8, Compound 9, or a pharmaceutically acceptable salt thereof. In some embodiments, the compound is Compound 7, Compound 8, Compound 9, or Compound 10. Thus, provided herein are methods and compositions for determining whether a patient has a neurological disease or disorder, comprising detecting the presence of a detectable target protein, or an accumulated mass thereof, for example, amyloid beta protein or phosphorylated tau protein, or an accumulated mass thereof, in a tissue or a sample of the patient. The detecting may comprise contacting the target protein with a compound described herein.

In some embodiments, the patient does not have any symptom of the disease or disorder to be detected. In some embodiments, the patient has one or more symptoms of the disease or disorder to be detected.

In some embodiments the method comprises administering to a patient a compound described herein. In some embodiments, the administration is intravenous administration or is localized at the retina of the eye. In some embodiments, the administration is a bolus injection. In some embodiments, the administration is topical.

In some embodiments, the neurological disease or disorder is selected from an age-related disease or disorder, a genetic disease or disorder, an injury-related disease or disorder, and a psychiatric disease or disorder. In some embodiments, the age-related disease or disorder is selected from Parkinson's disease, vascular dementia, and amyotrophic lateral sclerosis, the genetic disease or disorder is Down syndrome, the injury-related disease or disorder is selected from traumatic brain injury and chronic traumatic encephalopathy, and the psychiatric disease or disorder is selected from schizophrenia and depression. In some embodiments of the method, the neurological disease or disorder is Alzheimer's disease or traumatic brain injury (TBI).

In some embodiments of the method, the neurological disease or disorder is a prion disease. Accordingly, provided is a method for detecting prion deposition in a patient. In certain embodiments, the detecting is performed in the retina. In certain embodiments, provided is a method for detecting prion deposition in the retina of a patient, wherein the patient may or may not exhibit clinical manifestations of a disease or disorder related thereto, such as Creutzfeldt-Jakob disease (e.g., behavioral changes, confusion, cognitive dysfunction, movement problems, visual disturbances, kyphosis, ataxia, tip toe walking, etc.).

In some embodiments of the method, the neurological disease or disorder is cerebral amyloid angiopathy (CAA). Cerebral amyloid angiopathy (CAA) is a disease of aging characterized by amyloid deposition within cerebral blood vessel walls. Accordingly, in certain embodiments, provided is a method for detecting Aβ40 in a patient. In certain embodiments, the detecting is performed in the retina.

In certain embodiments, the detecting differentiates between the Aβ isoforms Aβ40 and Aβ42.

BRIEF DESCRIPTION OF THE DRAWINGS

FIG. 6A) Staining with Compound 7. FIG. 6B) Staining with 6E10, an anti-A antibody. FIG. 6C) Merged image of A and B showing co-staining of Compound 7 with 6E10 (white arrows).

labeling of amyloid plaques with Compound 7 and 6E10 (white arrows).

Figure 9:
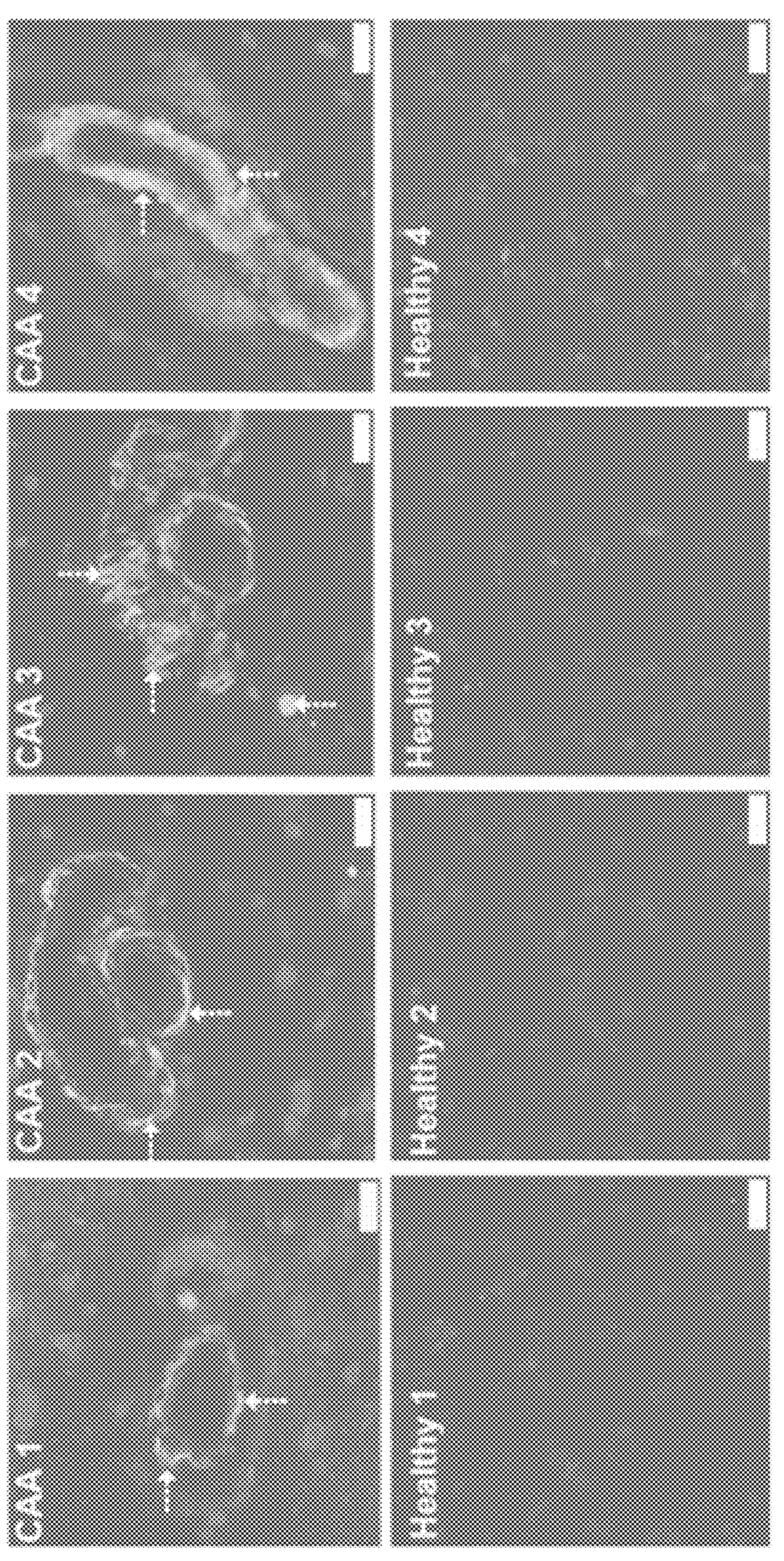

FIG. 9 shows ex vivo staining of human brain tissue from four different patients diagnosed with CAA and four healthy controls. Staining is as follows: blue=DAPI nuclear stain, red=6E10 staining, green/yellow=staining with Compound 7. Scale bar=50 μm. White arrows indicate areas where green/yellow are observed.

Figure 10:
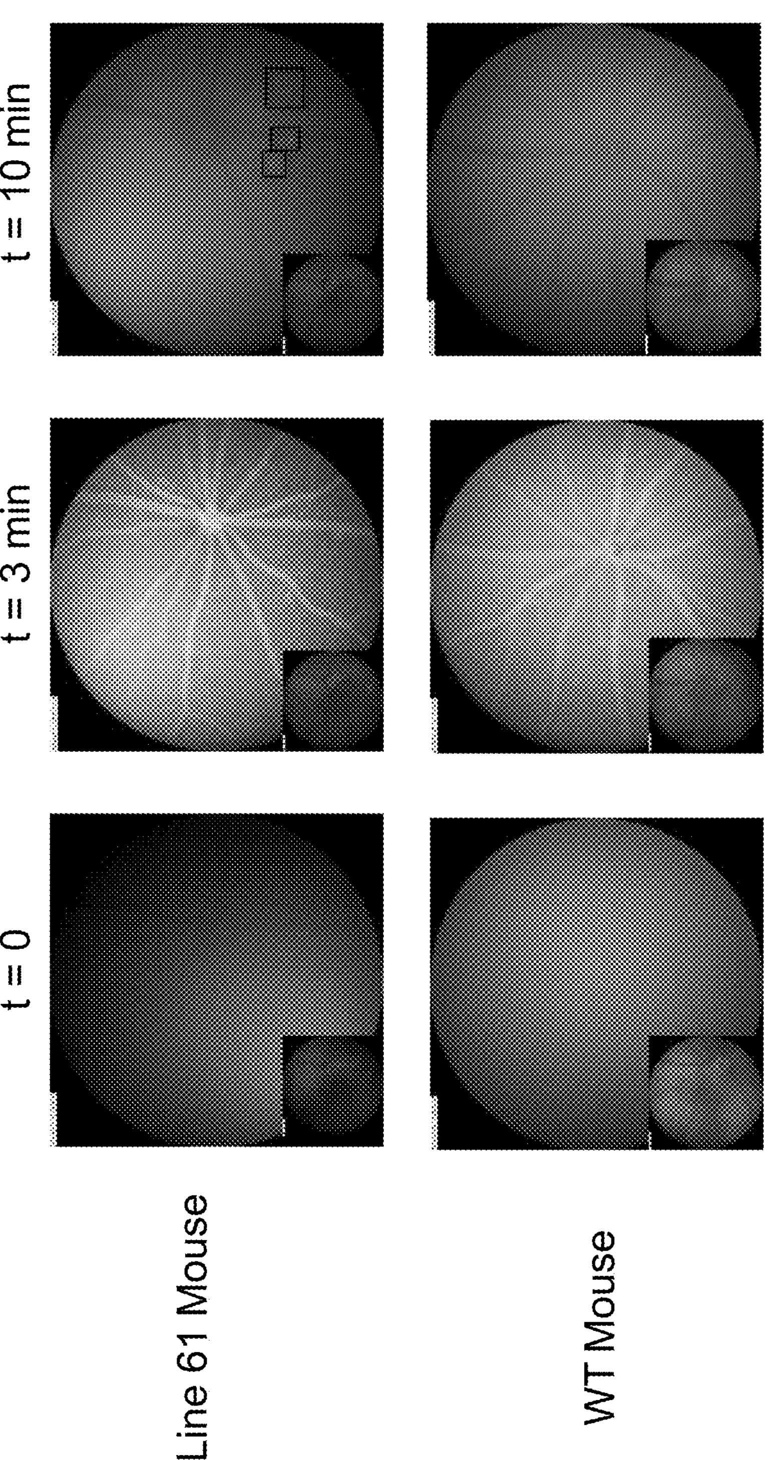

FIG. 10 shows in vivo detection of retinal α-syn deposits associated with Parkinson's Disease using the Line 61 model.

Figure 11:
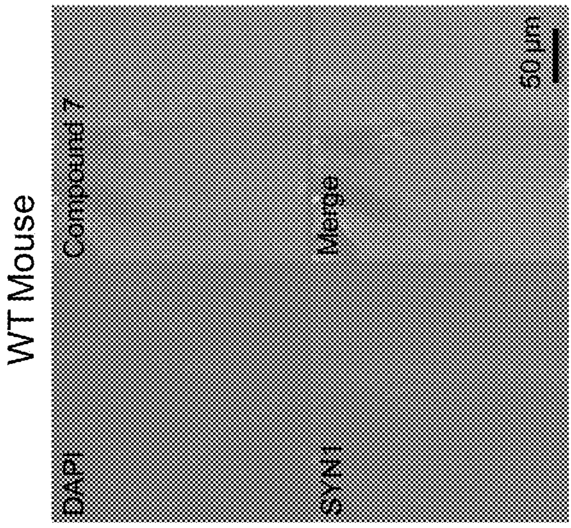
Figure 11:
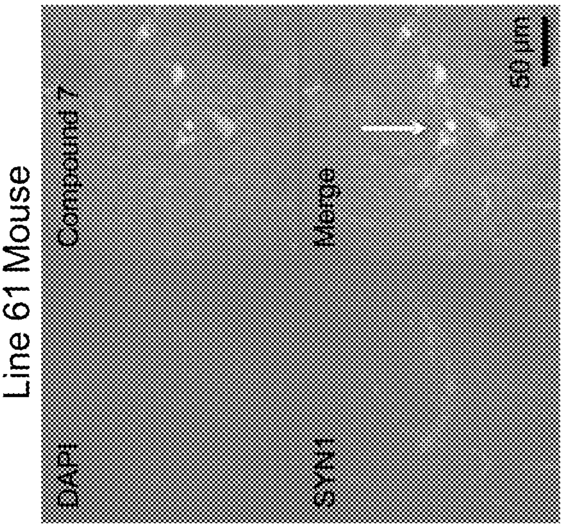

FIG. 11 shows retinal tissue extracted post-mortem from mice stained with DAPI and a SYN1 antibody.

Figure 12:
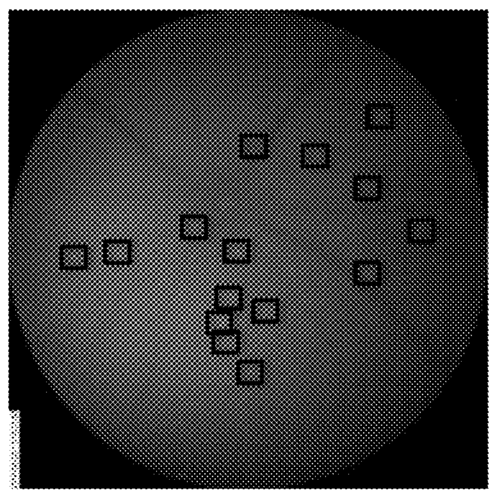

FIG. 12 shows that administration of Compound 10 can reproducibly detect retinal α-syn deposits in the same animal.

Figure 13:
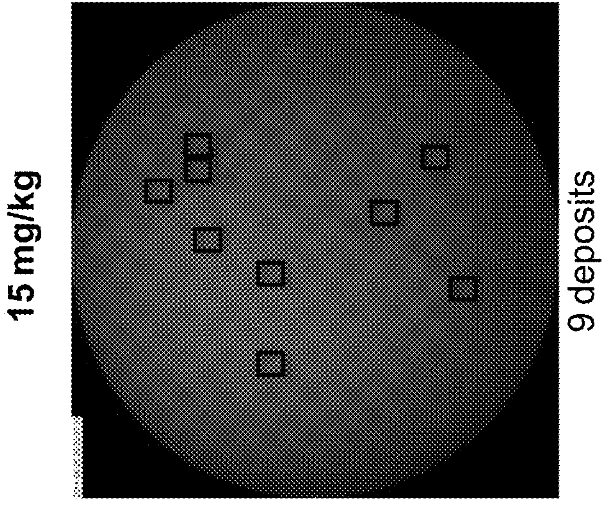
Figure 13:
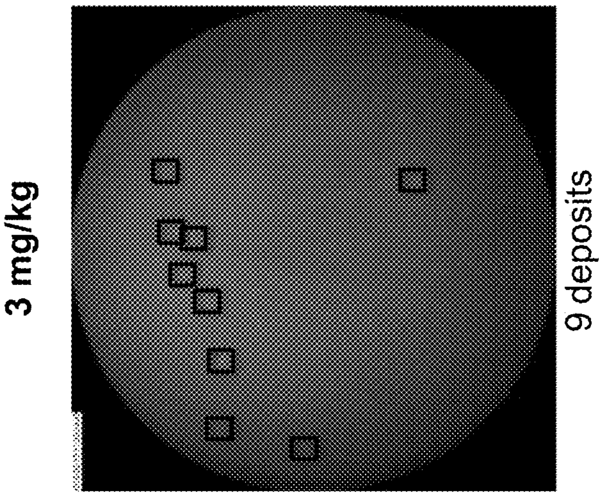
Figure 13:
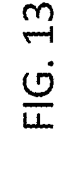

FIG. 13 shows that administration of Compound 10 can detect retinal α-syn deposits at a lower dose of 3 mg/kg.

Figure 14:
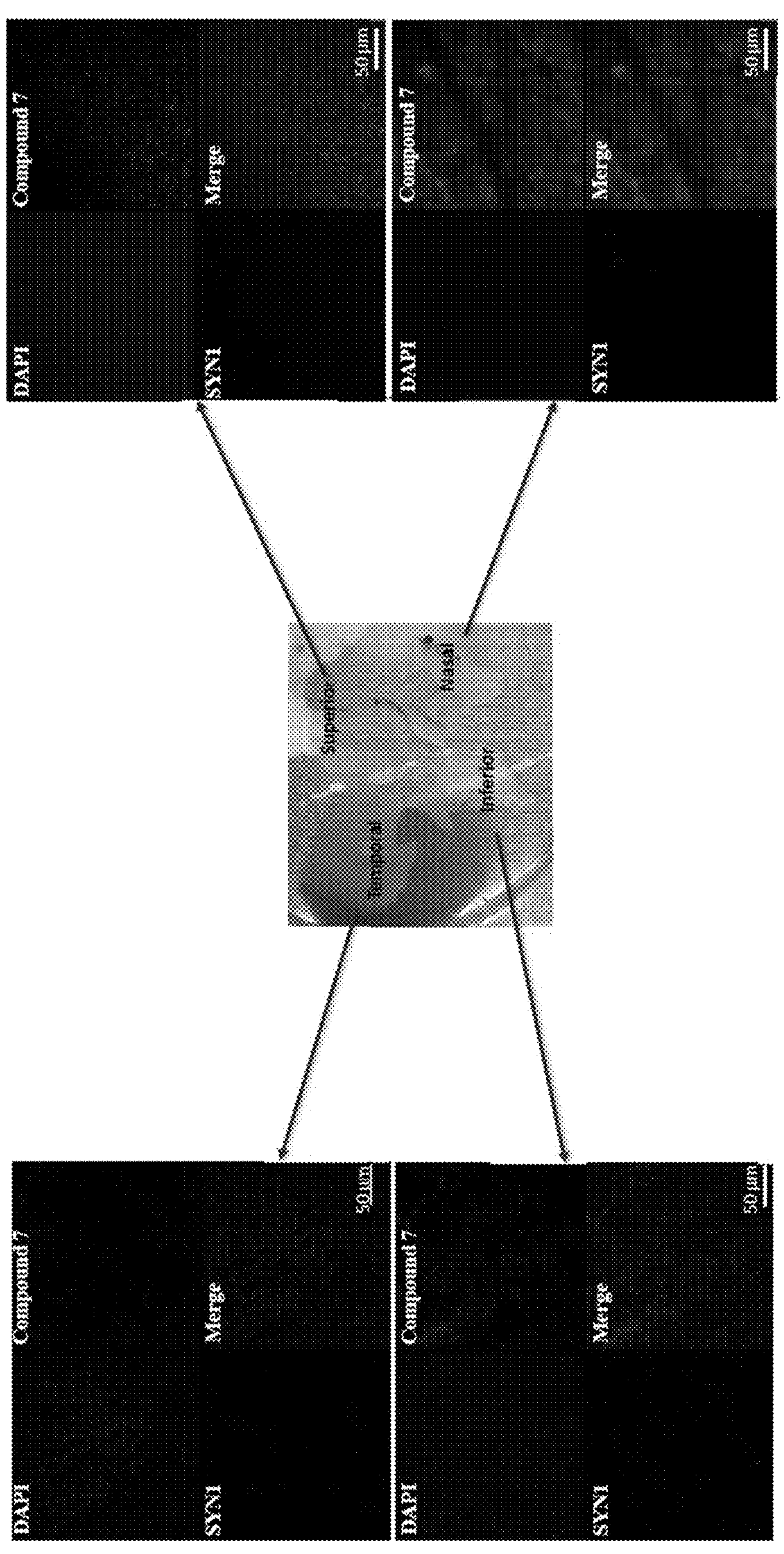

FIG. 14 shows example images from the right human healthy retina.

Figure 15:
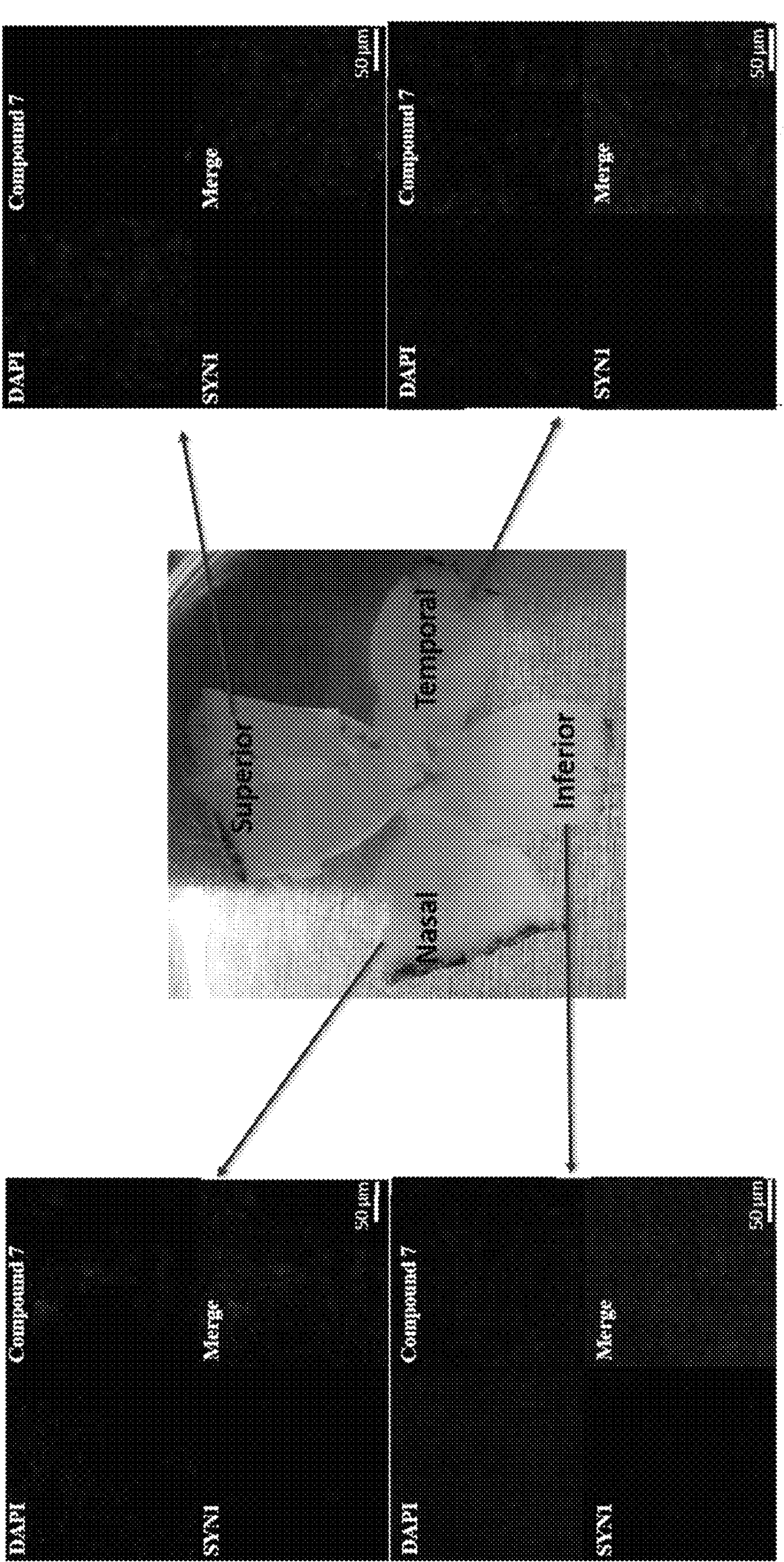

FIG. 15 shows example images from the left human healthy retina.

Figure 16:
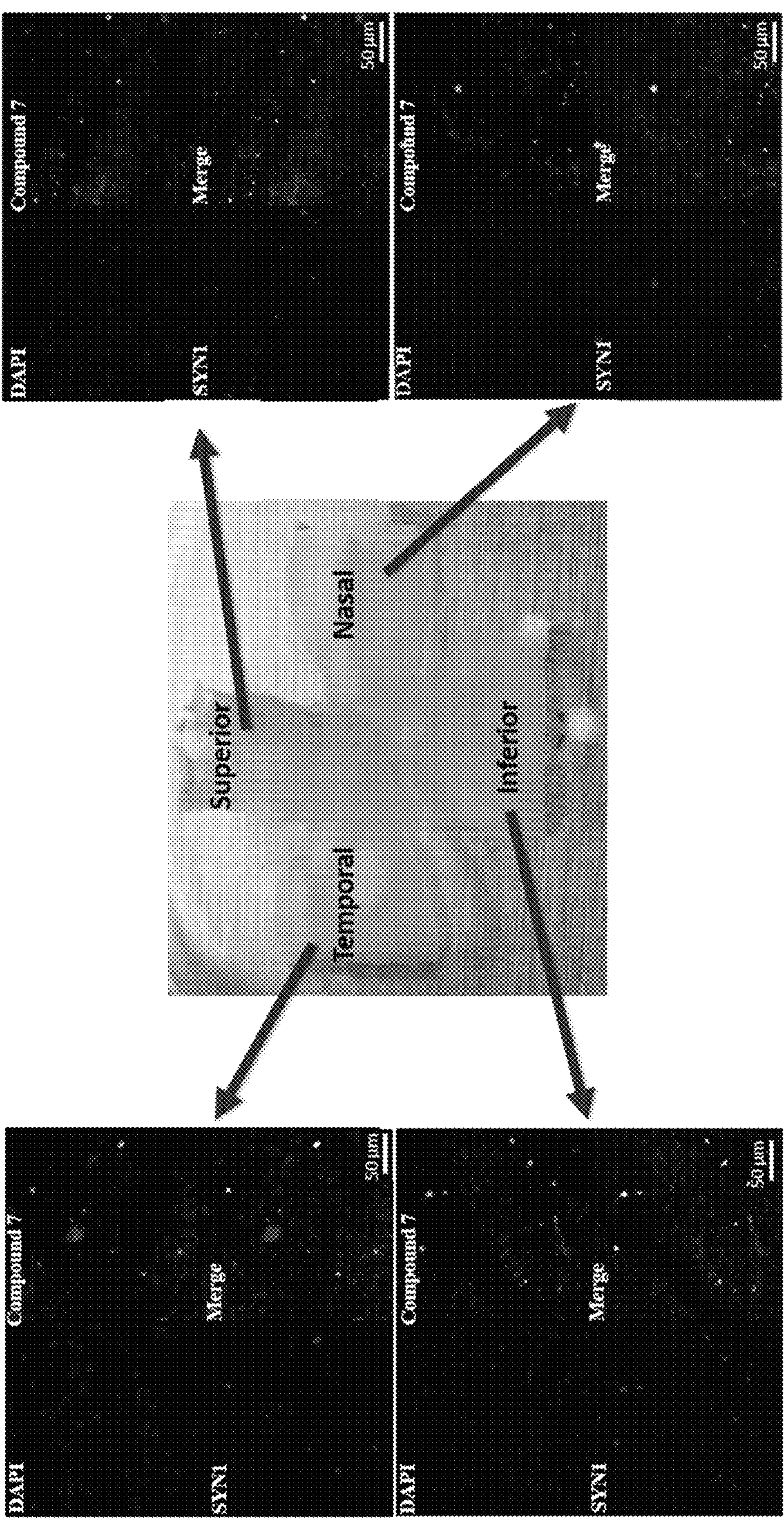

FIG. 16 shows example images from each region of the right retina extracted from a 71-year-old male diagnosed with Parkinson's disease (PD) stained with Compound 7 and SYN-1 Ab (alpha-synuclein).

Figure 17:
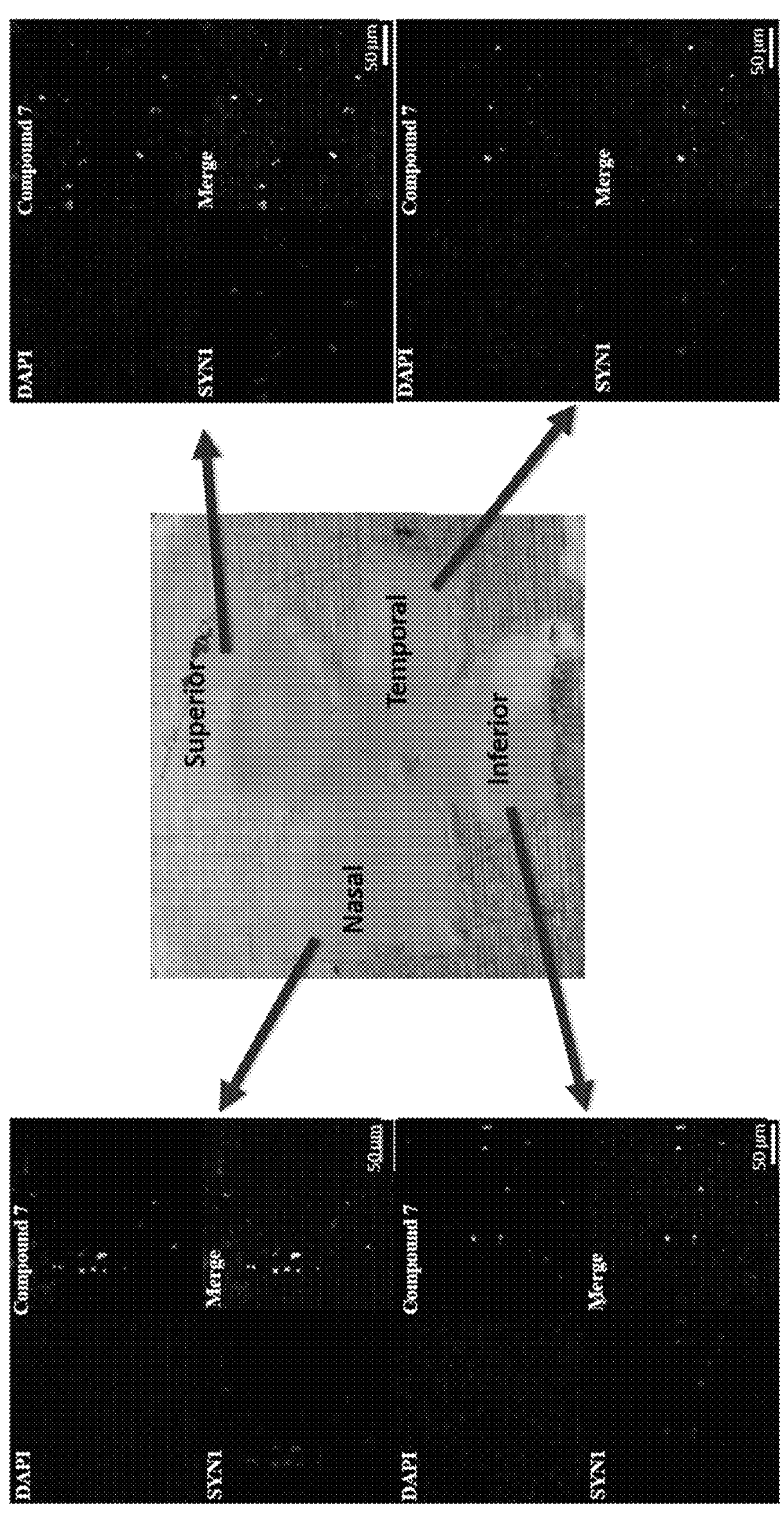

FIG. 17 shows example images from each region of the left retina extracted from a 71-year-old male diagnosed with Parkinson's disease (PD) stained with Compound 7 and SYN-1 Ab (alpha-synuclein).

Figure 18:
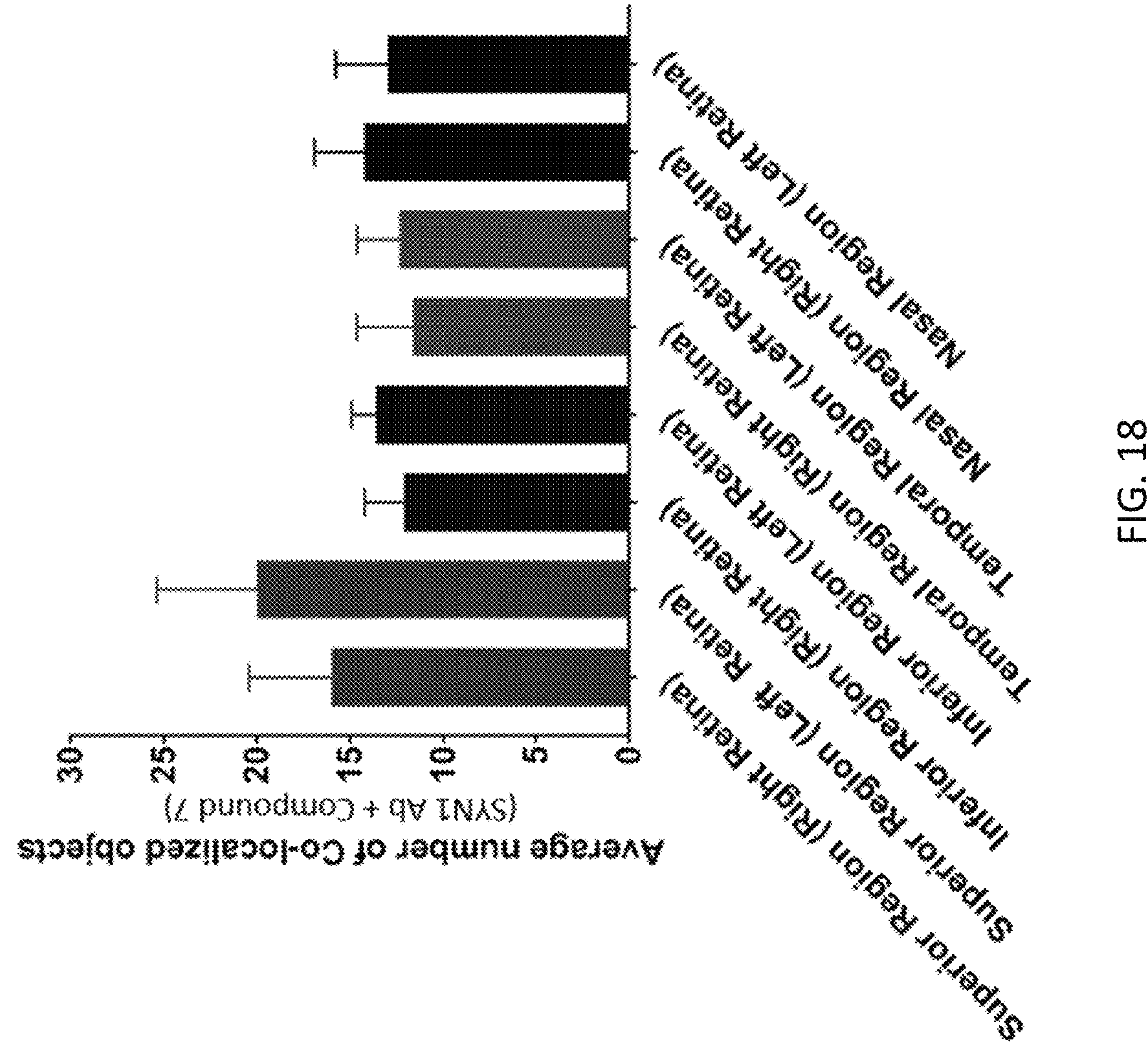

FIG. 18 shows that Compound 7 co-localizes with SYN1 in all four quadrants of a pair of Parkinson's Disease eyes.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash (e.g., "-" or "—") indicates a bond, which may be a point of attachment for a substituent. For example, —C(O)$NH_2$ is attached through the carbon atom. Chemical groups may be depicted with or without one or more dashes without losing their ordinary meaning. A wavy line drawn through a line in a structure indicates a point of attachment of a substituent or group.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl," by itself or as part of another substituent, represent a straight (i.e. unbranched) or branched chain, or combination thereof, which may be fully saturated, mono- or polyunsaturated and can include di- and multivalent radicals, having the number of carbon atoms designated (e.g., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like.

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Aryl" refers to an aromatic carbocyclic group having a single ring (e.g. monocyclic) or multiple rings (e.g. bicyclic or tricyclic) including fused systems. As used herein, aryl has 6 to ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" refers to —CN.

"Cycloalkyl" refers to a saturated or partially unsaturated cyclic alkyl, alkenyl, or alkynyl group having a single ring or multiple rings including fused, bridged, and spiro ring systems.

Cycloalkyl also refers to ring systems including multiple carbocyclic rings fused together wherein one of the fused rings is an aromatic ring but the ring system is not fully aromatic. As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, cyclohexyl, and cyclohexenyl.

The terms "halo" or "halogen," by themselves or as part of another substituent, mean, unless otherwise stated, a fluorine, chlorine, bromine, or iodine atom.

"Haloalkyl" refers to an unbranched or branched alkyl group as defined above, wherein one or more hydrogen atoms are replaced by a halogen. For example, where an alkyl residue is substituted with more than one halogen, it may be referred to by using a prefix corresponding to the number of halogen moieties attached. Dihaloalkyl and trihaloalkyl refer to alkyl substituted with two ("di") or three ("tri") halo groups, respectively, which may or may not be the same halogen. Examples of haloalkyl include, but are not limited to, difluoromethyl (—$CHF_2$), trifluoromethyl (—$CF_3$), fluoromethyl, 2,2,2-trifluoroethyl, 4-chlorobutyl, and 3-bromopropyl.

"Heteroalkyl," by itself or in combination with another term, means, unless otherwise stated, a straight or branched chain consisting of at least one carbon atom and at least one heteroatom selected from the group consisting of N, O, S, P, and Si, and wherein the N and S atoms may optionally be oxidized and the N may optionally be quaternized. The heteroatom(s) N, O, S, P, and Si, may be included at any non-terminal position of the heteroalkyl group or at the position at which the heteroalkyl group is attached. Two or more heteroatoms may be consecutive in the chain. Examples heteroalkyl include, but are not limited to, —$CH_2$—$CH_2$—O—$CH_3$, —$CH_2$—$CH_2$—O—$CH_2$—$CH_2$—O—$CH_3$, —$CH_2$—$CH_2$—O—$CH_2$—$CH_2$—O—$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH═CH—O—$CH_3$, —Si($CH_3$)$_3$, —$CH_2$═CH═N—$OCH_3$, —CH═CH—N($CH_3$)—$CH_3$, O—$CH_3$, and —O—$CH_2$—$CH_3$.

"Heteroaryl" refers to an aromatic group, including groups having an aromatic tautomer or resonance structure, having a single ring, multiple rings, or multiple fused rings, with one or more ring heteroatoms independently selected from N, O, and S, wherein the nitrogen and sulfur atoms are optionally oxidized, and the nitrogen atom(s) are optionally quaternized. As used herein, heteroaryl includes 3 to 20 ring atoms (i.e., 3- to 20-membered heteroaryl), 3 to 12 ring atoms (i.e., 3- to 12-membered heteroaryl), or 5 to 10 ring atoms (i.e., 5- to 10-membered heteroaryl), and 1 to 5 heteroatoms independently selected from N, O, and S. Heteroaryl does not encompass or overlap with aryl as defined above. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, triazolyl, 1,2,3-triazolyl, 1,2,4-triazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, pyridin-2(1H)-one, pyridazin-3(2H)-one, pyrimidin-4(3H)-one, quinolin-2(1H)-one, pyrimidinyl, purinyl, pyridyl, pyridazinyl, benzothiazolyl, and pyrazolyl. Substituents for each of the above noted aryl and heteroaryl ring systems are selected from the group of acceptable substituents described below.

The term "heterocyclyl" means a cyclic versions of "heteroalkyl." Additionally, for heterocyclyl, a heteroatom can occupy the position at which the heterocyclyl is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocyclyl include, but are not limited to, tetrahydropyran, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Examples of heterocyclyl include, but are not limited to glucose, mannose, allose, altrose, gulose, idose, galactose, and talose. Examples of heterocyclyl include, but are not limited to:

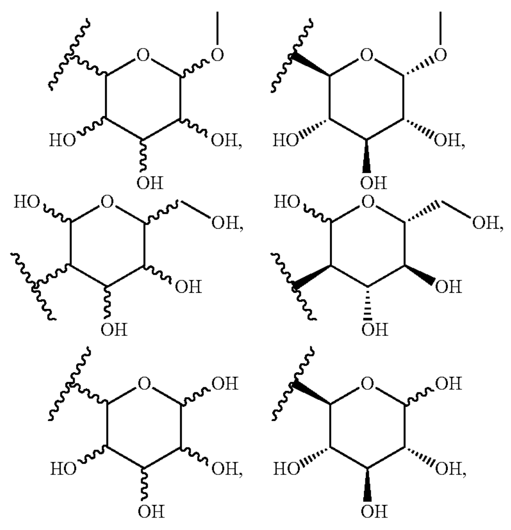

and the like.

"Hydroxyl" and "hydroxy" are used interchangeably and refer to —OH. "Oxo" refers to a double bonded O, written as, e.g., (═O) or (O). Where tautomeric forms of the compound exist, hydroxyl and oxo groups are interchangeable.

"Thiol" refers to —SH.

An "arylene" and a "heteroarylene," alone or as part of another substituent means a divalent radical derived from an aryl and heteroaryl, respectively.

Each of the above terms (e.g., "alkyl," "heteroalkyl," "aryl" and "heteroaryl") may include both substituted and unsubstituted forms of the indicated radical.

As used herein, the term "heteroatom" or "ring heteroatom" is meant to include oxygen (O), nitrogen (N), sulfur (S), phosphorus (P), and silicon (Si).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Some of the compounds exist as tautomers. Tautomers are in equilibrium with one another. For example, amide containing compounds may exist in equilibrium with imidic acid tautomers, and carbonyl containing compounds may exist in equilibrium with enol tautomers. Regardless of which tautomer is shown, and regardless of the nature of the equilibrium among tautomers, the compounds are understood by one of ordinary skill in the art to comprise all tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}A$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes deuterated analogs of compounds of Formula I in which from 1 to n hydrogens attached, e.g., to a carbon atom is/are replaced by deuterium, in which n is the number of hydrogens in the molecule. Such compounds may exhibit increased resistance to metabolism and may be useful for increasing the half-life of any compound of Formula I when administered to a mammal, particularly a human. See, for example, Foster, "Deuterium Isotope Effects in Studies of Drug Metabolism," Trends Pharmacol. Sci. 5(12): 524-527 (1984). Such compounds are synthesized by means well known in the art, for example by employing starting materials in which one or more hydrogens have been replaced by deuterium.

Deuterium labelled or substituted compounds of the disclosure may have improved DMPK (drug metabolism and pharmacokinetics) properties, relating to distribution, metabolism and excretion (ADME). Substitution with heavier isotopes such as deuterium may afford certain advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compounds described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In some embodiments, the compounds are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with organic acids. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., $HN(alkyl)_2$), trialkyl amines (i.e., $N(alkyl)_3$), alkenyl amines (i.e., $NH_2$(alkenyl)), dialkenyl amines (i.e., HN(alkenyl)$_2$), trialkenyl amines (i.e., N(alkenyl)$_3$), mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed alkyl, alkenyl, cycloalkyl, and/or aryl amines. Specific examples of suitable amines include, by way of example only, diisopropylamine, triethyl amine, diethyl amine, tri(iso-propyl) amine, tri(n-propyl)amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. Unless otherwise stated, the one or more substituents may be any substituent provided herein, or a combination thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the pharmaceutical compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

"Prodrug" refers to any compound that when administered to a biological system generates a parent compound, as a result of spontaneous chemical reaction(s), enzyme catalyzed chemical reaction(s), photolysis, and/or metabolic chemical reaction(s). A prodrug is thus a covalently modified analog or latent form of a biologically active parent compound. In some embodiments, the parent compound is Compound 7.

Compounds

The present disclosure provides compounds useful in the detection and treatment of neurological diseases and disorders. The compounds disclosed herein can be useful in detection of a disease or disorder in a patient, screening to identify patients at risk for the development of a disease or disorder, diagnosing a disease or disorder, or monitoring a disease or disorder. The compounds of the present disclosure may act as prodrugs and thus reference to a compound described herein is intended to include metabolites and parent compounds formed upon administration of the compound to the patient.

Due to the poor water solubility and the large particle size of compounds such as Compound 7, prodrug derivatives of these compounds were investigated. It was discovered that phosphate prodrugs of Compound 7 exhibited advantages in solubility and in reducing crystallinity. Specifically, water solubility was found to increase upon addition of a phosphate functional group to Compound 7. It was found that the phosphate functional group is cleaved in the body by phosphatases, resulting in delivery of the parent compound.

The compound may be a compound of formula I, or a pharmaceutically acceptable salt thereof:

I

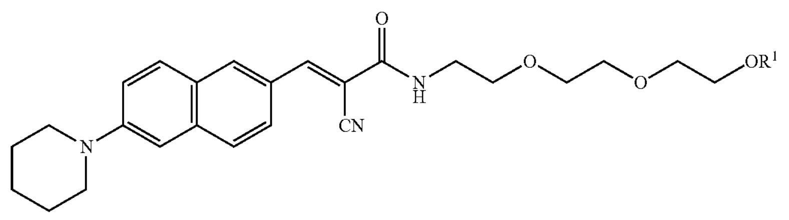

wherein $R^1$ is selected from

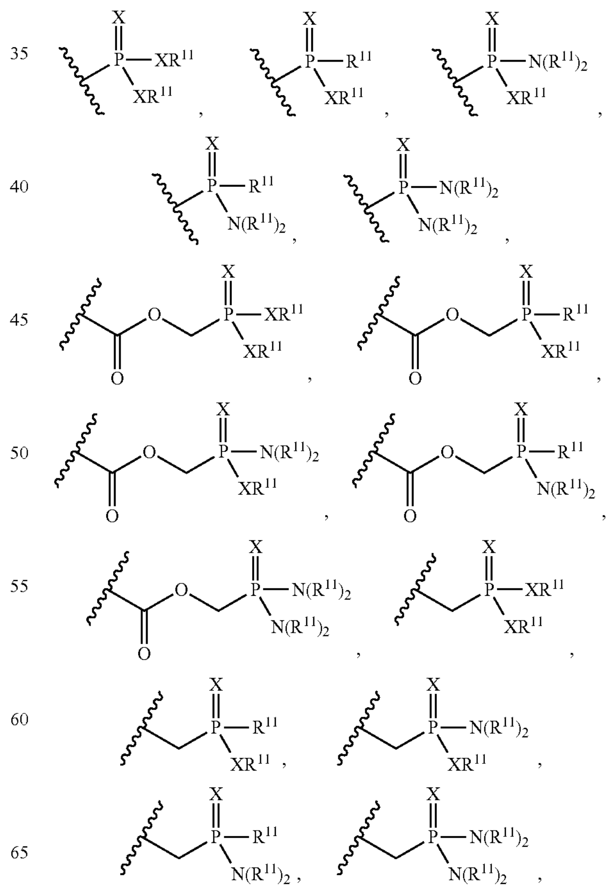

-continued

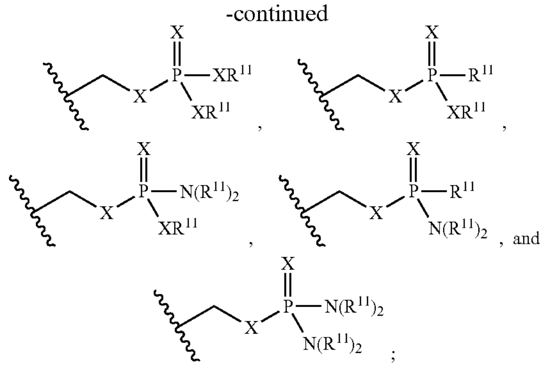

each X is independently O or S;

each $R^{11}$ is independently selected from hydrogen, $C_{1-10}$ alkyl, $C_{2-6}$ alkenyl, $C_{2-6}$ alkynyl, $C_{3-10}$ cycloalkyl, $C_{6-10}$ aryl, 5- to 10-membered heteroaryl and 4- to 10-membered heterocyclyl; wherein the alkyl, alkenyl, alkynyl, cycloalkyl, aryl, heteroaryl and heterocyclyl are optionally substituted with one to four $R^{21}$; or each $XR^{11}$ independently is —XP(X)$(R^{12})_2$;

each $R^{12}$ is independently selected from hydroxy, thiol, —XP(X)$(R^{13})_2$, $C_{1-10}$ alkyl, —O—$C_{1-10}$ alkyl, and —S—$C_{1-10}$ alkyl;

each R 13 is independently selected from hydroxy, thiol, $C_{1-10}$ alkyl, —O—$C_{1-10}$ alkyl, and —S—$C_{1-10}$ alkyl;

each $R^{21}$ is independently selected from halo, hydroxy, thiol, —$NO_2$, —$N_3$, cyano, $C_{1-10}$ alkyl, $C_{2-6}$ alkenyl, $C_{2-6}$ alkynyl, $C_{3-10}$ cycloalkyl, $C_{1-8}$ haloalkyl, $C_{6-10}$ aryl, 5- to 10-membered heteroaryl, 4- to 10-membered heterocyclyl, —O—$C_{1-10}$ alkyl, —O—$C_{2-6}$ alkenyl, —O—$C_{2-6}$ alkynyl, —O—$C_{3-10}$ cycloalkyl, —O—$C_{1-8}$ haloalkyl, —O-aryl, —O-heteroaryl, —O-heterocyclyl, —$NH_2$, —NH$(R^{31})$, —N$(R^{31})_2$, —C(O)$(R^{31})$, —C(O)O$(R^{31})$, —C(O)OH, —C(O)$NH_2$, —C(O)NH$(R^{31})$, —C(O)N$(R^{31})_2$, —NHC(O)$(R^{31})$, —NHC(O)O$(R^{31})$, —NHC(O)NH$(R^{31})$, —S$(R^{31})$, —NHS$(O)_y(R^{31})$, —N($C_{1-10}$ alkyl)S$(O)_y(R^{31})$, —S$(O)_y$N$(R^{31})_2$, —S(O)NH$(R^{31})$, and —S$(O)_y(R^{31})$;

each $R^{31}$ is independently selected from $C_{1-10}$ alkyl, $C_{2-6}$ alkenyl, $C_{2-6}$ alkynyl, $C_{3-10}$ cycloalkyl, $C_{1-8}$ haloalkyl, aryl, heteroaryl, and heterocyclyl; and each y is independently 1 or 2.

In some embodiments, $R^1$ is

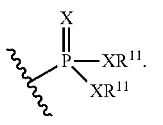

In some embodiments, each X is independently O.

In some embodiments, $R^1$ is

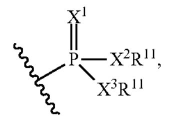

wherein each of $X^1$, $X^2$, and $X^3$ is independently O or S.

In some embodiments, $R^1$ is

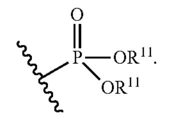

In some embodiments, each $R^{11}$ is independently hydrogen.

In some embodiments, $R^1$ is

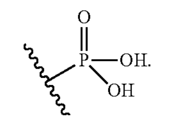 [SMILES: *P(=O)(O)O]

In some embodiments, the compound is a monobasic salt.

In some embodiments, the compound is a dibasic salt.

In some embodiments, the compound is a salt selected from sodium, potassium, lithium, ammonium, calcium, magnesium, or zinc salt.

In some embodiments, the compound is a sodium salt.

In some embodiments, the compound is a potassium salt.

In some embodiments, the compound is an ammonium salt. In some embodiments, the compound is a diammonium salt.

In some embodiments, the compound of formula I is

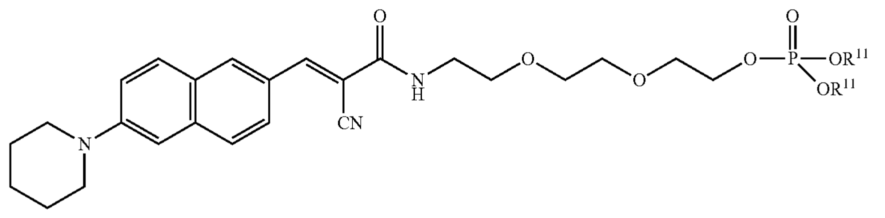

or a pharmaceutically acceptable salt thereof.

In some embodiments, the compound is Compound 7:

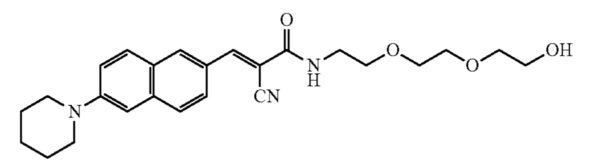 [SMILES: N#C/C(=C\c1ccc2cc(N3CCCCC3)ccc2c1)C(=O)NCCOCCOCCO]

or a pharmaceutically acceptable salt thereof.

In some embodiments, the compound is Compound 8:

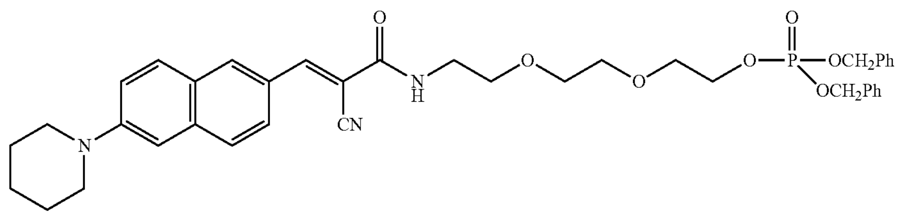

or a pharmaceutically acceptable salt thereof.

In some embodiments, the compound is Compound 9:

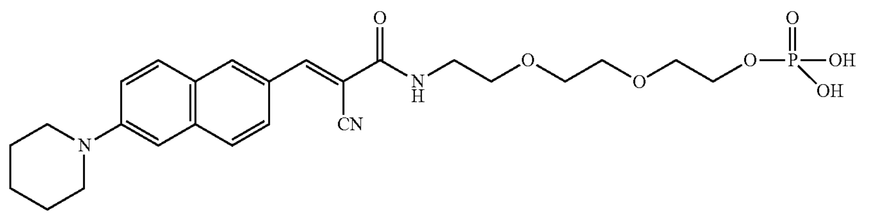 [SMILES: N#C/C(=C\c1ccc2cc(N3CCCCC3)ccc2c1)C(=O)NCCOCCOCCOP(=O)(O)O]

or a pharmaceutically acceptable salt thereof. In some embodiments, the salt is the diammonium salt. In some embodiments, the compound is Compound 10:

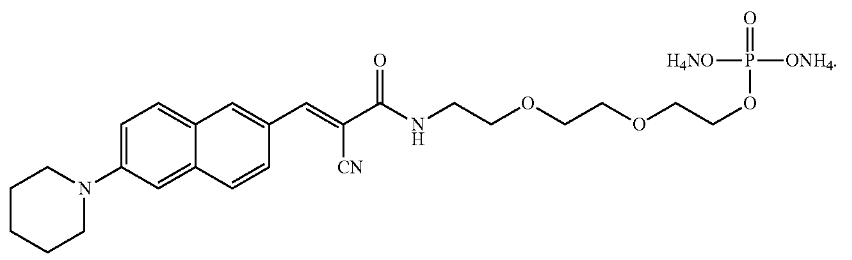

General Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of formula (I), e.g., compounds having structures described by, e.g., formula (I) or compounds disclosed herein, or a pharmaceutically acceptable salt thereof, may be accomplished as described in the examples and as known in the art.

Typical embodiments of compounds in accordance with the present disclosure may be synthesized using the reaction schemes and/or examples described below. It will be apparent given the description herein that the schemes may be altered by substitution of the materials with other materials having similar structures to result in products that are correspondingly different. Descriptions of syntheses follow to provide examples of how the steps may vary to provide desired products. Group labels (e.g., $R^1$) used in the reaction schemes herein are for illustrative purposes only and unless otherwise specified do not necessarily match by name or function the labels used elsewhere to describe compounds of formula (I), or aspects or fragments thereof.

It will be appreciated that where process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

The materials and reagents for the following reactions are generally known compounds or can be prepared by known procedures or obvious modifications thereof. For example, many of the starting materials are available from commercial suppliers such as Aldrich Chemical Co. (Milwaukee, Wisconsin, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

Scheme 1 shows an exemplary synthetic route for the synthesis of compounds provided herein (e.g., compounds of Formula I). The compounds of Formula I, e.g., compound 11, or other formulas or compounds disclosed herein, can be prepared by first providing compound 7 and then attaching the desired $R^1$ substituents using suitable conditions (e.g., nucleophilic displacement). In Scheme 1, $R^1$ is as defined herein, while Y is a suitable leaving group.

Scheme 1

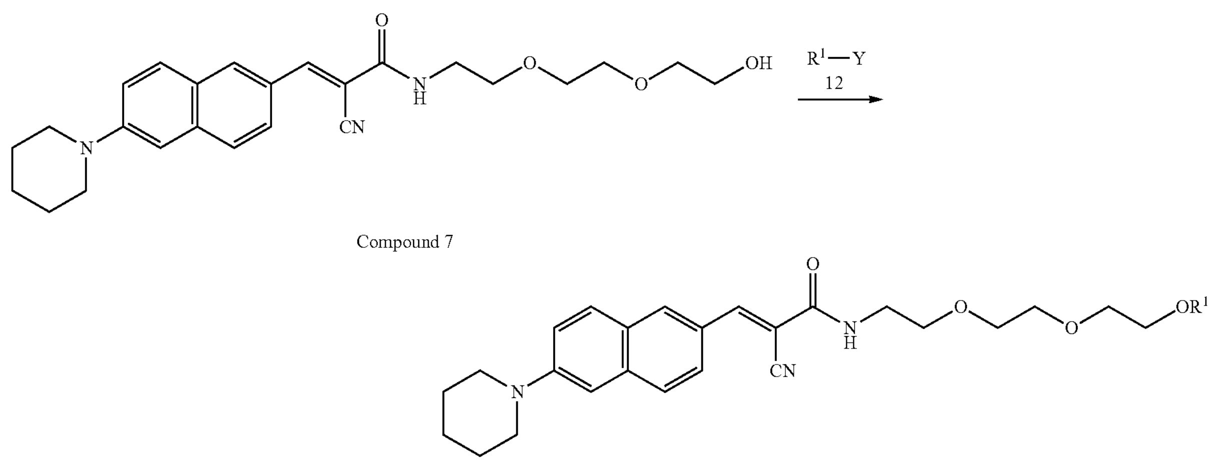

Compound 7

11

In Scheme 1, compound 7 is reacted with compound 12 under nucleophilic displacement conditions (e.g., using a base) in a suitable solvent (e.g., THF, DMF, etc.), optionally under an inert atmosphere, to provide compound 11. In some cases, compound 7 is deprotonated using a base, such as sodium hydride or butyllithium, and then contacted with compound 12. The reaction can be conducted at a temperature of about −78 to 0° C., for about 5 minutes to about 1 hour, or at a temperature of about 0 to 50° C., for about 1 hour to about 12 hours. When the reaction is substantially complete, the product compound 11 is isolated by conventional means.

Detectable Target Proteins

A compound described herein may be useful in detecting or treating a neurological disease or disorder. In this regard, a compound described herein may be a prodrug. Thus, a compound described herein may be converted to a parent compound through a chemical or enzymatic pathway, and the parent compound may in turn be useful in detecting or treating a neurological disease or disorder.

Many neurological diseases, including neurodegenerative diseases and injury-related disorders may be detected by the compounds and methods described herein. The neurological disease or disorder may be characterized by certain peptides, protein, or accumulated mass of protein, described herein as detectable proteins. The detectable protein, or the accumulated mass thereof, may comprise, for example, amyloid beta protein or phosphorylated tau protein. The amyloid beta protein or phosphorylated tau protein may be detected by contacting with a compound, as described herein. Generally, the compounds and methods described herein are useful for detection of amyloid beta protein or phosphorylated tau protein, or accumulated mass thereof, in a tissue or a sample of the patient. Such presence of amyloid beta protein or phosphorylated tau protein can be detected with compounds that bind to the amyloid beta protein or phosphorylated tau protein, which binding can then be detected.

Amyloid beta-protein (Aβ) is a polypeptide generally containing about 40 amino acid residues, e.g., about 36-43, about 39-43, or about 40-42 amino acid residues. Isoforms include Aβ(1-40) and Aβ(1-42). In some embodiments, the Aβ is Aβ(1-42). Aβ is believed to be produced by enzymatic cleavage of a larger precursor protein, beta-amyloid precursor protein (APP), which is encoded by a gene on human chromosome 21. APP isoforms include NP_000475.1, NP_001129488.1, NP_001129601.1, NP_001129602.1, NP_001129603.1, NP_001191230.1, NP_001191231.1, NP_001191232.1, NP_958816.1, and NP_9588171 Aβ is believed to be generated by action of the enzymes β and γ secretases on APP. Aβ has been found in deposits, e.g., plaques, in the brains of individuals having Alzheimer's disease. It is thought that Aβ is involved in the pathogenesis of neurological diseases. Aβ is also believed to be toxic to nerve cells.

The protein that is detected by a compound of the disclosure include amyloid beta peptide (Aβ), prion peptide (PrP), alpha-synuclein, IAPP (amylin), huntingtin, calcitonin (ACal), atrial natriuretic factor (AANF), apolipoprotein A1 (ApoA1), serum amyloid A (SAA), medin (AMed), prolactin (APro), transthyretin (ATTR), lysozyme (ALys), beta 2 microglobulin (Aβ2M), gelsolin (AGel), keratoepithelin (Aker), cystatin (ACys), immunoglobulin light chain AL (AL), S-IBM or superoxide dismutase. In some embodiments, the amyloid peptide detected is Aβ peptide, prion peptide, alpha-synuclein, or superoxide dismutase.

"Microtubule associated protein tau," "MAPT," "tau protein," or "tau" are a family of proteins which stabilize microtubules during assembly and disassembly, and are classified as microtubule-associated proteins (MAPs). Tau isoform sequences include NP_001116538.2, NP_001116539.1, NP_001190180.1, NP_001190181.1, NP_005901.2, NP_058518.1, NP_058519.3, and NP_058525.1. Tau proteins are important in the stabilization and assembly of microtubules, and in turn, affect the intra-neuronal transport of cargos. Tau may also be involved in signaling pathways by interacting with actin via acidic N-terminals, projecting from microtubules for neurite out-growth and stabilization during brain development. A tau protein as provided herein may comprise any isoform, or any combination of isoforms. MAPT transcripts are differentially expressed in the nervous system, depending on stage of neuronal maturation and neuron type. MAPT gene mutations have been associated with several neurological disorders such as Alzheimer's disease, Pick's disease, frontotemporal dementia, cortico-basal degeneration and progressive supranuclear palsy. The tau protein may or may not include post-translational modifications. The tau protein family is characterized by an N-terminal segment shared by all members, sequences of ~50 amino acids inserted in the N-terminal segment, which are developmentally regulated in the brain, a characteristic tandem repeat region consisting of 3 or 4 tandem repeats of 31-32 amino acids, and a C-terminal tail.

The human tau gene is located on the long arm of chromosome 17 at position 17q21. The gene is believed to contain 16 exons, with exon 21 as a part of the promoter. The tau primary transcript contains 13 exons, and exons 4A, 6 and 8 are not transcribed in human. Exons 21 and 14 are transcribed but not translated. Exons 1, 4, 5, 7, 9, 11, 12, 13 are constitutive, and exons 2, 3, and 10 are alternatively spliced, giving rise to six different mRNAs, translated in six different tau isoforms. These isoforms differ by the absence or presence of one or two 29 amino acid repeat (0N, 1N, or 2N) encoded by exon 2 and 3 in the amino-terminal part, in combination with either three microtubule binding repeats (R1, R3 and R4) or four (R1-R4) repeat-regions in the carboxy-terminal part. The fourth microtubule-binding domain is encoded by exon 10. Six tau protein isoforms are known to exist in human brain tissue: (2+3+10+) isoform (having 441-amino acids), (2+3+10−) isoform (having 410-amino acids), (2+3−10+) isoform (having 412-amino acids), (2+3−10−) isoform (having 381-amino acids), (2−3−10+) isoform (having 383-amino acids), and (2−3−10−) isoform (having 352-amino acids). The tau may be a mutant tau. The mutation may be a FTDP-17 mutation. Examples of mutations include G272V, N279K, N296, P201L, P301S, G303V, S305N, L315R, S320F, P332L, V337M, E342V, S352L, K369I, G389R, R5H, R5L, K257T, I260V, L266V, G272V, delK280, N296H, N296N, delN296, P301L, P301S, K317M, G335V, Q336R, R406W and R427M.

"Phosphorylated tau protein" or "phosphorylated tau" is a tau protein having at least one amino acid residue modified by a phosphate group. Tau is believed to include as many as 85 amino acid residues compatible with phosphorylation. Generally, the phosphate group is a post-translational modification and may be bonded at a side chain of an amino acid residue. The phosphorylated amino acid residue may be, for example, a serine (S), threonine (T), or tyrosine (Y) residue, or a combination thereof. A phosphorylated tau protein may include 1, 2, 3, 4, 5, 6, 7, 8, 9, 10, 11, 12, 13, 14, 15, 16, 17, 18, 19, 20, at least 20, at least 25, at least 30, at least 40, or at least 50 moles of phosphate per mole of protein. A phosphorylated tau protein may include at least 3 moles of phosphate per mole of protein. A phosphorylated tau protein may include one or more phosphorylated amino acid residues selected from Thr39, Ser46Pro, Thr50Pro, Thr69Pro, Thr153Pro, Thr175Pro, Thr181Pro, Ser198, Ser199, Ser202Pro, Thr205Pro, Ser208, Ser210, Thr212Pro, Ser214, Thr217Pro, Thr231Pro, Ser235Pro, Ser237, Ser241, Ser262, Ser285, Ser305, Ser324, Ser352, Ser356, Ser396Pro, Ser400, Thr403, Ser404Pro, Ser409, Ser412, Ser413, Ser416, and Ser422Pro. The phosphorylated tau protein may include phosphorylated Ser422. A phosphorylated tau protein as provided herein may be aggregated or may be unaggregated. A phosphorylated tau protein as provided herein may be soluble. A tau protein, or a phosphorylated tau protein, may be a three-repeat tau, a four-repeat tau, or a combination thereof. In some embodiments, a tau protein, or a phosphorylated tau protein, may comprise a mixture of three-repeat tau and four-repeat tau in which four-repeat tau is more prevalent. In some embodiments, a tau protein, or a phosphorylated tau protein, may comprise a mixture of three-repeat tau and four-repeat tau in which three-repeat tau is more prevalent. The phosphorylated tau protein may be fibrillary, for example as a neurofibrillary tangle (NFT). The NFT may be found in the somatodendritic compartments of neurons.

"Contacting" is used in accordance with its plain ordinary meaning and refers to the process of allowing at least two distinct species (e.g. chemical compounds including biomolecules, or cells) to become sufficiently proximal to interact. The term "contacting" may include allowing two molecular species to react or physically touch, wherein the two species may be, for example, a compound as described herein, a biomolecule, a protein or an enzyme. In some embodiments contacting includes allowing a compound described herein to interact with a protein (e.g., Aβ protein or a phosphorylated tau protein) or enzyme.

In accordance with some embodiments of the present disclosure, therefore, provided is a method for determining whether a patient has a neurological disease or disorder. The method entails detecting the presence of an amyloid beta-protein or a phosphorylated tau protein, or an accumulated mass thereof, in a tissue or a sample of the patient by contacting the tissue or sample of the patient with a compound described herein. The contacting may be in vivo or ex vivo. The contacting may be by administration, for example, topical or intravenous administration, of the compound to a patient.

In another embodiment, provided is a method for preparing a patient for diagnosis of a neurological disease or disorder, which method comprises administering to the patient a compound described herein, and binding to an amyloid beta-protein or a phosphorylated tau protein, or an accumulated mass thereof. The compound may be administered intravenously. Once the compound is administered to the patient, its binding, and/or the binding of a parent compound, to the amyloid beta-protein or phosphorylated tau protein, or accumulated mass thereof, may be detected with any method, including those methods described herein. In some embodiments, the binding indicates a likelihood that the patient has a neurological disease or disorder.

Neurological Diseases and Disorders and Treatment Thereof

In some embodiments, the disclosure provides a method of determining the presence or absence of a neurological disease or disorder in a patient. In some embodiments, the method comprises administering to the patient an effective amount of a compound described herein, or a pharmaceutical composition thereof. The compound may be a compound of Formula I. In some embodiments, the compound is Compound 7, Compound 8, or Compound 9. In some embodiments, the compound is Compound 7, Compound 8, Compound 9, or a pharmaceutically acceptable salt thereof. In some embodiments, the compound is Compound 10. In some embodiments, a method for determining whether a patient has a neurological disease or disorder is provided, comprising administering to the patient a compound described herein, or a pharmaceutical composition described herein. In some embodiments of the method, the compound is administered intravenously. In some embodiments of the method, the compound is administered to the eye of the patient. In some embodiments, the neurological disease or disorder is a disease or disorder characterized by protein aggregation or protein misfolding.

Also provided herein are methods for determining whether a patient has a neurological disease or disorder, comprising detecting the presence of an amyloid beta protein or a phosphorylated tau protein, or an accumulated mass thereof, in a tissue or a sample of the patient wherein the detecting comprises contacting the tissue or the sample with a compound described herein. The compound may be a compound of Formula I. In some embodiments, the compound is Compound 7, Compound 8, or Compound 9. In some embodiments, the compound is Compound 7, Compound 8, Compound 9, or a pharmaceutically acceptable salt thereof. In some embodiments, the compound is Compound 10. The contacting may be in vivo. The tissue may be an eye tissue. The sample may be a urine sample.

In some embodiments, the neurological disease or disorder is selected from an age-related disease or disorder, a genetic disease or disorder, an injury-related disease or disorder, and a psychiatric disease or disorder. In some embodiments, the age-related disease or disorder is selected from Parkinson's disease, vascular dementia, and Amyotrophic lateral sclerosis, the genetic disease or disorder is Down syndrome, the injury-related disease or disorder is selected from traumatic brain injury and chronic traumatic encephalopathy, and the psychiatric disease or disorder is selected from schizophrenia and depression. The neurological disease or disorder may be a tauopathy. In some embodiments, the neurological disease or disorder is Alzheimer's disease or traumatic brain injury (TBI).

The neurological disease or disorder may be a tauopathy. Tauopathies are a class of neurological diseases associated with the pathological aggregation of tau protein in neurofibrillary or gliofibrillary tangles in the human brain. Tangles may be formed by hyperphosphorylation of tau, causing the tau protein to dissociate from microtubules and form aggregates in an insoluble form. The aggregations of hyperphosphorylated tau protein may also be referred to as paired helical filaments. The precise mechanism of tangle formation is not completely understood, and it is still controversial as to whether tangles are a primary causative factor in the disease or play a more peripheral role. Tauopathy has been found in many neurological disorders, such as posttraumatic degeneration, infections, metabolic diseases, and motor neuron degeneration. The spatial distribution, temporal appearance, and structural changes of tau proteins manifest differently among various neurological diseases. AD patients have twisted, hyperphosphorylated, and single nonperiodical tau filaments, whereas patients having progressive supernuclear palsy and frontotemporal dementia (FTD) tend to have only straight tau filaments. Tauopathies are often overlapped with synucleinopathies, possibly due to interaction between the synuclein and tau proteins. Non-Alzheimer' s tauopathies are sometimes grouped together as "Pick's complex" due to their association with frontotemporal dementia, or frontotemporal lobar degeneration. A marker of tau hyperphosphorylation is tau pS422. Chronic traumatic encephalopathy (CTE) is associated with repetitive mild traumatic brain injury (mTBI), and bears many similarities with tauopathies, including hyperphosphorylation and aggregation of tau, for example, as neurofibrillary tangles (NFTs).

In some embodiments, the neurological disease or disorder is selected from primary age-related tauopathy (PART), neurofibrillary tangle-predominant senile dementia, chronic traumatic encephalopathy (CTE), progressive supranuclear palsy (PSP), corticobasal degeneration (CBD), frontotemporal dementia and parkinsonism linked to chromosome 17 (FTDP-17), Lytico-bodig disease (Parkinson-dementia complex of Guam), ganglioglioma, gangliocytoma, meningioangiomatosis, postencephalitic parkinsonism, subacute sclerosing panencephalitis (SSPE), lead encephalopathy, tuberous sclerosis, Pantothenate kinase-associated neurodegeneration, and lipofuscinosis.

The neurological disease or disorder may be a neurodegenerative disease or disorder. In some embodiments, the neurological disease or disorder is Alzheimer's disease (AD). AD may be classified as a secondary tauopathy. Alzheimer's disease is characterized by symptoms of memory loss in the early stages of the disease. Neurofibrillary tangles were an early descriptor of AD. When tau becomes hyperphosphorylated, the protein dissociates from the microtubules in axons. Then, tau may become misfolded and begin to aggregate, which may form neurofibrillary tangles (NFT). Microtubules also destabilize when tau is dissociated, and the combination of the neurofibrillary tangles and destabilized microtubules result in disruption of processes such as axonal transport and neural communication. The degree of NFT involvement in AD is defined by Braak stages. Braak stages I and II are used when NFT involvement is confined mainly to the transentorhinal region of the brain; stages III and IV when limbic regions such as the hippocampus become involved; stages V and VI when extensive neocortical involvement is indicated. AD is also classified as an amyloidosis because of the presence of senile plaques. Additionally, certain Apoε4 carriers are at greater risk of developing AD. APOε4 is believed to be less efficient than other isoforms at clearing Ac, and thus may be correlated with greater amyloid burden, tau phosphorylation, synaptotoxicity, and reduced synaptic density. Having experienced a traumatic brain injury (TBI) is another risk factor for developing AD, and studies indicate that those who experience a TBI have a significantly increased risk of AD.

As AD advances, symptoms include confusion, long-term memory loss, paraphasia, loss of vocabulary, aggression, irritability and/or mood swings. In more advanced stages of the disease, there is loss of bodily functions. Patients with Alzheimer's Disease (AD) demonstrate many characteristic neuropathies such as increased oxidative stress, mitochondrial dysfunction, synaptic dysfunction, disruption of calcium homeostasis, deposition of senile plaques and neurofibrillary tangles, and atrophy of the brain. AD related disorders include senile dementia of AD type (SDAT), frontotemporal dementia (FTD), vascular dementia, mild cognitive impairment (MCI) and age-associated memory impairment (AAMI). In some embodiments, determining whether a patient has Alzheimer's disease, comprising detecting the presence of a phosphorylated tau protein in a tissue or a sample of the patient, wherein the detecting comprises contacting the phosphorylated tau protein with a compound described herein.

In some embodiments, the neurological disease or disorder disease is frontotemporal lobar degeneration (FTLD) (e.g., FTLD-tau, FTLD-TDP, or FTLD-FUS). In some embodiments, the neurological disease or disorder is frontotemporal lobe dementia. In some embodiments, the neurological disease or disorder includes memory loss. In some embodiments, the neurological disease or disorder is age-related memory loss. In some embodiments, the neurological disease or disorder is FTLD-TDP Type A. In some embodiments, the neurological disease or disorder is FTLD-TDP Type B. In some embodiments, the neurological disease or disorder is FTLD-TDP Type C. In some embodiments, the neurological disease or disorder is FTLD-TDP Type D.

In some embodiments, the neurological disease or disorder is Parkinson's disease. In some embodiments, the neurological disease or disorder is Parkinson's dementia. In some embodiments, the neurological disease or disorder is related to (e.g. characterized by) an accumulated mass of amyloid plaques. In some embodiments, a patient having a neurological disease or disorder has suffered a traumatic brain injury before, during, or after the onset of the neurological disease or disorder. In some embodiments, the neurological disease or disorder includes a neuronal impairment. A neuronal impairment may include atrophy or other decrease in the effective functioning of the neuron. For example, it is known that Alzheimer's disease presents with neuronal impairment, especially in cortical neurons, e.g., hippocampal neurons and neurons in proximity to the hippocampus.

In some embodiments, the neurological disease or disorder is traumatic axonal injury (TAI), traumatic brain disorder (TBD), dementia (e.g., general dementia), frontotemporal dementia with parkinsonism linked to chromosome 17 (FTDP-17), primary age-related tauopathy (PART), neurofibrillary tangle-predominant senile dementia, progressive supranuclear palsy (PSP), corticobasal degeneration, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, pantothenate kinase-associated neurodegeneration, lipofuscinosis, Pick's disease, corticobasal degeneration, argyrophilic grain disease (AGD), or corticobasal degeneration.

The neurological disease or disorder may be an injury-related condition such as traumatic brain injury (TBI) or chronic traumatic encephalopathy (CTE). TBI is a chronic disease from damage to the brain caused by an external force, such as a bump, blow, jolt, rapid acceleration or deceleration, or penetration by a projectile. Injury leading to TBI may produce diminished or altered states of consciousness, resulting in temporary or permanent impairment in cognition, sensorimotor, and psychosocial function. CTE is a progressive degenerative disease found in people who have suffered repetitive brain trauma, including hits to the head that did not result in TBI symptoms. Physical aspects of CTE include shrinking of the brain, atrophy of the frontal and temporal lobes, enlargement of the ventricles, atrophy of the hippocampus, thalamus, brainstem and cerebellum. Individuals with CTE may have symptoms of dementia, memory loss, aggression, confusion, depression and suicidal ideations that may occur many years after the injuries.

The neurological disease or disorder may be of the eye, for example, glaucoma, ocular hypertension, macular degeneration, diabetic retinopathy, age-related macular degeneration (AMD) or retinitis pigmentosa.

In some embodiments of the method, the neurological disease or disorder is a prion disease. Prion diseases are fatal, transmissible, neurological disorders, the most prominent of which is Creutzfeldt-Jakob disease or CJD. CJD is sometimes called the "great mimicker" because it causes symptoms that occur in many other neurological diseases. Common CJD symptoms include different neurological and psychiatric indications, including behavioral changes, confusion, cognitive dysfunction, movement problems, and visual disturbances. CJD is difficult to diagnose, with current practices relying on cerebral spinal fluid tests. Interestingly, recent reports have indicated prion proteins in post-mortem retinal tissue of CJD patients.

Accordingly, provided is a method for detecting prion deposition in a patient. In certain embodiments, the detecting is performed in the retina. In certain embodiments, provided is a method for detecting prion deposition in the retina of a patient, wherein the patient may or may not exhibit clinical manifestations of a disease or disorder related thereto, such as Creutzfeldt-Jakob disease (e.g., behavioral changes, confusion, cognitive dysfunction, movement problems, visual disturbances, kyphosis, ataxia, tip toe walking, etc.).

Cerebral amyloid angiopathy (CAA) is a disease of aging characterized by amyloid deposition within cerebral blood vessel walls. These deposits develop in cortical and leptomeningeal arteries, leading to an increased risk of spontaneous intracerebral hemorrhage, ischemic lesions, and progressive dementia in the elderly population. The diagnosis of CAA is often missed by physicians as the presenting symptoms are those similar to a transient ischemic attack or "mini-stroke." Diagnosis can be further complicated as CAA is found in up to 90% of Alzheimer's disease patients. Several amyloid forming peptides can lead to CAA; among them, amyloid beta (Aβ) is by far the most prevalent form. Aβ deposition has been detected within the walls of arterioles, capillaries, and arteries of severe CAA human brain tissue. It has become established that the Aβ42 isoform is preferentially present in the parenchymal plaques of Alzheimer's patients while the Aβ40 isoform is denser within brain vascular wall depositions in CAA. In some embodiments of the method, the neurological disease or disorder is cerebral amyloid angiopathy (CAA). Cerebral amyloid angiopathy (CAA) is a disease of aging characterized by amyloid deposition within cerebral blood vessel walls.

Accordingly, in certain embodiments, provided is a method for detecting Aβ40 in a patient. In certain embodiments, the detecting is performed in the retina. In certain embodiments, the detecting differentiates between the Aβ isoforms associated with CAA (Aβ40) and Alzheimer's disease (Aβ42).

Additional examples of a neurological disease or disorder include Alexander's disease, Alper's disease, depression, perinatal asphyxia, Parkinson's disease dementia ("PD dementia"), amyotrophic lateral sclerosis, ataxia telangiectasia, Batten disease (also known as Spielmeyer-Vogt-Sjogren-Batten disease), spongiform encephalopathy (e.g., bovine spongiform encephalopathy (mad cow disease), Kuru, Creutzfeldt-Jakob disease, fatal familial insomnia, Canavan disease, Cockayne syndrome, corticobasal degeneration, fragile X syndrome, frontotemporal dementia, Gerstmann-Straussler-Scheinker syndrome, Huntington's disease, HIV-associated dementia, Kennedy's disease, Krabbe's disease, Lewy body dementia, Machado-Joseph disease (Spinocerebellar ataxia type 3), multiple sclerosis, multiple system atrophy, narcolepsy, neuroborreliosis, Pelizaeus-Merzbacher Disease, primary lateral sclerosis, prion diseases, Refsum's disease, Sandhoff s disease, Schilder's disease, subacute combined degeneration of spinal cord secondary to pernicious anaemia, schizophrenia, spinocerebellar ataxia (multiple types with varying characteristics), spinal muscular atrophy, Steele-Richardson-Olszewski disease, Tabes dorsalis, drug-induced Parkinsonism, progressive supranuclear palsy, corticobasal degeneration, multiple system atrophy, idiopathic Parkinson's disease, autosomal dominant Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK5), Parkinson disease 10 (PARK10), Parkinson disease 11 (PARK11), Parkinson disease 12 (PARK12), Parkinson disease 13 (PARK13), and mitochondrial Parkinson's disease.

Upon determination of a neurological disease or disorder in a patient, certain procedures can be provided to treat or ameliorate the symptoms of the neurological disease or disorder, or to slow or halt the progression thereof. Once a neurological disease or disorder is diagnosed, the progression of the disease or disorder may also be monitored by the methods described herein. Once diagnosed, the treating physician may also suggest additional treatments as known to practitioners, including those described herein.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) ameliorating, slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a patient (including a human) who is at risk or has a family history of the disease or condition.

"Patient" refers to an animal, such as a mammal (including a human), that has been or will be the object of diagnosis, treatment, observation or experiment. The methods described herein may be useful in human and/or veterinary applications. In some embodiments, the patient is a mammal. In one embodiment, the patient is a human.

The term "effective amount" of a compound described herein or a pharmaceutically acceptable salt, tautomer, stereoisomer, mixture of stereoisomers, prodrug, or deuterated analog thereof means an amount sufficient to detect an amyloid beta protein or phosphorylated tau protein, or an accumulated mass thereof, when administered to a patient or a sample of the patient, or to provide a therapeutic benefit such as amelioration of symptoms or slowing of disease progression. For example, an effective amount may be an amount sufficient to decrease a symptom of a disease or condition of a neurological disease or disorder. The effective amount may vary depending on the patient, and disease or condition being treated, the weight and age of the patient, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal dosing of administration of a compound of the present disclosure for a given indication, cell type, individual, and other parameters. Information gleaned from such use may be used for experimental purposes or in the clinic to set protocols for in vivo use. Other ex vivo uses for which the compounds and compositions described herein may be suited are described below or will become apparent to those skilled in the art. The selected compounds may be further characterized to examine the safety or tolerance dosage in human or non-human patients. Such properties may be examined using commonly known methods to those skilled in the art.

Detection of Target Protein

Provided herein are methods for diagnosis of a neurological disease or disorder in a patient, comprising administering to a tissue of the patient a compound described herein. The compound may be a compound of Formula I. In some embodiments, the compound is Compound 7, Compound 8, or Compound 9. In some embodiments, the compound is Compound 7, Compound 8, Compound 9, or a pharmaceutically acceptable salt thereof. In some embodiments, the compound is Compound 10. The method may comprise detecting a binding of the compound, and/or the binding of a parent compound, to a detectable target protein, for example, an amyloid beta protein, or a phosphorylated tau protein, or an accumulated mass thereof. The administration may be intravenous administration. The method may comprise detecting a binding of the compound to a detectable target protein. In some embodiments, the method further comprises activation by a light and emission of a detectable signal. In some embodiments, the method includes comparing the signal to a control value, wherein an increase in the signal compared to the control value indicates a presence of detectable target protein, where the control value is the signal in the absence of a detectable target protein. In some embodiments of the method, the detectable signal is a fluorescent or infrared signal. In some embodiments, the light is a laser.

In some embodiments, the disclosure provides a method of detecting a detectable target protein, for example, an amyloid beta protein, or a phosphorylated tau protein, or an accumulated mass thereof. The method comprises contacting a compound described herein with a tissue or a sample potentially comprising the detectable target protein, for example, an amyloid beta protein, or a phosphorylated tau protein, or an accumulated mass thereof, wherein the compound binds with the detectable target protein. In some embodiments, provided herein are methods of detecting the presence or absence of binding of a compound described herein, or a parent compound thereof, with a detectable target protein, comprising administering to a patient a compound, or a pharmaceutically acceptable salt thereof, as described herein. In some embodiments, provided herein are methods for monitoring the response of a patient having a disease or condition characterized by the presence of a detectable target protein to a treatment, comprising binding to the detectable target protein following the treatment an effective amount of a compound described herein, or a pharmaceutically acceptable salt thereof, and detecting a signal created in response to the binding, wherein a decrease of signal as compared to before the treatment indicates that the patient is responsive to the treatment. In some embodiments, the detectable target protein is an amyloid or amyloid like protein, for example, Aβ peptide, prion peptide, alpha-synuclein, or superoxide dismutase. In some embodiments, the amyloid or amyloid like protein is beta amyloid (1-42) (Aβ (1-42)). In some embodiments, the detectable target protein is a phosphorylated tau protein. In some embodiments, the phosphorylated tau protein is a three repeat tau or a four repeat tau.

In some embodiments, detection is performed within about 1 sec, about 5 sec, about 1 min, about 10 min, about 30 min or about 60 min of the contacting of the compound with the detectable target protein, or administration of the compound. In some embodiments, detection is performed within about 1-5 minutes of the contacting of the compound, or administration of the compound.

In situ detection of binding of detectable target protein, for example, an amyloid beta protein, or a phosphorylated tau protein, or an accumulated mass thereof, with a compound described herein, can be facilitated with an imaging device, which is preferably handheld or portable. The imaging device can include a lens and an image sensor, and optionally a laser light source. When the light source emits laser light to the tissue, for example, the retina, if detectable target protein is accumulated there and has bound to a compound described herein, the target protein can be readily detected and quantitated by the lens and image sensor that collects and senses a fluorescent signal. The imaging device may be any device capable of detecting light, for example, a camera. The imaging device may comprise a confocal lens. The imaging device may be a retinal imaging device. The imaging device may comprise a fundus camera. The detection may comprise confocal laser scanning microscopy. The detection may be non-mydriatic. For an overview of retinal imaging techniques, see, e.g., M. D. Abramoff et al, Retinal Imaging and Image Analysis (2010), IEEE Rev Biomed Eng. 3: 169-208.

The amyloid beta protein or phosphorylated tau protein may accumulate in an eye of the patient. In some embodiments, the contacting, upon activation by a light, causes emission of detectable signal. The signal may be a fluorescent or infrared signal.

Provided herein is a method for treating a neurological disease or disorder in a patient, comprising administering to the patient a compound described herein. The compound may be a compound of Formula I. In some embodiments, the compound is Compound 7, Compound 8, or Compound 9. In some embodiments, the compound is Compound 7, Compound 8, Compound 9, or a pharmaceutically acceptable salt thereof. In some embodiments, the compound is Compound 10.

Administration and Pharmaceutical Compositions

Also provided are pharmaceutical compositions of compounds described herein for administration to a patient. The compound may be a compound of Formula I. In some embodiments, the compound is Compound 7, Compound 8, or Compound 9. In some embodiments, the compound is Compound 7, Compound 8, Compound 9, or a pharmaceutically acceptable salt thereof. In some embodiments, the compound is Compound 10. The compound may be administered in either single or multiple doses. The compound may be administered by various methods including, for example, rectal, buccal, intranasal and transdermal routes. In certain embodiments, the compound may be administered by intra-arterial injection, intravenously, intraperitoneally, parenterally, intramuscularly, subcutaneously, orally, topically, or as an inhalant. In some embodiments, a compound described herein is administered intravenously. The intravenous administration can be bolus administration or continuous injection. Additional modes of injection include intraarterial, intracardiac, intrathecal, intraosseous, intraarticular, intrasynovial, intracutaneous, subcutaneous, intramuscular, and intradermal, intracranial, intralesional, and intratumoral.

In some embodiments, a compound described herein is administered to the eye. In some embodiments, the compounds are administered topically to the eye. In some embodiments, the administration is parenteral, for example, by injection. In some embodiments, a compound described herein is administered as a bolus injection, e.g., in arm. In some embodiments, the compounds are administered topically to the eye. In some embodiments, the administration is oral.

The compound may be effective over a wide dosage range. In some embodiments, the dose is from 0.01 to 1000 mg, from 0.5 to 100 mg, from 1 to 50 mg per day, or from 5 to 40 mg. Exemplary dosages include 10, 20, 30, 50, 75, 100, 200, 300, 400, 500, 600, 700, 800, 900, and 1000 mg. In some embodiments the effective amount of the compound corresponds to about 50 to 500 mg. An effective amount may vary between individual patients. The exact dosage will depend upon the route of administration, the form in which the compound is administered, the patient to be treated, the body weight or surface area of the patient to be treated, and the preference and experience of the attending physician.

In some embodiments the effective amount of the compound is about 0.01-1000 mg per dose. In some embodiments, the effective amount of compound is 50-500 mg per dose. In some embodiments the effective amount is about 0.01-100 mg, 0.01-200 mg, 0.01-300 mg, 0.01-400 mg, 0.01-500 mg, 0.01-600 mg, 0.01-700 mg, 0.01-800 mg, 0.01-900 mg, 0.01-1000 mg, 0.1-100 mg, 0.1-200 mg, 0.1-300 mg, 0.1-400, 0.1-500 mg, 0.1-600 mg, 0.1-700 mg, 0.1-800 mg, 0.1-900 mg, 0.1-1000 mg, 1-100 mg, 1-200 mg, 1-300 mg, 1-400 mg, 1-500 mg, 1-600 mg, 1-700 mg, 1-800 mg, 1-900 mg, 100-200 mg, 100-300 mg, 100-400 mg, 100-500 mg, 100-600 mg, 100-700 mg, 100-800 mg, 100-900 mg, 100-1000 mg, 200-300 mg, 200-400 mg, 200-500 mg, 200-600 mg, 200-700 mg, 200-800 mg, 200-900 mg, 200-1000 mg, 300-400 mg, 300-500 mg, 300-600 mg, 300-700 mg, 300-800 mg, 300-900 mg, 300-1000 mg, 400-500 mg, 400-600 mg, 400-700 mg, 400-800 mg, 400-900 mg, 400-1000 mg, 500-600 mg, 500-700 mg, 500-800 mg, 500-900 mg, 500-1000 mg, 600-700 mg, 600-800 mg, 600-900 mg, 600-1000 mg, 700-800 mg, 700-900 mg, 700-1000 mg, 800-900 mg, 800-1000 mg or about 900-1000 mg per dose. In some embodiments, the effective amount is about 50-100 mg, 50-400 mg, 50-500 mg, 100-200 mg, 100-300 mg, 100-400 mg, 100-500 mg, 200-300 mg, 200-400 mg, 200-500, 300-400 mg, 300-500 mg, or 400-500 mg per dose.

In some embodiments, the compound is administered in a single dose. In some embodiments, the compound is administered in multiple doses.

In some embodiments, the compound is administered in a pharmaceutical composition comprising a liquid carrier, for example, for intravenous administration. In some embodiments, the volume of pharmaceutical composition is from about 10 μL to about 1000 mL. For example the volume may be about 10 μL, 50 μL, 100 μL, 300 μL, 500 μL, 1 mL, 10 mL, 50 mL, 100 mL, 200 mL, 300 mL, 400 mL, 500 mL, 600 mL, 700 mL, 800 mL, 900 mL, or 1000 mL.

In some embodiments, the compound is administered as drops. In some embodiments, the size of the drop administered is in the range of about 10-100 μL, about 20-50 μL, or about 50-80 μL. In some embodiments, the drops are administered several drops per administration, for example 1-3 drops per time, 3-10 drops per time, or 7-10 drops per administration. In one example, the formulations of the disclosure are administered about one drop per time and 1-6 times per day.

In some embodiments, the compound described herein is formulated into a pharmaceutical composition. In some embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999). In some embodiments, a pharmaceutical composition is provided, comprising a compound described herein and a pharmaceutically acceptable carrier.

Provided herein are pharmaceutical compositions comprising a compound described herein and a pharmaceutically acceptable diluent, excipient, or carrier. The compound may be a compound of Formula I. In some embodiments, the compound is Compound 7, Compound 8, or Compound 9. In some embodiments, the compound is Compound 7, Compound 8, Compound 9, or a pharmaceutically acceptable salt thereof. In some embodiments, the compound is Compound 10. In some embodiments, the compound is administered as pharmaceutical compositions in which one or more compounds, are mixed with other active ingredients, as in combination therapy. In some embodiments, the pharmaceutical compositions include one or more compounds as described herein.

A pharmaceutical composition, as used herein, refers to a mixture of a compound described herein, with other chemical components, such as carriers, stabilizers, diluents, dispersing agents, suspending agents, thickening agents, and/or excipients. The pharmaceutical composition may facilitate administration of the compound to a patient. In some embodiments for practicing the methods of treatment or use provided herein, effective amounts of one or more compounds described herein are administered in a pharmaceutical composition to a patient having a disease or condition to be detected, diagnosed, or treated. In some embodiments, the patient is a human. An effective amount may vary depending on the severity of the disease, the age and relative health of the patient, the potency of the compound used and other factors. The compounds described herein are used singly or in combination with one or more diagnostic or therapeutic agents as components of mixtures.

For administration by injection, a compound described herein may be dispersed in a liquid pharmaceutically acceptable vehicle. The liquid pharmaceutically acceptable vehicle can be any aqueous or non-aqueous vehicle known in the art. Examples of aqueous vehicles include physiological saline solutions, solutions of sugars such as dextrose or mannitol, and pharmaceutically acceptable buffered solutions. In some embodiments, the aqueous vehicle is a physiologically compatible buffer, such as, for example, Hank's solution, Ringer's solution, aqueous acetate buffer, aqueous citrate buffer, aqueous carbonate buffer, aqueous phosphate buffer, aqueous succinate buffer, aqueous lactate buffer, or physiological saline buffer. Examples of non-aqueous vehicles include fixed vegetable oils, glycerin, polyethylene glycols, alcohols, and ethyl oleate. The vehicle may further include antibacterial preservatives, antioxidants, tonicity agents, buffers, stabilizers, surfactants, and other components. The pharmaceutical composition may comprise a cyclodextrin, for example, sulfobutylether β-cyclodextrin or hydroxypropyl β-cyclodextrin.

A pharmaceutical composition of a compound described herein may be for parenteral administration, for example, by injection. A compound for administration by injection may be prepared as, for example, an aqueous or oil suspension or emulsion in an injection medium. The injection medium may comprise castor oil (ricinus oil), castor oil (ethyoxylated), sesame oil, soybean oil, corn oil, cottonseed oil, or peanut oil, as well as elixirs, mannitol, dextrose, benzyl alcohol, PEG 400, ethylene glycol, polysorbate 20, diethylene glycol monoethyl ether, 10% aqueous poloxamer-188, glycerol, 10% aqueous poloxamer-407, or poloxamer 124.

In some embodiments, the pharmaceutical formulation comprises one or more surfactants. A surfactant is a material that is hydrophobic or amphiphilic (i.e., including both a hydrophilic and a hydrophobic component or region). Surfactants can be used to modify the surface properties of a particle and alter the way in which a particle is dispersed, emulsified, or suspended. In some embodiments, the surfactant comprises a lipid. Lipids that may be used include the following classes of lipids: fatty acids and derivatives, mono-, di- and triglycerides, phospholipids, sphingolipids, cholesterol and steroid derivatives, terpenes, prostaglandins and vitamins. Examples of fatty acids include lauric, physeteric, myristoleic, palmitoleic, petroselinic, and oleic acids, and mono, di- and triglycerides thereof. Such mono-, di-, and triglycerides include, for example, digalactosyldiglyceride, 1,2-dioleoyl-sn-glycerol, 1,2-dipalmitoyl-sn-3 succinylglycerol, and 1,3-dipalmitoyl-2-succinylglycerol. In some embodiments, the surfactant comprises a phospholipid. Phospholipids that may be used include phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Steroids which may be used include cholesterol, cholesterol sulfate, cholesterol hemisuccinate, 6-(5-cholesterol 3β-yloxy) hexyl-6-amino-6-deoxy-1-thio-α-D-galactopyranoside, 6-(5-cholesten-3β-yloxy)hexyl-6-amino-6-deoxy]-1-thio-α-D mannopyranoside, cholesteryl (4'-trimethylammonio)butanoate, and sodium deoxycholate (NaDOC). Surfactant products include Tween 20, Tween 80, and Neobee M-5.

Other surfactants include ethoxylated sorbitan esters, sorbitan esters, fatty acid salts, sugar esters, pluronics, tetronics, ethylene oxides, butylene oxides, propylene oxides, anionic surfactants, cationic surfactants, mono and diacyl glycerols, mono and diacyl ethylene glycols, mono and diacyl sorbitols, mono and diacyl glycerol succinates, alkyl acyl phosphatides, fatty alcohols, fatty amines and their salts, fatty ethers, fatty esters, fatty amides, fatty carbonates, cholesterol esters, cholesterol amides and cholesterol ethers, aluminum monostearate, ammonium lauryl sulfate, calcium stearate, dioctyl calcium sulfosuccinate, dioctyl potassium sulfosuccinate, dioctyl sodium sulfosuccinate, emulsifying wax, magnesium lauryl sulfate, potassium oleate, sodium caster oil, sodium cetostearyl sulfate, sodium lauryl ether sulfate, sodium lauryl sulfate, sodium lauryl sulfoacetate, sodium oleate, sodium stearate, sodium stearyl fumarate, sodium tetradecyl sulfate, zinc oleate, zinc stearate, benzalconium chloride, cetrimide, cetrimide bromide, and cetylpyridinium chloride.

Oral administration may be another route for administration of the compounds described herein. The pharmaceutical composition may bin the form of, for example, a capsule or an enteric coated tablet. A compound described herein may thus be diluted by an excipient and/or within a carrier. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients, carriers, and vehicles include lactose, dextrose, sucrose, sorbitol, mannitol, starches, gum acacia, calcium phosphate, alginates, tragacanth, gelatin, calcium silicate, microcrystalline cellulose, polyvinylpyrrolidone (PVP), cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

In some embodiments, the compounds described herein are formulated for ocular administration. In some embodiments, the ocular formulations is liquid (in form of solutions, suspensions, powder for reconstitution, sol to gel systems), semi solids (ointments and gels), solids (ocular inserts), and intraocular dosage forms (injections, irrigating solutions and implants).

Provided herein are ophthalmic formulations comprising the compounds described herein and an ophthalmologically acceptable component. The ophthalmic formulation may be administered in any form suitable for ocular drug administration, e.g., as a solution, suspension, ointment, gel, liposomal dispersion, colloidal microparticle suspension, or the like, or in an ocular insert, e.g., in an optionally biodegradable controlled release polymeric matrix.

By a "pharmaceutically acceptable" or "ophthalmologically acceptable" component is meant a component that is not biologically or otherwise undesirable, i.e., the component may be incorporated into an ophthalmic formulation of the disclosure and administered topically to a patient's eye without causing any undesirable biological effects or interacting in a deleterious manner with any of the other components of the formulation composition in which it is contained. When the term "pharmaceutically acceptable" is used to refer to a component other than a pharmacologically active agent, it is implied that the component has met the required standards of toxicological and manufacturing testing or that it is included on the Inactive Ingredient Guide prepared by the U.S. Food and Drug Administration.

Ophthalmic formulations may be adapted for topical administration to the eye in the form of a suspension or emulsion. The ophthalmic formulation may include an ophthalmologically acceptable carrier. Such carriers include, for example, water, mixtures of water, for example, phosphate buffer, boric acid, sodium chloride, and sodium borate, and water-miscible solvents such as lower alcohols, aryl alcohols, polyalkylene glycols, carboxymethylcellulose, polyvinylpyrrolidone, and isopropyl myristate. The ophthalmic formulation may also include one or more excipients such as emulsifying agents, preserving agents, wetting agents, bodying agents. For example, the ophthalmic formulation may include polyethylene glycols 200, 300, 400 and 600, carbowaxes 1,000, 1,500, 4,000, 6,000 and 10,000, antibacterial components such as quaternary ammonium compounds, phenylmercuric salts, thimerosal, methyl and propyl paraben, benzyl alcohol, phenyl ethanol, buffering agents such as sodium borate, sodium acetates, gluconate buffers, and other agents such as sorbitan monolaurate, triethanolamine, oleate, polyoxyethylene sorbitan monopalmitylate, dioctyl sodium sulfosuccinate, monothioglycerol, thiosorbitol, and ethylenediamine tetracetic acid. The ophthalmic formulation may be isotonic. The ophthalmic formulation may also include a surfactant or a stabilizer. Surfactants include Carbopol®. Stabilizers include sodium bisulfite, sodium metabisulfate and sodium thiosulfate.

The formulation may includes an effective amount of a permeation enhancer that facilitates penetration of the formulation components through cell membranes, tissues, and extra-cellular matrices, including the cornea. The "effective amount" of the permeation enhancer represents a concentration that is sufficient to provide a measurable increase in penetration of one or more of the formulation components through membranes, tissues, and extracellular matrices as just described. Suitable permeation enhancers include, by way of example, methyl sulfonylinethane (MSM; also referred to as methyl sulfone), combinations of MSM with dimethylsulfoxide (DMSO), or a combination of MSM and, in a less preferred embodiment, DMSO, with MSM particularly preferred.

Kits and Packages

Provided herein is a kit that includes a compound described herein, an imaging device, and optionally suitable packaging. The imaging device may be a retinal imaging device. In some embodiments, the kit further includes instructions for use.

The imaging device may include lens(es) and image sensors for detecting a signal emitted. In some embodiments, the imaging device detects a fluorescent signal. In some embodiments, the imaging device further includes a laser light source which can be used to activate the fluorescent signal. The imaging device may comprise a suitable retina scanner.

TABLE of Acronyms and Abbreviations

| Abbreviation | Meaning |
|---|---|
| Ac | Acetyl |
| Aq. | Aqueous |
| BINAP | (2,2'-bis(diphenylphosphino)-1,1'-binaphthyl) |
| Bn | Benzyl |
| br | Broad |
| d | Doublet |
| DCM | Dichloromethane/methylene chloride |
| dd | Doublet of doublets |
| DMF | Dimethylformamide |
| Equiv or eq | Equivalents |
| Et | Ethyl |
| EA | Ethyl acetate |
| EtOH | Ethanol |
| H or hr | Hours |
| Hz | Hertz |
| J | Coupling constant (MHz) |
| LCMS or LC-MS | Liquid chromatography-mass spectrometry |
| m | multiplet |
| M+ | Mass peak |
| M+H | Mass peak plus hydrogen |
| Me | Methyl |
| Min or m | Minute |
| MS | Mass spectroscopy |
| M/Z | Mass/Charge |
| N | Normal |
| ND | Not determined |
| NMR | Nuclear magnetic resonance |
| PCC | Pyridinium chlorochromate |
| Pd/C | Palladium on carbon |
| PE | Petroleum ether |
| Ph | Phenyl |
| pH | Expressing the acidity or alkalinity of a solution |
| prep | Preparative |
| PVP | Polyvinylpyrrolidone |
| Rf | Retention factor |
| RT or rt | Room temperature |
| s | Second |
| s | Singlet |
| sat. | Saturated |
| SGF | Simulated gastric fluid |
| t | Triplet |
| temp. | Temperature |
| THF | Tetrahydrofuran |
| TLC | Thin-layer chromatography |
| v/v or v/v/v | Volume ratio |
| δ | Chemical shift (ppm) |

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1

Based on preliminary rabbit pharmacokinetic studies with various formulations of the methyl ester derivative of Compound 7, studies to alter and improve certain physicochemical properties were undertaken. It was found that the hydroxy compound, i.e., Compound 7, exhibited fluorescent properties suitable for use with conventional instruments. Importantly, Compound 7 also demonstrated the ability to detect aggregated Aβ in vitro and ex vivo in human Alzheimer's brain tissue.

Synthesis

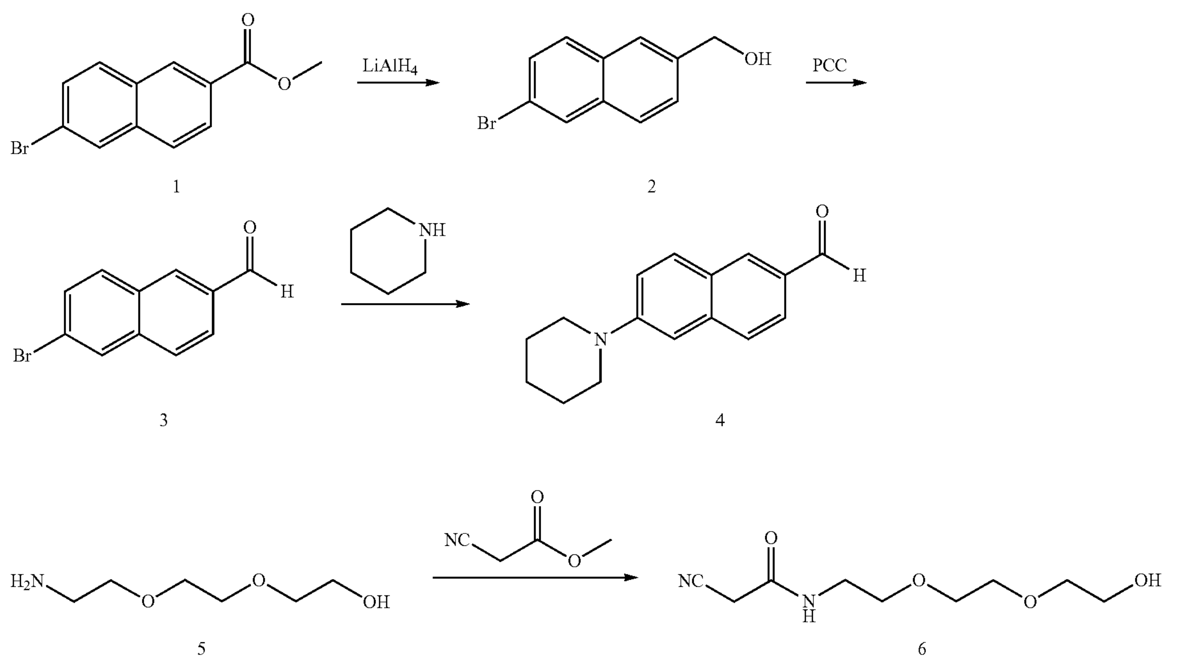

1

2

3

4

5

6

-continued

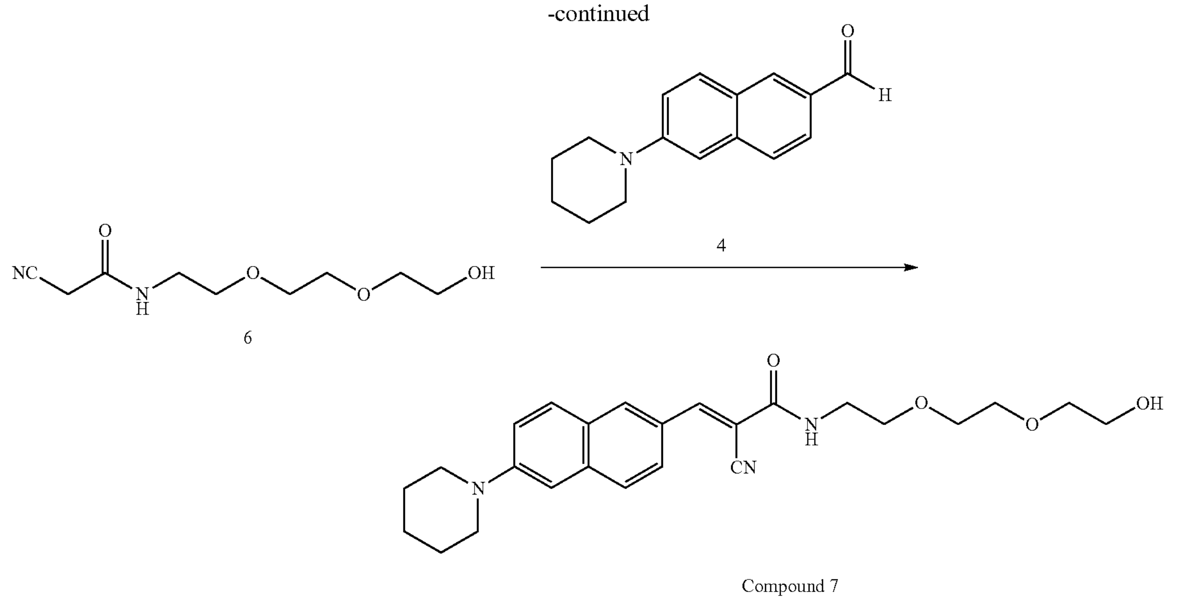

Compound 7

Synthesis of (6-bromonaphthalen-2-yl)methanol (2)

To a solution of $LiAlH_4$ (8.2 g, 217 mmol in 500 mL THF) at 0° C. under $N_2$, a solution of methyl 6-bromo-2-naphthoate (1) (50.0 g, 189 mmol) in 500 mL of anhydrous THF was added dropwise. The reaction mixture was left stirring for 1 h at 0° C. Upon reaction completion monitored by TLC, the mixture was treated with $H_2O$, 15% NaOH, $H_2O$ (1:1:3, v/v/v). After filtration, the filtrate was concentrated and extracted with EA, dried over $NaSO_4$. The crude product was purified from (PE:EA=3:1) to obtain the title compound.

Synthesis of 6-bromo-2-naphthaldehyde (3)

In a suspension of (6-bromonaphthalen-2-yl)methanol (2) (42.0 g, 177 mmol) and silica gel (76.4 g) in DCM (500 mL), was added PCC (76.4 g, 354 mmol). The reaction was stirred at RT (room temperature, 25±5° C.) for 1.5 h. Upon completion, it was filtered through a pad of silica and concentrated under reduced pressure to obtain the title compound.

Synthesis of 6-(piperidin-1-yl)-2-naphthaldehyde (4)

In dry and degassed toluene (300 mL), were added $Pd(OAc)_2$ (1.5 g, 6.3 mmol), BINAP (4.4 g, 7.1 mmol), 6-bromo-2-naphthaldehyde (3) (30.0 g, 127.8 mmol), $Cs_2CO_3$ (60.0 g, 183.9 mmol) and piperidine (12.7 g, 149.5 mmol). The reaction was left stirring for 8 h at 115° C. After cooling, the mixture was filtered and washed with EA, then concentrated to a third of the volume, to which was added 200 ml of 6 N hydrochloric acid with full stirring. Water phase was separated and extracted with DCM three times, then adjusted to alkaline with 5 N NaOH and extracted with EA. The organic phase was concentrated to yield crude material, which was further purified via silica gel chromatography (PE:EA=20:1 to 2:1) to obtain the title compound.

Synthesis of 2-cyano-N-(2-(2-(2-hydroxyethoxy) ethoxy)ethyl)acetamide (6)

In a pear-shaped flask, 5 (6.0 g, 40 mmol) was added to methyl 2-cyanoacetate (4.0 g, 40 mmol) with stirring. The mixture was let stirring overnight at RT and concentrated to a crude material. The crude material was directly used in the next step.

Synthesis of (E)-2-cyano-N-(2-(2-(2-hydroxyethoxy)ethoxy)ethyl)-3-(6-(piperidin-1-yl)naphthalen-2-yl)acrylamide (Compound 7)

To a solution of 6-(piperidin-1-yl)-2-naphthaldehyde (4) (7.0 g, 29.3 mmol) and 2-cyano-N-(2-(2-(2-hydroxyethoxy) ethoxy)ethyl)acetamide (6) (7.9 g, 36.5 mmol) in anhydrous THF (250 mL) was added piperidine (0.5 g, 5.9 mmol) and the resulting mixture was refluxed for 12 h. The reaction was then concentrated under reduced pressure to a crude material, which was purified via silica gel chromatography to obtain the title compound. Exact Mass 437.23; m/e 437.23 (100%), 438.23 (28.9%), 439.24 (4.7%); elemental analysis ($C_{25}H_{31}N_3O_4$): C, 68.63%; H, 7.14%; N, 9.60%; O, 14.63%.

Properties of Compound 7

The physical properties of Compound 7 were determined. Solubility of Compound 7 in various media is presented in Table 1.

TABLE 1

Compound 7 solubility

| Solvent | Solubility (mg/mL) |
|---|---|
| water | 0.0017 |
| SGF | 3.6 |
| pH 4.0 buffer | 0.070 |
| pH 7.0 buffer | 0.0046 |
| pH 7.4 buffer | 0.0033 |
| pH 9.0 buffer | 0.0048 |
| n-octanol | >8.0 |
| Castor Oil | >9.0 |

Due to the poor water solubility (Table 1), a possible nanosuspension formulation was explored. The purpose was to target a mean particle size of <0.5 μm. Data regarding particle size of Compound 7 in suspension formulation is presented in Table 2.

TABLE 2

| Particle size of Compound 7 in suspension formulation (NaDOC = sodium deoxycholate) | |
|---|---|
| Excipients | Mean Particle Size (μm) |
| 3% Compound 7, 0.6% PVP K12, 0.03% NaDOC | 21.3 ± 8.79 |
| 3% Compound 7, 0.6% Poloxamer 188, 0.03% NaDOC | 24.2 ± 0.76 |
| 3% Compound 7, 0.3% Tween 80 | 31.9 ± 10.28 |

Example 2

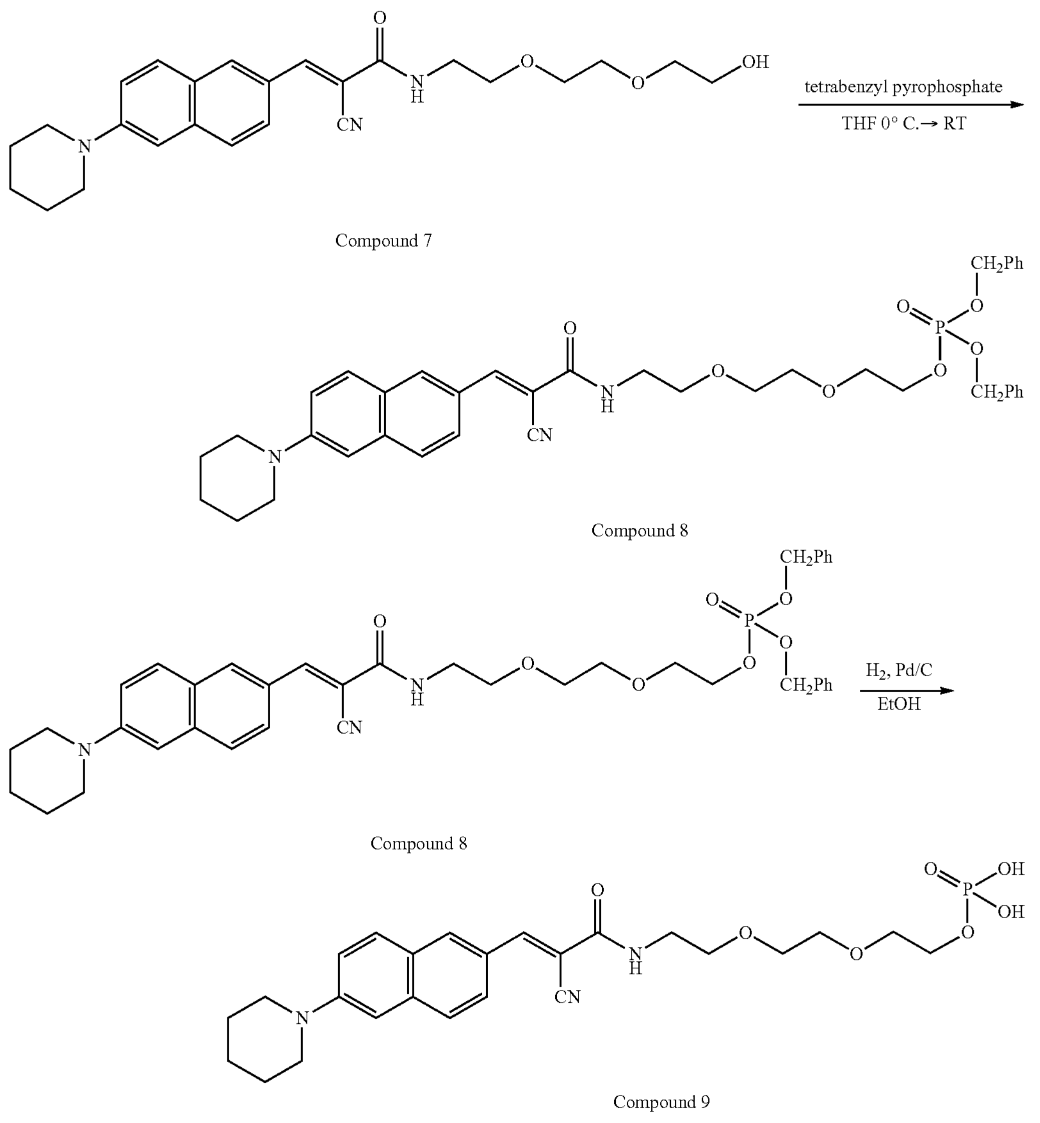

Compound 7

Compound 8

Compound 8

Compound 9

Synthesis of Compound 8

Attempts to prepare Compound 9 using traditional methods, such as POC13 and base such as triethylamine, proved unsuccessful. Due to the high reactivity of certain functional groups present on Compound 7, such as the NH amide which was found to react negatively with POC13, alternative synthetic routes were required. Other bases, such as LDA and LiHMDS, gave a mixture of products by TLC, which products were not isolated. It was determined that tetrabenzyl pyrophosphate with sodium hydride provided Compound 8. Compound 8 was prepared according to the following procedure.

Figure 1A:
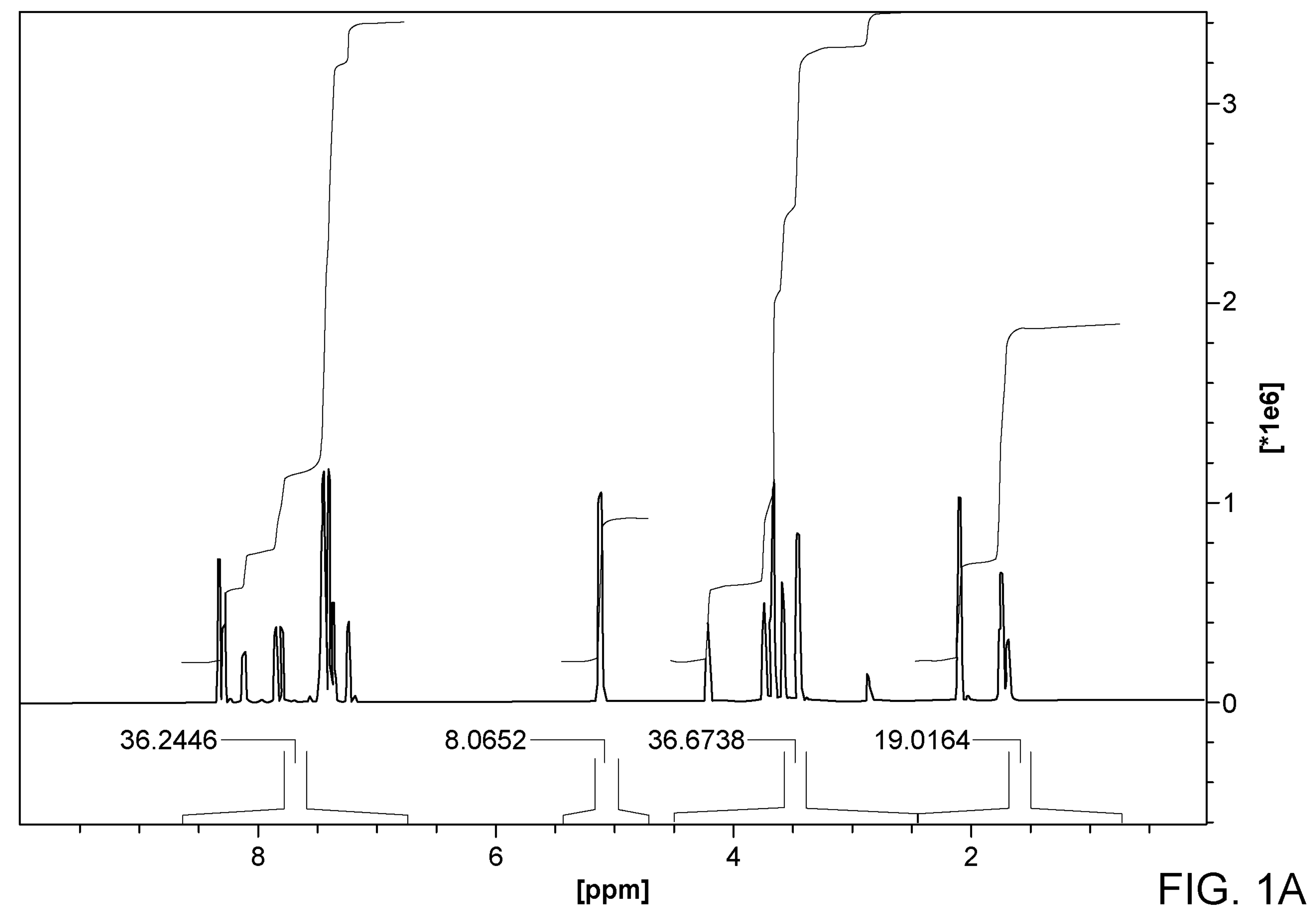
FIGS. 1A-1C illustrate a $^{1}$H NMR spectrum for Compound 8.
Figure 1B:
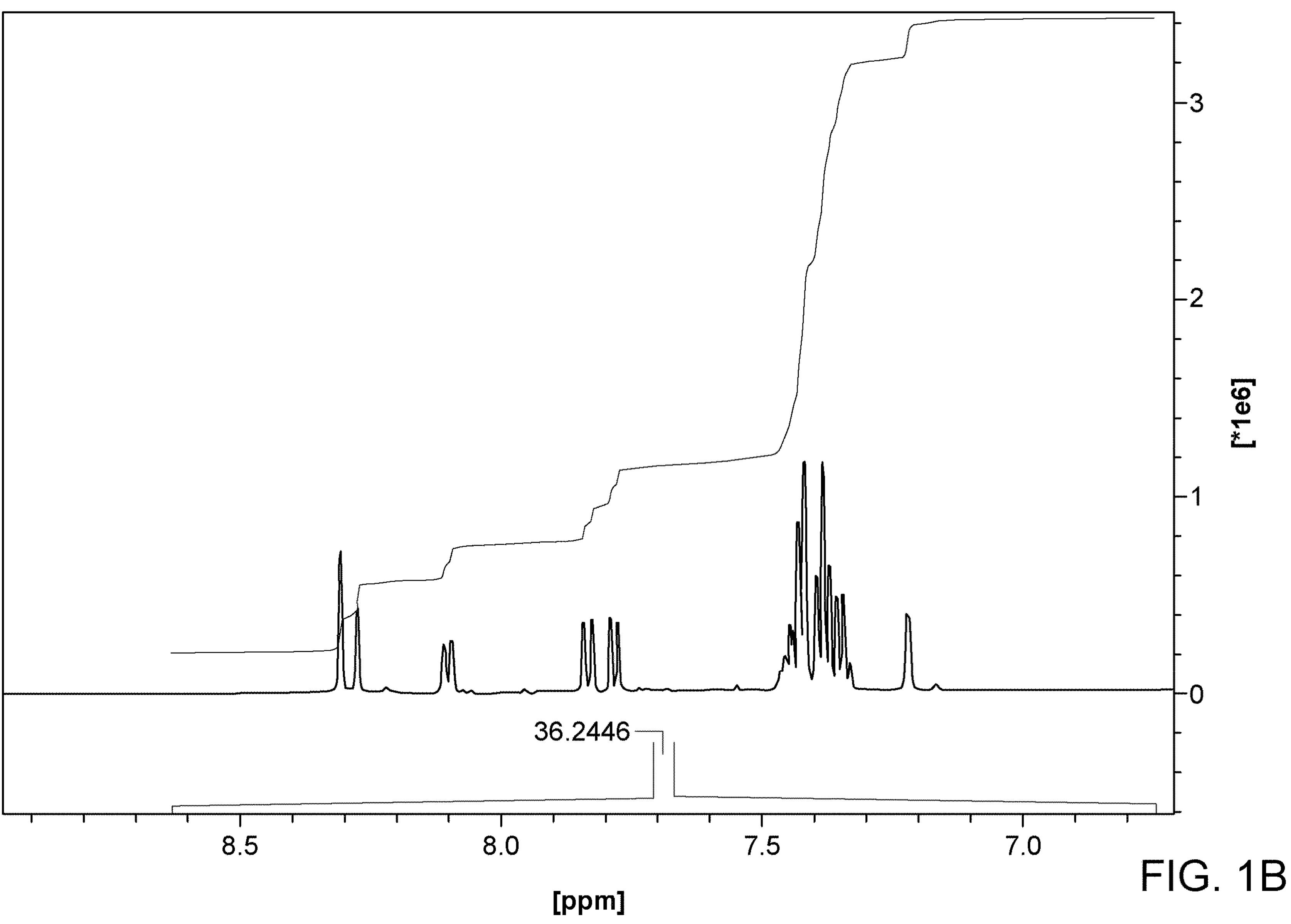
Figure 1C:
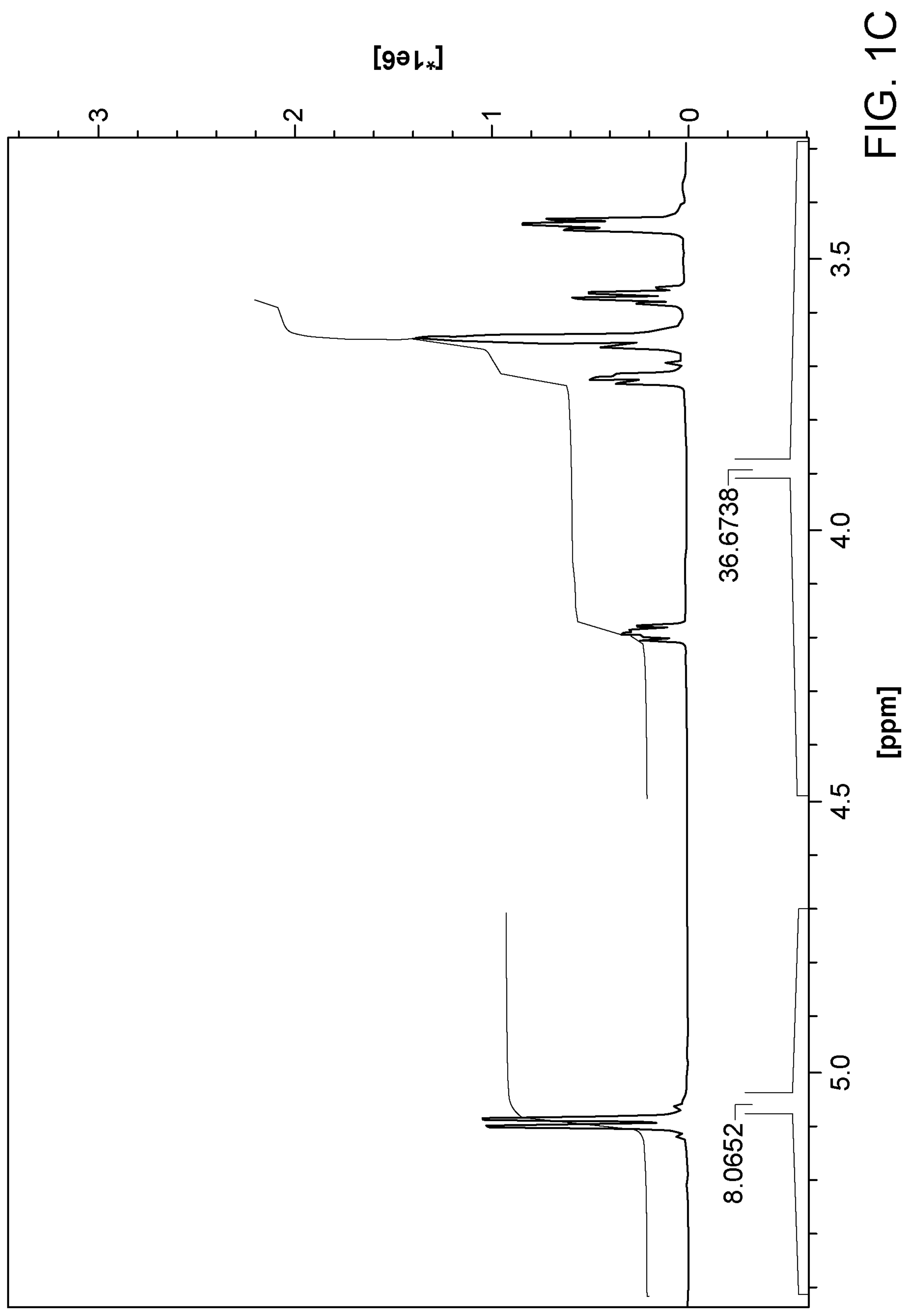

To 1 g (2.3 mM) of Compound 7 in 15 mL of THF at zero degrees was added 1.6 g (3 mM) of tetrabenzyl pyrophosphate prepared using Merck Organic Synthesis preparation, resulting in a deep red solution. Sodium hydride (100 mg, 2.5 mM, 60% in oil) was added. After min and warming to room temperature a solid started precipitating. DMF (5 mL) was added and stirred at RT for 1 hr. Water (200 mL) and ethyl acetate (200 mL) were added. The ethyl acetate layer was dried and evaporated. Purification by ISCO® on an 80 g silica gel cartridge using 0-100% hexane/ethyl acetate afforded the title compound. A $^{1}H$ NMR spectrum of Compound 8 is presented in FIGS. 1A to 1C. MS (m/z) 701.3 $[M+H]^+$.

Synthesis of Compound 9

Figure 2A:
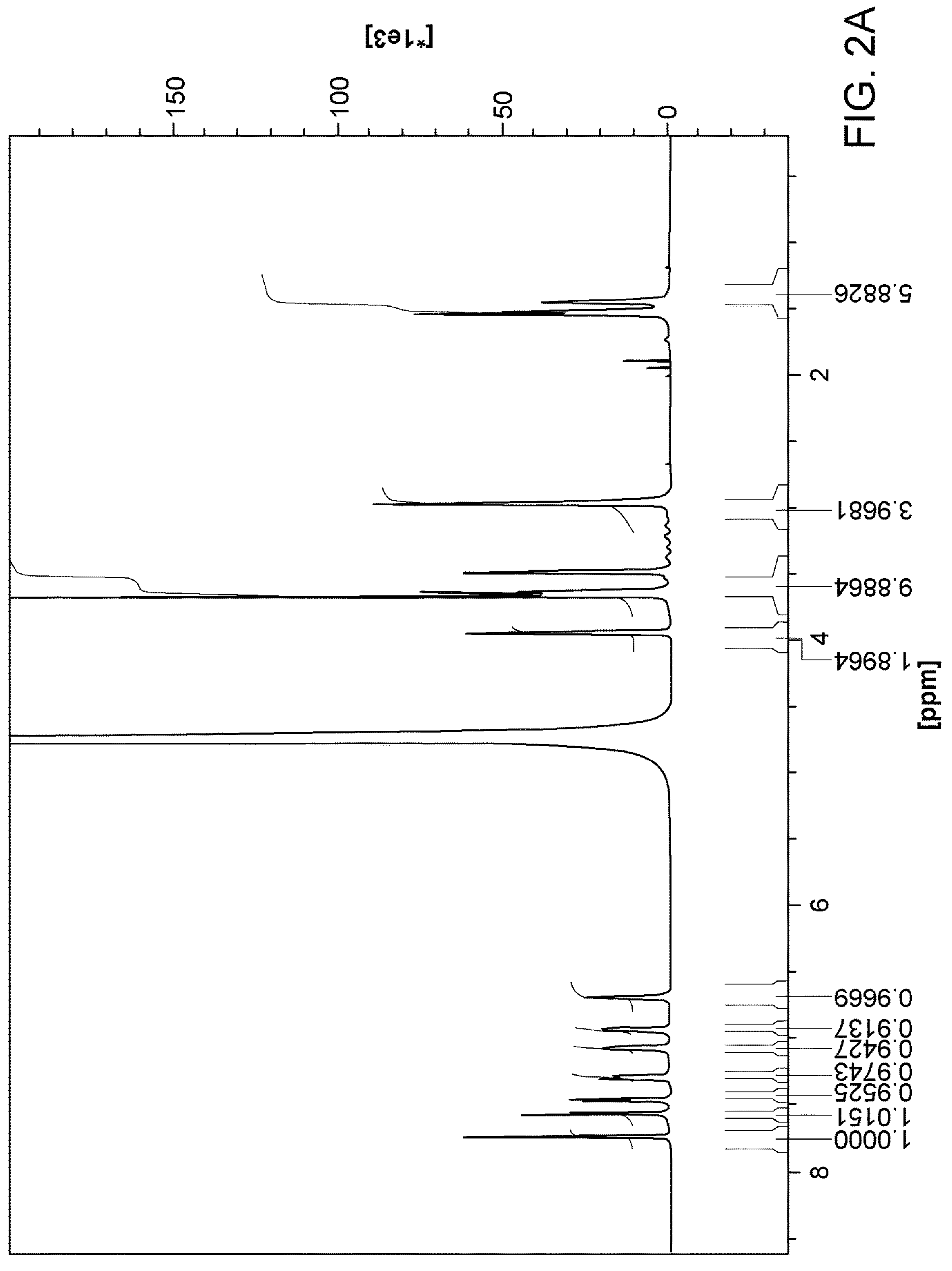
FIGS. 2A-2B illustrate a $^{1}$H NMR spectrum for Compound 9.
Figure 2B:
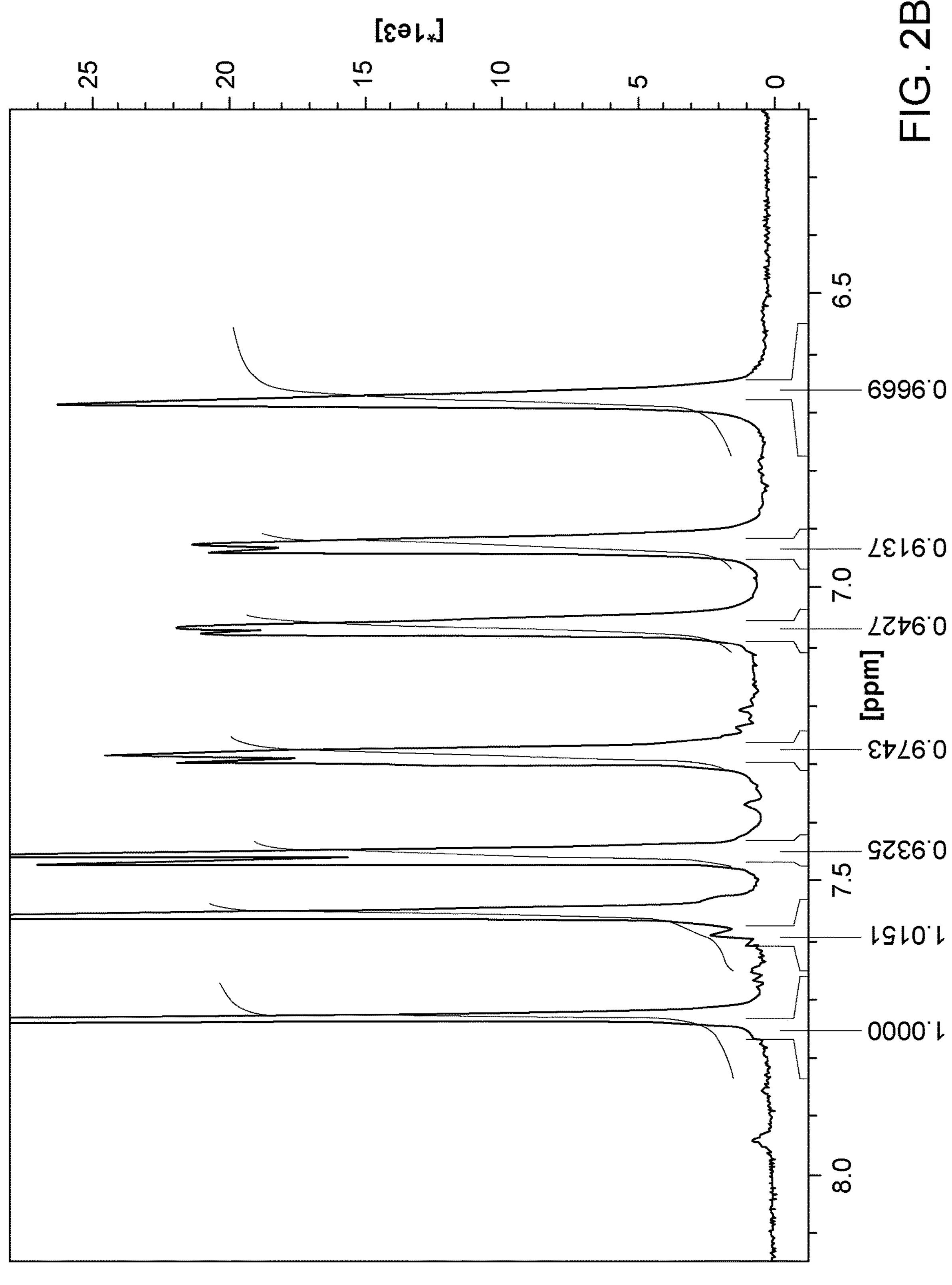

To 1 gram of (Compound 8), 95% ethanol (150 mL), degassed with argon was added. 120 mg of 10% Pd/C was added and hydrogen gas was bubbled into reaction mixture for 5 min. The mixture was then stirred under a hydrogen balloon for 3 hrs. Reaction mixture was degassed with argon and evaporated. Purification by prep LC/MS on a C18 column 25×250 mm using 0 to 100% water containing 2 g per liter ammonium acetate. After free drying, Compound 9 was obtained. A $^{1}H$ NMR spectrum (D20) of Compound 9 is presented in FIG. 2A and FIG. 2B.

It was found that the above synthesis using hydrogenation with hydrogen gas yields side products via, e.g., reduction of the double bond. This reduction results in long and tedious purification by HPLC.

Synthesis of Compound 9 Diammonium Salt (Also Referred to as Compound 10)

It was discovered that using trimethylsilyl bromide at zero degrees for a short time diminished the side reactions and the need for chromatography.

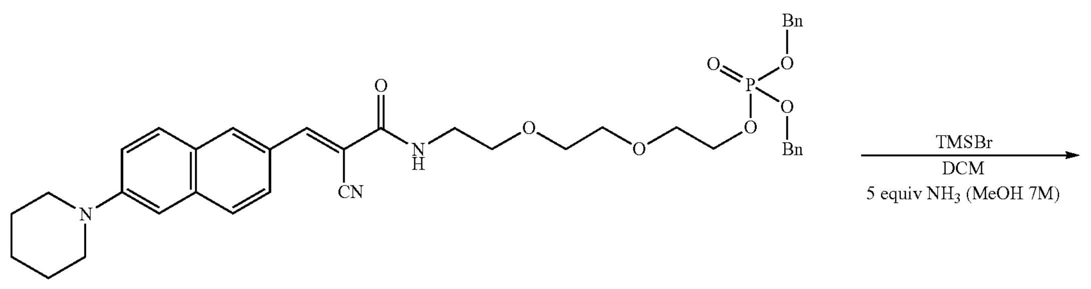

Compound 8

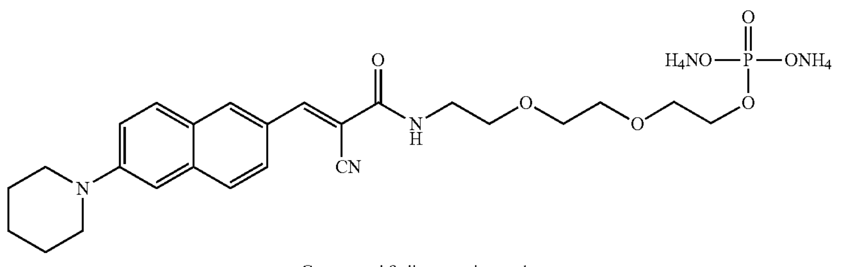

Compound 9 diammonium salt

A solution of Compound 8 (5 mmol, 3.49 g, 1 equiv) in anhydrous $CH_2Cl_2$ (100 mL) was cooled to 0° C. under Argon, and trimethylsilyl bromide (50 mmol, 6.8 ml, 10 equiv) was added via syringe. The reaction mixture was stirred at 0° C. for 30 mins and completion of conversion was monitored by HPLC. The mixture was then quenched with Me0H (~50 mL) and stirred for minutes. The solution was evaporated to dryness; this step was repeated four times.

The organic solvents were evaporated under vacuum, the residue was suspended in trace amount of MeOH, and EtOAc was added to induce precipitation of the phosphonic acid. The residue was filtered and washed with EtOAc (×2). The residue was then dried under vacuum to give the desired phosphate acid.

Treatment of the phosphonic acid with $NH_4OAc$ (25 mmol, 1.93 g, 5 equiv) and 150 mL water at room temperature and kept stirring for another 15 mins to give a clear red/orange solution. The reaction mixture was then lyophilized to give the final product. LC-MS: (ES, m/z) 518 $[M+1]^+$. $^1H$-NMR: (400 MHz, $CD_3OD$) δ 8.31-8.22 (m, 2H), 8.08 (dd, J=8.8, 1.9 Hz, 1H), 7.81 (d, J=9.2 Hz, 1H), 7.74 (d, J=8.8 Hz, 1H), 7.40 (dd, J=9.2, 2.5 Hz, 1H), 7.18 (d, J=2.5 Hz, 1H), 4.08-3.98 (m, 2H), 3.79-3.65 (m, 8H), 3.58 (t, J=5.5 Hz, 2H), 3.45-3.39 (m, 4H), 1.86-1.63 (m, 6H).

Solubility of Compound 9

The solubility of Compound 9 was found to be 20-30 mg/mL in phosphate buffer at pH 7.4.

Pharmacokinetics of Compound 9

Compound 9 was injected into rabbits as a solution in 0.1 M phosphate buffer, pH 7.4 such that rabbits received either 30 mg of Compound 9 (Study 1) or 28 mg of Compound 9 (Study 2). The purpose of these studies was to confirm that Compound 9 could easily be converted into Compound 7 in vivo.

Study 1: Rabbits received a 1.5 mL injection of a 20 mg/mL solution of Compound 9 in 0.1 M phosphate buffer, pH 7.4. Rabbits were sacrificed at the specified time points (N=3 per time point) in the tables below and the average concentration of Compound 9 and Compound 7 was determined in the retina (Table 3), brain (Table 4) and blood (Table 5).

TABLE 3

Average retina concentrations for Compound 9 and Compound 7.

| Time (min) | Avg Compound 9 Conc. (ng/g) | Avg Compound 7 Conc. (ng/g) |
|---|---|---|
| 15 | ND | 10.1 ± 7.30 |
| 30 | ND | 2.13 ± 1.71 |
| 60 | ND | 0.779 ± 0.325 |

TABLE 4

Average brain concentrations for Compound 9 and Compound 7.

| Time (min) | Avg Compound 9 Conc. (ng/g) | Avg Compound 7 Conc. (ng/g) |
|---|---|---|
| 15 | 0.439 ± ND | 0.987 ± 0.273 |
| 30 | ND | ND |
| 60 | ND | ND |

TABLE 5

Average blood concentrations for Compound 9 and Compound 7.

| Time (min) | Avg Compound 9 Conc. (ng/ml) | Avg Compound 7 Conc. (ng/ml) |
|---|---|---|
| 15 | 5443 ± 767 | 217 ± 31.2 |
| 30 | 374 ± 301 | 9.41 ± 1.89 |
| 60 | 24.9 ± 31.8 | 2.10 ± 2.43 |

Study 2: The purpose of this study was to determine if higher concentrations of Compound 9 and/or Compound 7 was present at earlier time points in the tissues specified. Rabbits received a 1.4 mL injection of a 20 mg/mL solution of Compound 9 in 0.1 M phosphate buffer, pH 7.4. Blood was collected from rabbits (N=6) two minutes after receiving Compound 9 to determine the blood concentration at this time point (Table 8). Rabbits were then sacrificed at the specified time points (N=3 per time point) in the tables below and the average concentrations of Compound 9 and Compound 7 were determined in the retina (Table 6), brain (Table 7) and blood (Table 8).

TABLE 6

Average retina concentrations for Compound 9 and Compound 7.

| Time (min) | Avg Compound 9 Conc. (ng/g) | Avg Compound 7 Conc. (ng/g) |
|---|---|---|
| 5 | ND | 682 ± 119 |
| 10 | ND | 183 ± 152 |

TABLE 7

Average brain concentrations for Compound 9 and Compound 7.

| Time (min) | Avg Compound 9 Conc. (ng/g) | Avg Compound 7 Conc. (ng/g) |
|---|---|---|
| 5 | 7.2 ± 2.62 | 316 ± 91.6 |
| 10 | 2.23 ± 0.426 | 68.1 ± 8.86 |

TABLE 8

Average plasma concentrations for Compound 9 and Compound 7.

| Time (min) | Avg Compound 9 Conc. (ng/mL) | Avg Compound 7 Conc. (ng/mL) |
|---|---|---|
| 2 | 67571 ± 18785 | 1480 ± 409 |
| 5 | 39980 ± 11763 | 975 ± 317 |
| 10 | 8859 ± 1311 | 251 ± 13.9 |

Based on this data, it is concluded that Compound 9 is rapidly converted to Compound 7 in vivo in a healthy rabbit model.

Modification of the terminal alcohol group of Compound 7 to a phosphate significantly increased the water solubility. One beneficial feature of Compound 9 diammonium salt is that phosphatases in the blood immediately cleave the phosphate group, generating Compound 7. It has been demonstrated that Compound 7 is delivered past the blood brain barrier (BBB) and, more importantly, into retinal tissue via administration of Compound 9 diammonium salt. Compound 9 is rapidly converted to Compound 7 ($K_{p,brain}$ of Compound 7 was highest at 5 minutes post-dose) and significantly decreased to undetectable values by 30 minutes. $K_{p,brain}$ of Compound 9 was <0.001, suggesting it had primarily been converted to Compound 7 prior to reaching the brain. The circulation time for Compound 7 in the retina is relatively short, with levels of probe significantly decreasing over an hour. Importantly, Compound 7 was delivered at high concentrations to the retinal tissue (682 ng/g) while Compound 9 remained undetectable. In addition, no adverse reactions were noted in rabbits during the time course of this study. Based on the data shown below, it was concluded that Compound 9 is rapidly converted to Compound 7, which compound can 1) fluorescently detect Aβ40 in vitro, 2) emit fluorescence at a wavelength that is detectable using conventional instruments, and 3) penetrate to the retina when administered systemically as Compound 9 (e.g., Compound 9 diammonium salt).

Example 3

Model mice having a detectable target protein, for example, an amyloid beta protein, or a phosphorylated tau protein, or an accumulated mass thereof, are administered Compound 9 intravenously. Retinas of the mice are removed and are mounted on slides. The retinas are washed with PBS 2 times for 5 minutes. A solution of 98% formic acid is added—5 minutes for antigen retrieval. The sampled are washed with distilled water—2 times for 5 minutes. The samples are equilibrated in 1×PBS for 15 minutes, then blocked with 10% goat/donkey serum in 1× PB ST (depending on antibodies) for 1 hour. Samples are covered in foil, and washed with 1× PBS 3 times for 5 minutes each. Samples are stained with DAPI (300 nM or 100 ng/mL) in dark for 10 minutes, then tissues are washed 3×10 minutes with PBS. Antifade DAKO mounting medium is added, and coverslip and kept under foil until imaging.

Fluorescent imaging study of the samples is conducted on a Leica DMI 4000B microscope (Leica, Germany) equipped with a TCS SPE camera and Leica 10, 20 and 40× objectives. The following lasers are used to visualize fluorescent probes pertaining to DAPI (blue, nuclear stain), Compound 7 (green) and hyperphosphorylated tau (red): 408, 488 and 568 nm. Z-stacked images are taken at 40× at 0.5 μm increments to visualize the entire thickness of the tissue. Hyperphosphorylated three repeat tau protein is detected in the retina, producing a detectable fluorescent signal, while in wild type mice of comparable age, no immunostaining with three repeat tau antibody is detected. In conclusion, the study indicates that Compound 9 can be used as a diagnostic agent for detecting amyloid beta protein or hyperphosphorylated tau protein.

Example 4

This example is conducted to determine whether Compound 9 detects Aβ in the retina of a TBI mouse model.

Blast model mice 24 hours after injury and a non-injured mouse are administered Compound 9 intravenously. Mice retinas are scanned by scanning laser ophthalmoscopy (SLO). An image is generated showing the presence of Aβ plaques.

Alternatively, or in addition to retinal scanning, retinal tissues are removed and stained with an anti-Aβ antibody (6E10). The mouse that receives a blast injury displays immunoreactivity to Aβ in the retinal tissue where the uninjured mouse displays no reactivity to 6E10. Compound 7 fluorescently labels retinal deposits that are visible upon fluorescent activation, but does not display any fluorescent enhancement in tissue from the uninjured mouse.

Example 5

Detection of Retinal Aβ Aggregation In Vivo

An in vivo retinal imaging study was conducted using mice before and after receiving a controlled cortical impact (CCI). The CCI model applies a controlled impact to the intact dura after a craniotomy and is a commonly used TBI animal model.

Figure 3:
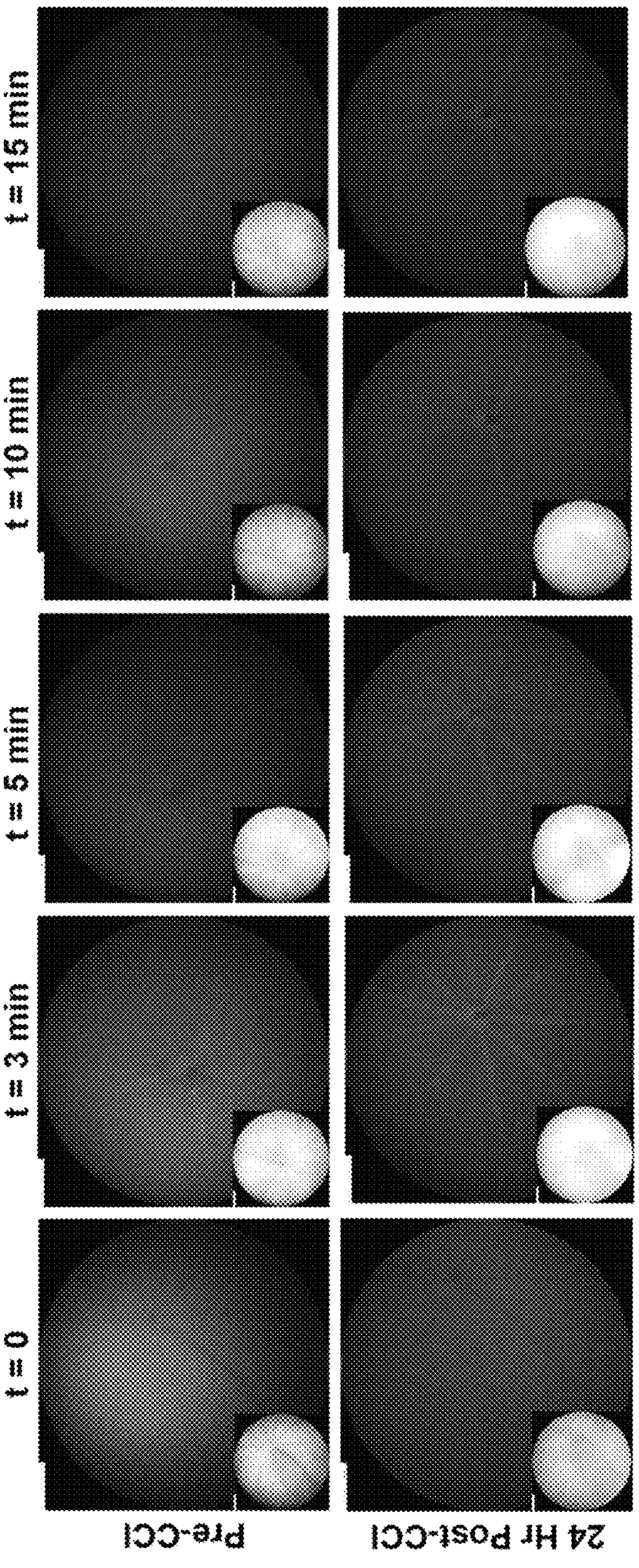
FIG. 3 presents the images of live retinal imaging using Compound 10 with a mouse before and after a CCI. Top Row: Time course retinal imaging of a 3-month-old mouse pre-CCI after iv administration of Compound 10. Time course labeled on the top indicates in vivo retinal imaging time points before (t=0) and after iv administration of Compound 10. Bottom Row: Time course retinal imaging with Compound 10 of the same mouse 24 hours post CCI.

Mice were imaged prior to undergoing a TBI by CCI to obtain baseline retinal images. Anesthetized mice received an i.v. administration of Compound 9 diammonium salt (Compound 10) (15 mg/kg of a 20 mg/mL solution in 0.1 M Phosphate buffer, pH 7.4) before CCI and 24 hours post CCI. As shown in FIG. 3, background fluorescence enhancement was observed in the retinal vasculature 3 minutes after administration of Compound 10 of an uninjured (before CCI) mouse. This enhancement was no longer observed 15 minutes after administration with Compound 10 (FIG. 3, top row).

Twenty-four hours after baseline imaging, to carry out the CCI, mice were anesthetized, the head was mounted in a stereotaxic frame, and a craniotomy was performed over the right side of the motor cortex. Using a stereotaxic impactor, mice received an impact on the right side of the motor cortex using a 5 m/s velocity, 2 mm depth, and 3 mm diameter piston. After injury, the incision was closed with stiches, anesthesia was terminated, and the animal was placed on a heating pad to maintain normal core temperature. Twenty-four hours after CCI, live retinal imaging was conducted on anesthetized mice after i.v. administration of Compound 10. As shown in FIG. 3, the retinal vasculature remained illuminated during the 15-minute imaging period, indicating that Aβ may be present in the vessels (FIG. 3, bottom row). This is in contrast to the pre-CCI imaging where fluorescence enhancement of the vessels was visible 3 minutes post-injection but decreases over the 15-minute imaging period.

This example shows that within 24 hours after a CCI, Compound 9 diammonium salt (Compound 10) can be used to detect a change in the retinal vasculature that may be indicative of Aβ accumulation due to TBI.

Example 6

Early Diagnosis of Prion Through the Eye

Figure 4:
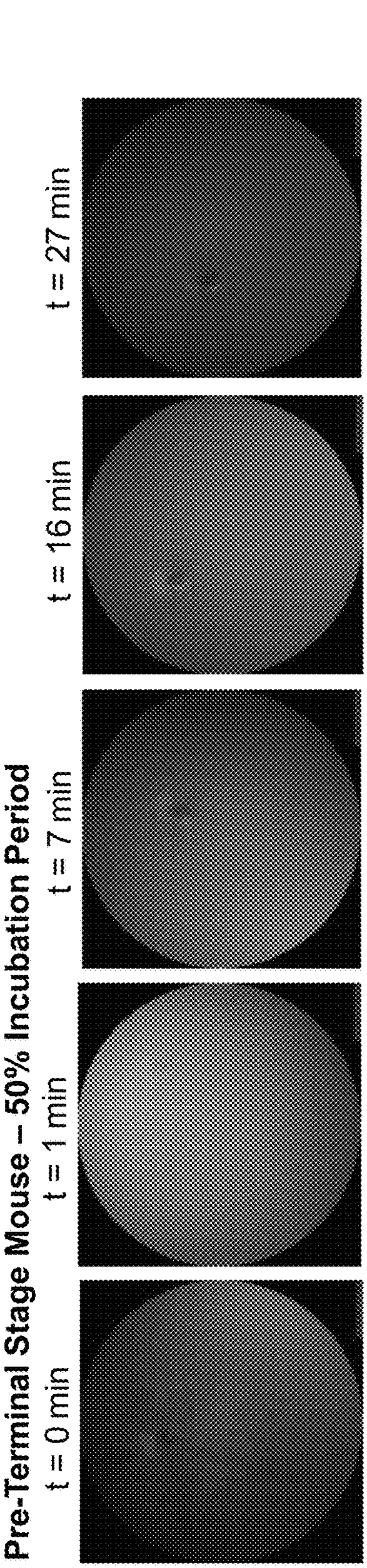
FIG. 4 and FIG. 5 show retinal fluorescence images of pre-symptomatic (FIG. 4), and terminal (FIG. 5) GPI-anchorless mice. Images were acquired on the Phoenix Micron IV rodent retinal imaging system before (pre-injection, t=0) and after (post-injection) systemic administration of Compound 10. Lightened portion in the images indicate areas where retinal prion deposits are observed.
Figure 4:
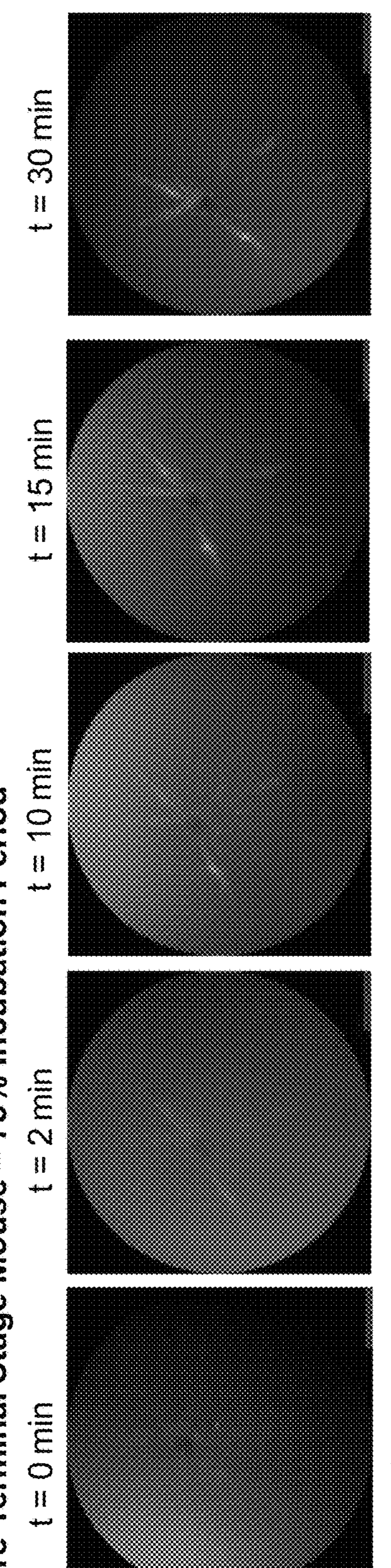
Figure 5:
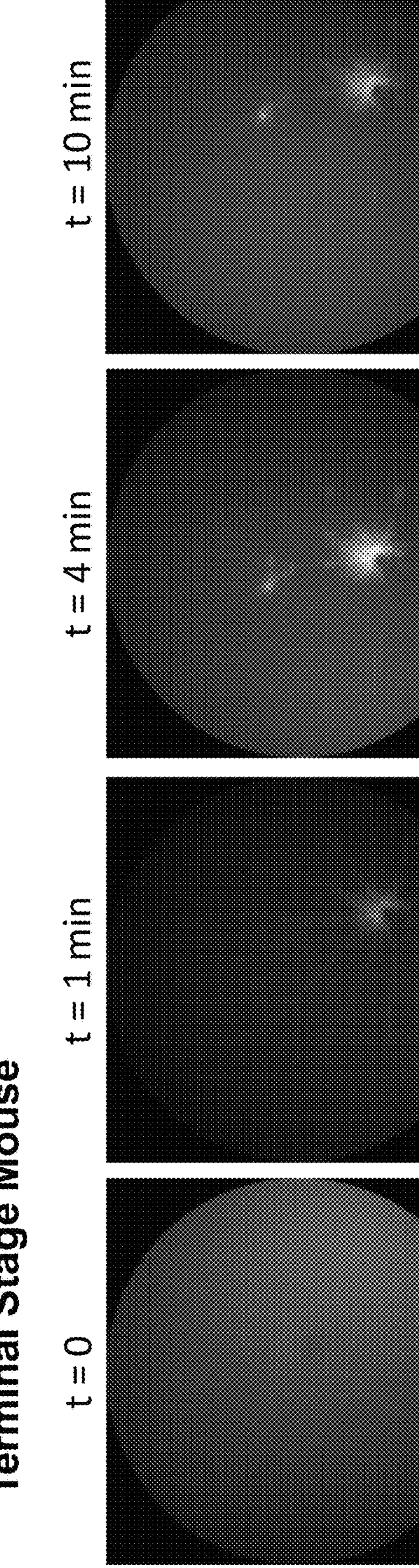

In vivo fluorescence retinal imaging experiments were conducted on live, ketamine anesthetized mice using a Phoenix Micron IV fluorescence rodent retinal imaging system (analogous to a commercial human retinal camera used in fluorescein angiography). Mice were examined after a systemic administration of Compound 10 prior to clinical manifestations of the disease (50% Incubation after inoculation with mouse prions (N=5+N=4 controls) and 75% Incubation after inoculation with mouse prions (N=3+N=4 controls)) and at terminal prion disease (N=4+N=4 controls). As shown in FIG. 4 and FIG. 5, Compound 7, when administered as Compound 10, successfully labelled large objects around the optic disk and vasculature believed to be prion deposits in the retina of both the pre-symptomatic (FIG. 4) and terminally diseased mice (FIG. 5). The mock-infected mice (negative control) showed no signs of retinal amyloid deposits, as expected. For the first time, retinal prions in this mouse model were identified at a pre-symptomatic stage of the disease, indicating that Compound 7, when administered as Compound 10, can label prion deposits prior to clinical diagnosis.

Example 7

Detection of Retinal Aβ in the Diagnosis of Alzheimer's Disease

Ex Vivo Analysis with Human Alzheimer's Disease Tissue: Post-mortem retinal tissue and brains of humans with confirmed or probable Alzheimer's disease were obtained (University of Miami, FL). This study was conducted to determine 1) if there is a correlation between amyloidosis in the brain and retinas of Alzheimer's disease patients, and 2) if compounds as disclosed herein could identify patients with amyloid accumulation in the brain through fluorescence inspection of retinas as a method for diagnosing patients with Alzheimer's disease.

Figure 6C:
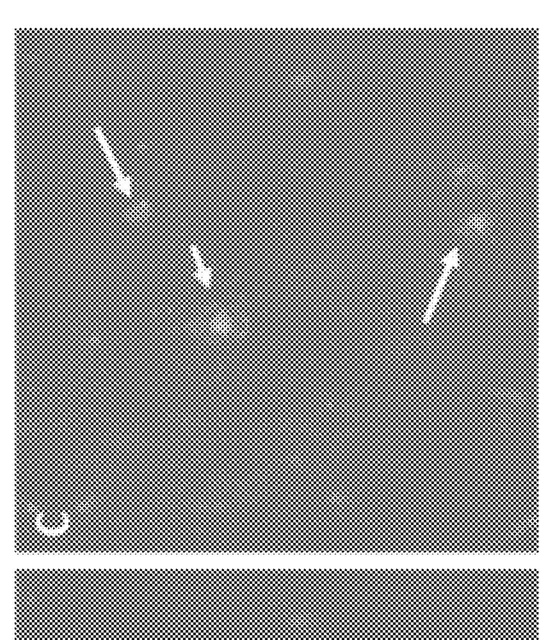
FIGS. 6A-6C show staining of amyloid deposits in the hippocampus from a patient with familial Alzheimer's disease.
Figure 6C:
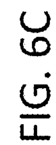
Figure 6B:
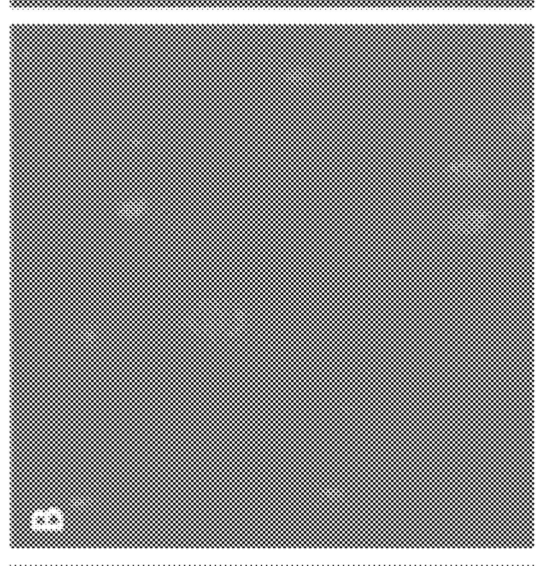
Figure 6A:
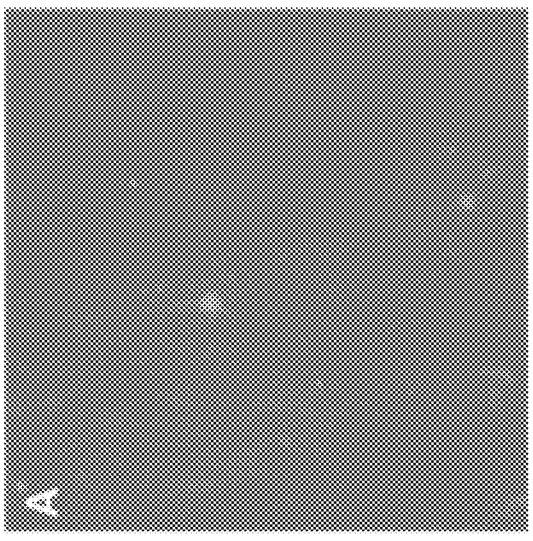

A co-localization experiment was conducted on brain tissue from a patient diagnosed with familial Alzheimer's disease. Free floating sections from the post-mortem hippocampal region of this patient were stained with an Aβ sequence specific antibody (6E10) along with Compound 7. The fluorescence microscopy image in FIG. 6A demonstrates that Compound 7 binds to objects consistent in size and morphology to dense core plaques of Aβ. Significantly, the binding of Compound 7 was indeed co-localized with the immunoreactivity of 6E10 dense core amyloid plaques (FIG. 6C white arrows), but not diffuse objects stained by 6E10. One limitation of 6E10, is that it recognizes a specific sequence of amino acids rather than the aggregation of Aβ which explains the fluorescence of both dense core plaques and other diffuse objects observed in FIGS. 6B and C.

These results support that Compound 7 binds to Aβ plaques associated with Alzheimer's disease. Importantly, this demonstrates the ability Compound 7 to bind to Aβ plaques in both brain and retinal tissue of human Alzheimer's patients. This data shows that Compound 7 can bind Aβ in human tissue, and thus it is contemplated that Compound 9, or a salt thereof (Compound 10) can be used to administer Compound 7 in vivo, to diagnose Alzheimer's Disease.

Example 8

Cerebral Amyloid Angiopathy (CAA)

Detection of Aβ40 In Vivo After Systemic Administration

Two different Tg mouse models for development of vascular amyloid deposits in the retina associated with CAA were developed. $APP^{SwDI}$ and PSAPP mice were selected based on the accumulation of vasculature amyloid deposits in the brain, but to date, the retina had not been explored. $APP^{SwDI}$ mice express the human APP gene (isoform 770) containing the Swedish (K670N/M671L), Dutch (E693Q), and Iowa (D694N) mutations under control of the mouse Thy1 promoter. PSAPP mice express a chimeric mouse/human amyloid precursor protein (Mo/HuAPP695swe) and a mutant human presenilin 1 (PS1-dE9), both directed to CNS neurons by the mouse prion protein promoter. Colonies of mice were bred and screened over time for the development of vascular amyloid deposits in the retina. Mice ranging in age from 12-16 months of both sexes were initially examined. In this age range, mice began to develop cataracts which precluded the ability to image the retina in vivo. Younger mice were therefore selected to examine with Compound 10.

Figure 7:
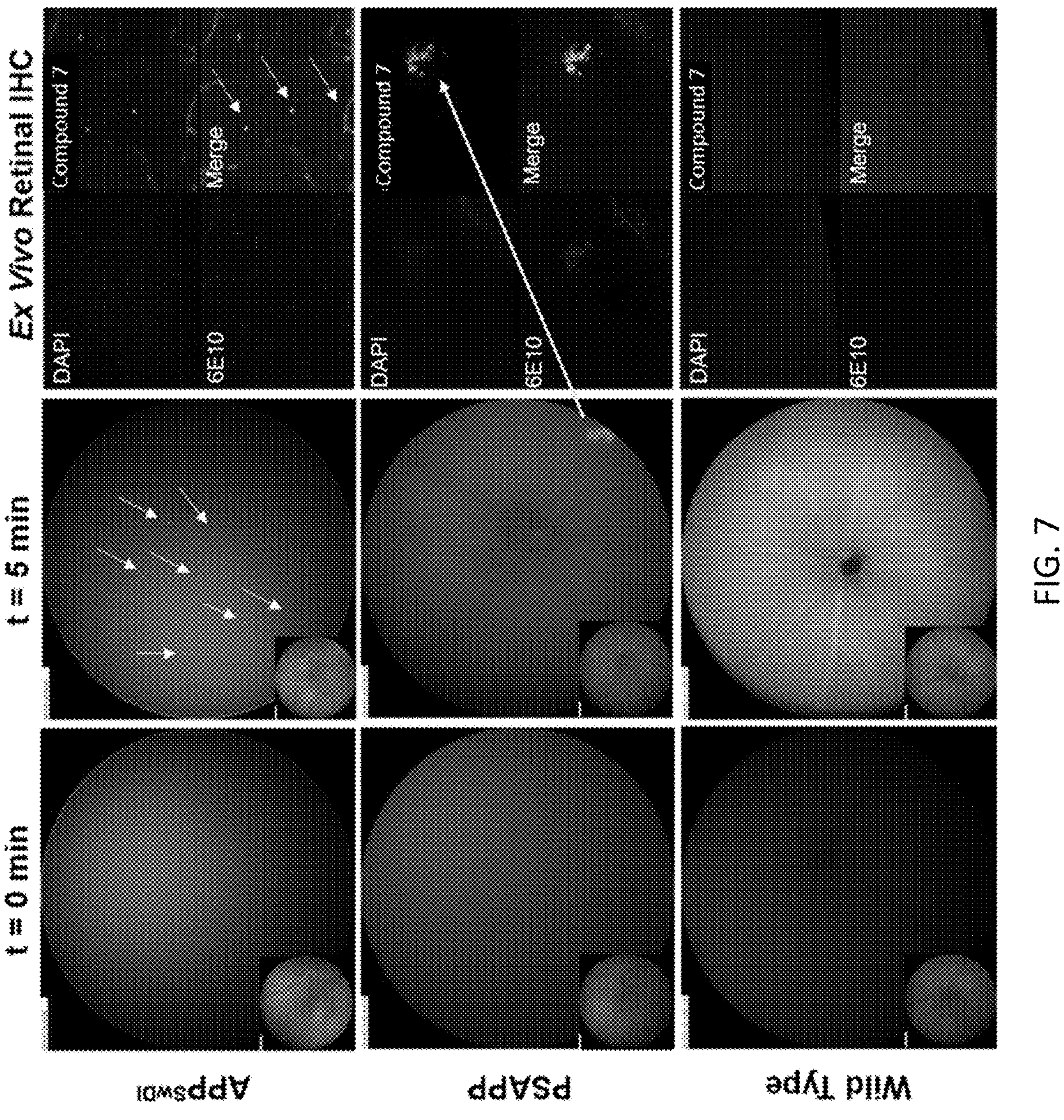
FIG. 7 shows in vivo retinal images and ex vivo IHC from mice after iv administration of Compound 10. APPSwDI (10-month-old, F), PSAPP (10-month-old, F), or wild type (9-month-old, F) retinal images at t=0 (first column) or t=5 minutes (second column) after iv injection with Compound 10. Bright field images (inset) or fluorescence retinal images were obtained using the Phoenix Micron IV rodent retinal imaging system. Last column: Ex vivo IHC of retina stained with a DAPI nuclear stain or 6E10 antibody. Labelling of Compound 7 is from in vivo injection with Compound 10 (i.e. no further staining was performed). Each channel is shown individually, and all three channels merged to demonstrate co-localization of Compound 7 with 6E10. White arrows indicate areas where deposits are observed.

Retinal images were acquired from 8-10 month old $APP^{SwDI}$ (N=6, 1 male and 5 female), PSAPP (N=2, female), and wild type control mice (N=3 females). Mice were imaged 5 minutes after intravenous (i.v.) tail vein injection with 25 μL of Compound 10 (20 mg/mL in phosphate buffer, pH 7.4). A 10 month old female $APP^{SwDI}$ mouse revealed small, brightly fluorescent deposits primarily along the vasculature (FIG. 7 white arrows). Fluorescence decreased over a 15-minute time course at which point the mouse was sacrificed and the brain and retinal tissue was harvest for immunohistochemistry (IHC). As shown in FIG. 7, these deposits were fluorescently labeled with Compound 7 in the retina and importantly co-localized with a sequence specific antibody for Aβ (6E10). Interestingly, it demonstrates that Compound 7, when administered as Compound 10, labels both vessels and diffuse deposits in the retinal tissue of this $APP^{SwDI}$ mouse (FIG. 7, top right corner).

Figure 8:
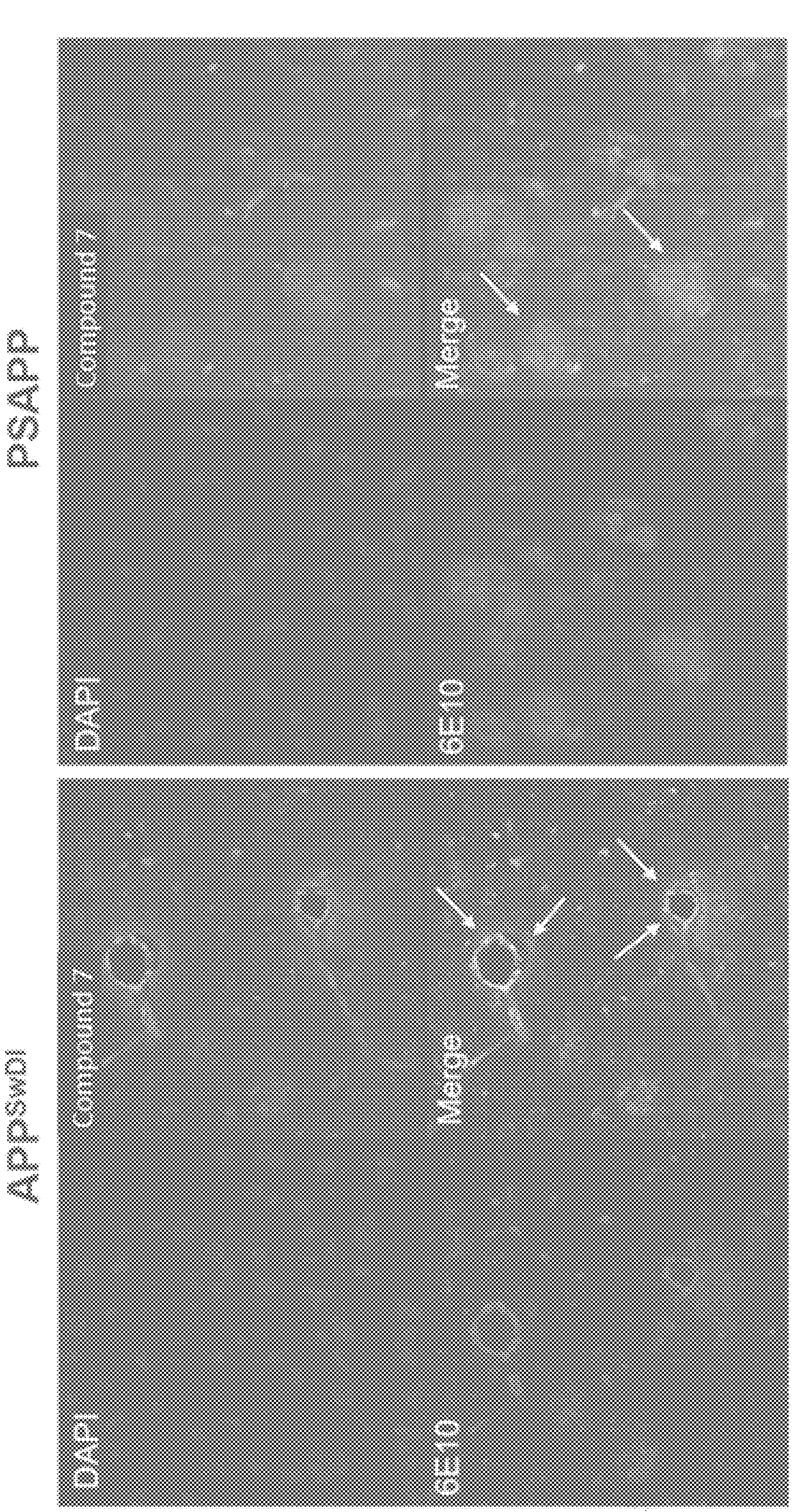
FIG. 8 shows ex vivo IHC of brain sections from mice 15 minutes after receiving an iv administration of Compound 10. Brain sections were stained with a DAPI nuclear stain and 6E10. Labelling of Compound 7 is from injection with Compound 10 in vivo. APPSwDI: white arrows show amyloid deposits along a vessel labeled with Compound 7 and 6E10. PSAPP.

To better understand the brain/eye correlation, the brain was examined by IHC. The $APP^{SwDI}$ mouse showed amyloid deposition within blood vessels as well as diffuse amyloid plaques in the brain (FIG. 8, white arrows), like what was observed in the retinal IHC, indicating good correlation. For the PSAPP mouse injected with Compound 10, a large deposit in the lower right quadrant of the retina was observed in vivo (FIG. 7). That same deposit was confirmed to be Aβ as demonstrated by the co-localization of Compound 7 with 6E10. In the brain, dense core plaques were observed analogous to that of Alzheimer's pathology, but vascular amyloid deposition was not observed in the brain of this mouse (FIG. 8). Again, this demonstrated good brain/eye correlation as no vascular pathology was observed in the retina of this PSAPP mouse. Lastly, no deposits were observed in wild type mice injected with Compound 10 as expected (FIG. 7, bottom row).

Ex Vivo Analysis of Human Brain Tissue from Post-Mortem CAA Patients

Post-mortem brain tissue from patients diagnosed with CAA were examined to de-risk the translation from the limited robust preclinical animal models to humans. This study was designed to understand the fundamental basis of fluorescently detecting amyloids using human tissue. FIG. 9 demonstrates that compounds disclosed herein can detect amyloid deposits in the brains of human CAA patients.

Human CAA brain tissue and healthy control brain tissue was acquired (University of California, San Diego, CA). Table 9 summarizes the patient population including age, sex, and diagnosis of the post-mortem human brain tissue examined with Compound 7. All CAA patients were female and ranged in age from 70-93 years. Control brains were obtained from cognitively normal patients that ranged in age from 82-94 years from both male and female donors. Free floating sections of the median frontal cortex from human CAA brain and control brains were stained with an Aβ sequence specific antibody (6E10) along with Compound 7.

TABLE 9

| Patient population examined ex vivo with Compound 7. | | | |
|---|---|---|---|
| Patient Number | Age | Sex | Diagnosis |
| CAA 1 | 87 | F | PSP[1], cerebrovascular disease, CAA and lacunar infarcts |
| CAA 2 | 70 | F | Alzheimer's disease Braak stage VI with severe CAA |
| CAA 3 | 93 | F | Alzheimer's disease Braak stage VI with Lewy body and severe CAA |
| CAA 4 | 77 | F | Alzheimer's disease Braak stage VI with severe CAA |
| Healthy 1 | 82 | M | Normal |
| Healthy 2 | 84 | F | Normal |
| Healthy 3 | 84 | M | Normal |
| Healthy 4 | 94 | M | Normal |

[1]Progressive Supranuclear Palsy.

The fluorescence microscopy images in FIG. 9 demonstrates that Compound 7 binds to objects with a consistent pattern associated with CAA amyloid pathology. Significantly, the binding of Compound 7 was indeed co-localized with the immunoreactivity of 6E10 in CAA-laden plaques within the vessels (FIG. 9), but not diffuse objects stained by 6E10. One limitation of 6E10, is that it recognizes a specific sequence of amino acids rather than the aggregation of Aβ, which explains the immunoreactivity of both plaques and other diffuse objects observed in CAA brains and healthy controls. Importantly, staining with Compound 7 was only observed in CAA brains and was absent in healthy control brains (FIG. 9). The results demonstrated that Compound 7 successfully stains amyloid deposits associated with CAA in human tissue.

This example demonstrates that the disclosed compounds detect Aβ40 in vivo in tg animals (administered as an i.v.-bolus injection, FIG. 7), and ex vivo with human CAA disease tissues (FIG. 9). Ante-mortem imaging of vascular amyloid deposits in the retina of a diseased mouse was performed using Compound 10. Ex vivo analysis of the same diseased retina confirmed the in vivo findings that deposits were indeed Aβ. Accordingly, the disclosed compounds can provide an effective and affordable imaging agent for the diagnosis of CAA.

Example 9

Non-Invasive Ophthalmic Diagnostic for Parkinson's Disease

The following example shows that the compounds described herein provide a Parkinson's Disease diagnostic test, which may to have two major impacts. First, it is contemplated that the presently disclosed diagnostic compounds will identify patients with Parkinson's Disease potentially years earlier than current criteria, allowing for early interventions with current therapies. Second, the presently disclosed diagnostic compounds can assist in the development of disease modifying therapeutics by optimizing selection of patients to treat, thereby improving the likelihood of a successful clinical outcome of Parkinson's Disease drug candidates.

Based on the premise that α-syn accumulates in the retina, the following model was produced and utilized to test the efficacy of the presently disclosed diagnostic compounds for development of a diagnostic probe that can target α-syn in the eye to diagnose and monitor the progression of Parkinson's Disease.

Two transgenic mouse models of Parkinson's Disease (D-line and Line 61) were examined for retinal α-syn deposits. The models selected produce α-syn deposition in the brain, but to date production in the retina had not been determined. Retinal images of mice were obtained before and after i.v. administration of Compound 10. After live imaging, mice were sacrificed, and the brain and retina were harvested for immunofluorescence and biochemistry.

D-Line Parkinson's Disease Tg Mouse Model

Preliminary ex vivo retinal staining with SYN1 did not detect α-syn in the retinal tissue. As expected, Compound 10 did not detect any retinal deposits in vivo or ex vivo. Accordingly, the D-Line model is not a viable model to explore retinal α-syn deposits.

Line 61 Parkinson's Disease Tg Mouse Model

Retinal α-syn deposits were observed in vivo in 4/14 mice after systemic administration of Compound 10. Ex vivo retinal staining with the antibody SYN1 confirmed α-syn was present in the retinal tissue in the mice where deposits were observed in vivo. Accordingly, Line 61 model manifest retinal α-syn in ~30% of mice and was useful in showing the utility of the disclosed compounds. WT mice (N=10) were evaluated as controls and no retinal α-syn was detected in vivo or ex vivo, as anticipated. Brain tissue was extracted post-mortem from mice after the last imaging session and stained with DAPI and a SYN1 antibody confirming the presence of α-syn in the Line 61 Mouse brain.

Using the Line 61 model, it was confirmed that Compound 7, via administration of Compound 10, is specific for α-syn deposits associated with Parkinson's Disease and can detect retinal α-syn deposits in vivo (FIG. 10).

To confirm objects detected in vivo were α-syn, retinal tissue was extracted post-mortem from mice after the last imaging session and stained with DAPI and a SYN1 antibody (FIG. 11).

This example shows that i.v. administration of Compound 10 can detect retinal α-syn in vivo with Line 61 mice and that the fluorescence enhancement is specific for α-syn. Accordingly, Compound 7 co-localizes with an anti-alpha-synuclein antibody (SYN1) in brain and retinal tissue of Tg mice.

To broaden the understanding and utility of administration of Compound 10 as a retinal diagnostic for Parkinson's disease, the following studies were performed.

To confirm that administration of Compound 10 can reproducibly detect retinal α-syn deposits, Line 61 Tg mice received two iv administrations of 15 mg/kg Compound 10 separated by a 7 day wash out period. A similar number of deposits were observed during both imaging sessions. FIG. 12 shows that administration of Compound 10 can reproducibly detect retinal α-syn deposits in the same animal.

To understand the lowest dose of Compound 10 that can detect retinal α-syn, Line 61 Tg mice were injected with 3 mg/kg and 15 mg/kg Compound 10 separated by a 6 day wash out period. The same number of deposits were observed for both dose concentrations. FIG. 13 shows that administration of Compound 10 can detect retinal α-syn deposits at a lower dose of 3 mg/kg.

Ex Vivo Staining of Human Parkinson's Disease Eyes

To understand if Compound 7 (active drug) can detect retinal α-syn in human eyes, human retinal tissue was extracted post-mortem from both a healthy patient and a patient diagnosed with Parkinson's Disease, and stained with Compound 7, DAPI and a SYN1 antibody.

Eye dissection: Cornea, iris and lens were removed from the eye cup and the eye placed into 4% PFA for 1 hour. The eye cup was dissected using the macula as a guide to estimate orientation of eye, then retina recovered and split leaflets into 4 pieces (Superior, Inferior, Temporal, and Nasal). The different regions were mounted on separate slides.

Flatmount retinal staining: The tissue was fixed in room temperature 4% PFA for 20 minutes, washed, permeabilized, blocked (2.5% goat serum in PBST), stained with Alpha-synuclein antibody (SYN-1) at a dilution of 1:1000 and incubate overnight at 4° C., washed with PBST (3 times for 5 minutes), incubated with secondary antibody (Alexa fluor 647 anti-mouse) in dark for 1 hr at RT. The tissue was then washed with PB ST (3 times for 5 minutes), incubated with 60 μM Compound 7 for 30 minutes at RT, washed with PBS (3 times for 10 minutes), incubate with DAPI (300 nM or 100 ng/mL) in dark for 10 minutes, and washed with PBS (3 times for 5 minutes). The tissue was then mounted using antifade DAKO mounting media.

As a control, a pair of retinas were extracted from a 72-year-old male who died from leukemia with no neurological disorders, brain cancer or eye related diseases. The retinas were stained with Compound 7 and SYN-1 Ab (alpha-synuclein). In retinal post-mortem tissue from a healthy human patient, there was very little or no co-localization of Compound 7 and alpha-synuclein (SYN-1 Ab). FIG. 14 and FIG. 15 show example images from each region of the right and left retina.

A pair of retinas were extracted from a 71-year-old male diagnosed with Parkinson's disease (PD). The retinas were stained with Compound 7 and SYN-1 Ab (alpha-synuclein). In the retina of a human PD patient, there is co-localization of Compound 7 and Alpha-Synuclein deposits (SYN-1 Ab) in all regions. FIG. 16 and FIG. 17 show example images from each region of the right and left retina.

To determine the number of objects co-stained with Compound 7 and SYN1, the average number of objects co-stained with Compound 7 and SYN1 was quantified. This was completed for each quadrant of both the left and right eye (Table 10 and Table 11).

TABLE 10

Manual quantification of objects observed in each retinal region of the right eye

| Region | No. of areas inspected | Average No. of co-stained objects | Average No. of singly-stained objects SYN-1 | Compound 7 |
|---|---|---|---|---|
| Superior | 8 | 16 | 0.62 | 0.5 |
| Inferior | 8 | 12.12 | 0.25 | 0.75 |
| Temporal | 8 | 11.62 | 0.75 | 0.5 |
| Nasal | 8 | 14.3 | 0.12 | 1.75 |

*Note:
each area corresponds to ~250,000 $\mu m^2$ (i.e., a 500 μm × 500 μm field)

TABLE 11

Manual quantification of objects observed in each retinal region of the left eye

| Region | No. areas inspected | Average No. of co-stained objects | Average No. of singly-stained objects SYN-1 | Compound 7 |
|---|---|---|---|---|
| Superior | 8 | 20 | 1.62 | 0.25 |
| Inferior | 8 | 13.6 | 0.37 | 0.87 |
| Temporal | 8 | 12.37 | 0.75 | 0.5 |
| Nasal | 8 | 13 | 0 | 0.75 |

*Note:
each area corresponds to ~250,000 $\mu m^2$ (i.e., a 500 μm × 500 μm field)

The co-localized objects could be visualized fluorescently in flatmount retina samples that were co-stained with Compound 7 and the SYN-1 Ab. Co-localization of Compound 7 and SYN-1 Ab was most prevalent at about ⅔ the distance away from the optic nerve and the edge of the retina close to or a serrata. Co-localization of Compound 7 and SYN-1Ab was prevalent in all the regions, with most of the co-localization observed in Superior region of Left retina.

FIG. 18 shows that Compound 7 co-localizes with SYN1 in all four quadrants of a pair of Parkinson's Disease eyes. These data show that Compound 7 can detect α-syn in human retinal tissue.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A compound represented by formula:

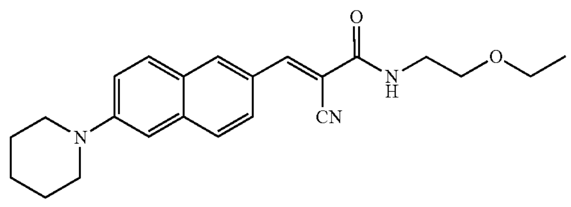

-continued
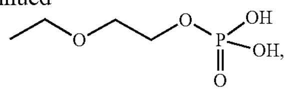
or a pharmaceutically acceptable salt thereof.
2. A pharmaceutical composition comprising the compound of claim 1, or a pharmaceutically acceptable salt thereof, and a pharmaceutically acceptable carrier.
3. The compound of claim 1, wherein the salt is a diammonium salt.
* * * * *